US012808878B2

(12) United States Patent
Chung et al.

(10) Patent No.: US 12,808,878 B2
(45) Date of Patent: Nov. 24, 2026

(54) N-ACRYLOYLINDOLES AND METHODS OF USE

(71) Applicant: Versitech Limited, Hong Kong (CN)

(72) Inventors: Yik Sham Clive Chung, Hong Kong (CN); Hin Yuk Lai, Hong Kong (CN); Tin Yan Koo, Hong Kong (CN); Yui Yan Hillary Yip, Hong Kong (CN)

(73) Assignee: Versitech Limited, Hong Kong (CN)

( * ) Notice: Subject to any disclaimer, the term of this patent is extended or adjusted under 35 U.S.C. 154(b) by 529 days.

(21) Appl. No.: 18/307,905

(22) Filed: Apr. 27, 2023

(65) Prior Publication Data

US 2024/0103005 A1 Mar. 28, 2024

Related U.S. Application Data

(60) Provisional application No. 63/365,391, filed on May 26, 2022.

(51) Int. Cl.
*G01N 33/68* (2006.01)
*C07D 209/08* (2006.01)
*C07D 403/12* (2006.01)

(52) U.S. Cl.
CPC ....... *G01N 33/6815* (2013.01); *C07D 209/08* (2013.01); *C07D 403/12* (2013.01); *G01N 2458/00* (2013.01)

(58) Field of Classification Search
CPC .................................................. G01N 33/6815
See application file for complete search history.

(56) References Cited

U.S. PATENT DOCUMENTS

2016/0252509 A1 9/2016 Cravatt et al.
2020/0048204 A1 2/2020 Zhang et al.
2020/0292555 A1 9/2020 Cravatt et al.

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

"Find ETDs Home » Thesis Resources » Find ETDs" Online: "https://ndltd.org/thesis-resources/find-etds/" Accessed Jan. 31, 2023.*

Irwin "Zinc—A Free Database of Commercially Available Compounds for Virtual Screening" J. Chem. Inf. Model. 2005, 45, 177-182.*

Kim "PubChem in 2021: new data content and improved web interfaces" Nucleic Acids Research, 2021, vol. 49, Database issue Published online Nov. 5, 2020.*

STN Registry/Zregistry (CAS Registrysm) Sep. 2016 2 pages.*

Rabalski, ACS Chemical Biology 2019 14 (9), 1940-1950.*

Zambaldo , Journal of the American Chemical Society 2020 142 (19), 8972-8979.*

Abegg, D., et al., "Proteome-Wide Profiling of Targets of Cysteine reactive Small Molecules by Using Ethynyl Benziodoxolone Reagents", Angew. Chem. Int. Ed., 2015, 54(37):10852-10857.

Abo, M., et al., "Optimization of Caged Electrophiles for Improved Monitoring of Cysteine Reactivity in Living Cells", Chembiochem, 2017, 18(1):1-6.

Adibekian, A., et al., "Click-generated triazole ureas as ultrapotent in vivo-active serine hydrolase inhibitors", Nature Chemical Biology, 2011, 7(7):1-10.

Alcock, L. J., et al., "Chemical methods for mapping cysteine oxidation", Chem Soc Rev, 2018, 47(1):231-268.

Backus, K. M., et al., "Proteome-wide covalent ligand discovery in native biological systems", Nature, Jun. 23, 2016, 534(7608):1-22.

Bailey, M. H., et al., "Comprehensive Characterization of Cancer Driver Genes and Mutations", Cell, 2018, 173 (2):1-37.

Bechtel, T. J., et al., "Profiling Cysteine Reactivity and Oxidation in the Endoplasmic Reticulum", ACS Chemical Biology, 2020, 15(2):543-553.

Blum, G., et al., "Dynamic imaging of protease activity with fluorescently quenched activity-based probes", Nature Chemical Biology, Sep. 2005, 1(4):203-209.

Boike, L., et al., "Discovery of a Functional Covalent Ligand Targeting an Intrinsically Disordered Cysteine within MYC", Cell Chemical Biology, Dec. 17, 2020, 27:1-28.

Chung, C. Y.-S., et al., "Covalent targeting of the vacuolar H+-ATPase activates autophagy via mTORC1 inhibition", Nature Chemical Biology, Aug. 2019, 15:1-16.

Dickens, F., "Interaction of Halogenacetates and SH compounds. The reaction of halogenacetic acids with glutathione and cysteine. The mechanism of iodoacetate poisoning of glyoxalase", Biochemical Journal, 1933, 27 (4):1141-1151.

Eaton, J. K., et al., "Selective covalent targeting of GPX4 using masked nitrile-oxide electrophiles", Nature Chemical Biology, 2020, 16(5):1-16.

Friedman, M., et al., "Relative Nucleophilic Reactivities of Amino Groups and Mercaptide lons in Addition Reactions with α,β-Unsaturated Compounds1, 2", Journal of American Chemical Society, Aug. 20, 1965, 87(16):3672-3682.

Hoch, D. G., et al., "Cysteine-reactive probes and their use in chemical proteomics", Chem. Commun., 2018, 54 (36):4501-4512.

Isor, A., et al., "Identifying cysteine residues susceptible to oxidation by photoactivatable atomic oxygen precursors using a proteome-wide analysis", RSC Chemical Biology, 2021, 2(2):577-591.

Kato, D., et al., "Activity-based probes that target diverse cysteine protease families", Nature Chemical Biology, Jun. 2005, 1(1):33-38.

Kudo, M., et al., "Lenvatinib versus sorafenib in first-line treatment of patients with unresectable hepatocellular carcinoma: a randomised phase 3 non-inferiority trial", The Lancet, 2018, 391:1163-1173.

(Continued)

*Primary Examiner* — Nizal S Chandrakumar
(74) *Attorney, Agent, or Firm* — SALIWANCHIK, LLOYD & EISENSCHENK

(57) ABSTRACT

The subject invention pertains to a new class of compounds, N-acryloylindole (NAIs), and methods of using NAIs as cysteine-reactive probes for proteome-wide cysteine profiling and imaging of thiol oxidative modifications. NAIs are capable of imaging oxidized thiols in cells facing oxidative stress by confocal fluorescence microscopy. NAIs can capture populations of cysteines, particularly those involved in gene expression and regulation.

3 Claims, 47 Drawing Sheets

(56) References Cited

OTHER PUBLICATIONS

Kuljanin, M., et al., "Reimagining high-throughput profiling of reactive cysteines for cell-based screening of large electrophile libraries", Nature Biotechnology, May 2021, 39(5):1-18.
Lai, H., et al., "N-Acryloylindole-alkyne (NAIA) enables profiling new ligandable hotspots in chemoproteomics experiments and imaging thiol oxidation", ChemRxiv, 2022, doi:10.26434/chemrxiv-2022-khww5, pp. 1-39.
Leichert, L. I., et al., "Quantifying changes in the thiol redox proteome upon oxidative stress in vivo", PNAS, Jun. 17, 2008, 105(24):8197-8202.
Motiwala, H. F., et al., "Tunable Heteroaromatic Sulfones Enhance in-Cell Cysteine Profiling", J. Am. Chem. Soc., 2020, 142(4):1801-1810.
Nielsen, M. L., et al., "lodoacetamide-induced artifact mimics ubiquitination in mass spectrometry", Nature Methods, Jun. 2008, 5(6):459-460.
Ostrem, J. M., et al., "K-Ras(G12C) inhibitors allosterically control GTP affinity and effector interactions", Nature, Nov. 28, 2013, 503(7477):1-14.
Qin, W., et al., "Chemoproteomic profiling of itaconation by bioorthogonal probes in inflammatory macrophages", Journal of the American Chemical Society, Jun. 4, 2020, 142(25):1-7.
Resnick, E., et al., "Rapid Covalent-Probe Discovery by Electrophile-Fragment Screening", Journal of the American Chemical Society, 2019, 141(22):8951-8968.
Serafimova, I. M., et al., "Reversible targeting of noncatalytic cysteines with chemically tuned electrophiles", Nature Chemical Biology, May 2012, 8(5):471-476.
Shannon, D. A., et al., "Investigating the Proteome Reactivity and Selectivity of Aryl Halides", Journal of the American Chemical Society, 2014, 136(9):3330-3333.
Smyth, D. G., et al., "Some Reactions of N-Ethylmaleimide1", Journal of the American Chemical Society, 1960, 82 (17):4600-4604.
Speers, A. E., et al., "Chemical Strategies for Activity-Based Proteomics", ChemBioChem, 2004, 5(1):41-47.
Tokunaga, K., et al., "Bicyclobutane Carboxylic Amide as a Cysteine-Directed Strained Electrophile for Selective Targeting of Proteins", Journal of the American Chemical Society, 2020, 142(43):1-10.
Wang, C., et al., "A chemoproteomic platform to quantitatively map targets of lipid-derived electrophiles", Nature Methods, Jan. 2014, 11(1):1-10.
Ward, C. C., et al., "NHS-Esters as Versatile Reactivity-Based Probes for Mapping Proteome-Wide Ligandable Hotspots", ACS Chem Biol., Jun. 16, 2017, 12(6):1-12.
Weerapana, E., et al., "Quantitative reactivity profiling predicts functional cysteines in proteomes", Nature, Dec. 9, 2010, 468:1-8.
Wishart, D. S., et al., "DrugBank 5.0: a major update to the DrugBank database for 2018", Nucleic Acids Research, 2018, 46:D1074-D1082.
Wright, A. T., et al., "A Suite of Activity-Based Probes for Human Cytochrome P450 Enzymes", J. Am. Chem. Soc., 2009, 131(30):10692-10700.
Xu, T., et al., "ProLuCID: An improved SEQUEST-like algorithm with enhanced sensitivity and specificity", Journal of Proteomics, 2015, 129:16-24.

* cited by examiner

NAIA-5 + *N*-acetylcysteine methyl ester → Adduct

| | $k$ ($M^{-1}s^{-1}$) |
|---|---|
| NAIA-4 | 221.35 ± 6.85 |
| NAIA-5 | 155.73 ± 8.24 |
| IAA | 1.795 ± 0.567 |
| 3 | 0.469 ± 0.130 |
FIG. 1H
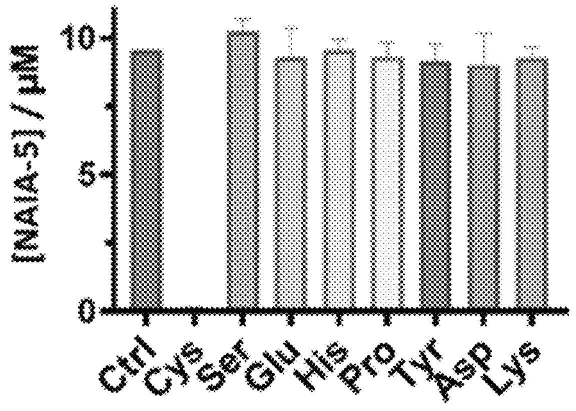
FIG. 1I
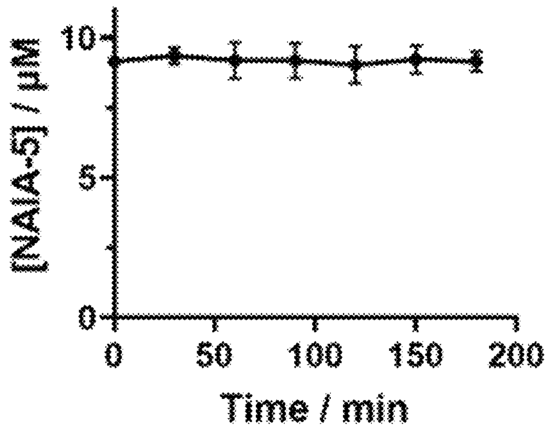
FIG. 1J

| Gene Name | Protein Name | Liganded Cys by NAIA-5 | Protein Functions |
|---|---|---|---|
| CCNT1 | O60563 | 261 | Transcription regulations |
| SSBP3 | Q9BWW4 | 80 | Transcription regulations |
| DMTF1 | Q9Y222 | 264 | Transcription regulations |
| GRHL2 | Q6ISB3 | 446 | Transcription regulations |
| ZFHX2 | Q9C0A1 | 239, 242 | Transcription regulations |
| ZBTB2 | Q8N680 | 392, 395 | Transcription regulations |
| ZNF217 | O75362 | 674 | Transcription regulations |
| ZNF480 | Q8WV37 | 3 | Transcription regulations |
| ZNF639 | Q9UID6 | 462, 465 | Transcription regulations |
| ZNF829 | Q3KNS6 | 354, 357 | Transcription regulations |
| ZNF846 | Q147U1 | 368, 371 | Transcription regulations |
| HKR1 | P10072 | 14 | Transcription regulations |
| NFE2 | Q16621 | 4 | Transcription regulations |

| Gene Name | Protein Name | Liganded Cys by NAIA-5 | Protein Functions |
|---|---|---|---|
| AKAP8L | Q9ULX6 | 211 | Transcription regulations, RNA processing and splicing |
| TSEN15 | Q8WW01 | 13 | RNA processing and splicing |
| CELF2 | O95319 | 3 | RNA processing |
| RBFOX1 | Q9NWB1 | 3 | RNA processing |
| LAGE3 | Q14657 | 23 | RNA processing |
| CSTF2T | Q9H0L4 | 150 | RNA processing |
| ERI1 | Q8IV48 | 75 | RNA processing |
| SRP19 | P09132 | 3 | RNA binding |
| NUP188 | Q5SRE5 | 9 | RNA transport |
| GRHL2 | Q6ISB3 | 446 | Regulations of transcription and DNA methylation |
| SAP30BP | Q9UHR5 | 127 | Regulations of histone deacetylation |
| MGMT | P16455 | 150 | DNA damage and repair |

FIG. 6D

Commonly used reagent for cysteine profiling

Iodoacetamide-alkyne (IA-alkyne)

In this work

*N*-Acryloylindolines (NAines)

*N*-Acryloylindoles (NAIs)

NAIA-4

N-acetylcysteine methyl ester

Adduct

NAIA-C5-Amide

N-acetylcysteine methyl ester

Adduct

| | $k$ ($M^{-1}s^{-1}$) |
|---|---|
| NAIA-C5-Amide | 344.84 |
| NAIA-C4-Amide | 205.48 |
| NAIA-C3-Amide | 129.77 |
| NAIA-5 | 155.73 ± 8.24 |
| IAA | 1.795 ± 0.567 |

1 2 3 4 5

D1 D2 D3

5 + D3

NAI-DTB-1

N-ACRYLOYLINDOLES AND METHODS OF USE

CROSS-REFERENCE TO RELATED APPLICATION

This application claims the benefit of U.S. Provisional Application Ser. No. 63/365,391, filed May 26, 2022, which is hereby incorporated by reference in its entirety including any tables, figures, or drawings.

BACKGROUND OF THE INVENTION

Cysteine is one of the most intriguing amino acids due to its intrinsically high nucleophilicity and sensitivity to oxidation.[1-12] It can govern and regulate a variety of important biological processes, ranging from cell proliferation and differentiation to programmed cell death,[4,10,13] through catalyzing chemical transformations in active sites of enzymes, such as proteases,[10-13] oxidoreductases[9,10-14] and acyltransferases.[10,15] Its susceptibility to undergo redox modifications allows it to serve as an important amino acid residue for post-translational modifications, including oxidation,[1,4-7,9,11,16] glutathionylation,[4,7,9,11] and S-nitrosylation,[4,7,9] which can then alter protein conformations and/or functions to mediate downstream signaling. It also plays key roles in dedicating protein structures by forming disulfide bonds.[5, 9-10] or coordinating metal ions.[5,10,17-19]

Activity-based protein profiling (ABPP) has been demonstrated to be a powerful platform for proteome-wide profiling of functional cysteines.[3,6,8,10,11,20-25] These cysteines are reactive and nucleophilic, thus with the use of activity-based probes, which show specific chemical reactions with the cysteines to form covalent bonds,[3,6,80,20,22-24,26-28] this allows for successful capture of the functional cysteines, which can then be identified by gel-based and/or mass spectrometry (MS)-based ABPP experiments.[5,6,8,10,11,20, 22-24,28,29] Interestingly, many of these liganded cysteines by an activity-based probe in ABPP experiments are found to associate with disease development and propagation, and this facilitates further study on using electrophiles, with acrylamide[12,23,24,30-36] and chloroacetamides.[5,12,24,28,33,35,37], to target these new ligandable hotspots for therapy. Therefore, an activity-based probe is a critical component in ABPP experiments and determines the pool of cysteines and proteins, which can be liganded and eventually targeted for therapy, i.e. the activity-based probe can define druggable hotspots.

Examples of activity-based probes for cysteine include maleimides,[5,9,10,22,40-42] α,β-unsaturated ketones[5,12,23,24,30-36,43-48] and haloacetamides[5,12,22,24,28,33,35,37,49-51], with iodoacetamide alkyne (IAA)[3,5-10,27,52-54] as the most widely used probe for proteome-wide cysteine profiling. Nonetheless, challenges in using IAA for cysteine profiling have been encountered, including side reactions with other nucleophilic amino acids, such as lysine and serine, as well as oxidized thiols, such as sulfenic acid.[55-56] Also, a large excess of IAA is required for adequate labeling of functional cysteines due to its relatively slow reactivity. This limits its application to cell lysate labeling only and not for live cells due to high toxicity from the high working concentration of IAA, in addition to its low biostability (FIG. 7).[57,58] As a result, development of new cysteine-reactive compounds as better cysteine probes[5,6,51,56,59-62] is one of the active research areas to advance ABPP and other cysteine profiling experiments.

Acrylamide compounds have higher biostability than iodoacetamides,[63] as well as excellent selectivity for the thiol group on cysteine through the thiol-Michael addition reaction.[23,31,32,36] Yet, low cysteine reactivity has been found in aqueous buffer solution for acrylamide compounds, similar to iodoacetamides.[33]

A cysteine-reactive probe is the key component in ABPP platform and can define the pool of ligandable cysteines and hence the population of proteins that can be targeted by covalent ligands. The conventional cysteine-reactive probe, iodoacetamide-alkyne (IAA), shows only fair reaction kinetics and selectivity with cysteine. Together with its high cellular toxicity and low biostability, this limits the full potential of ABPP platform for biological studies and drug research. Therefore, there remains a need for novel cysteine-reactive probes.

BRIEF SUMMARY OF THE INVENTION

The subject invention pertains to a novel class of cysteine-reactive compounds, N-acryloylindoles (NAIs) which contain an acrylamide warhead on the indole nitrogen (FIG. 7). To turn acrylamide compounds into a cysteine-reactive probe, the acrylamides can be activated with higher electrophilicity, so that they can react more readily with nucleophilic cysteines. The acrylamide group can be formed using scaffold with a less electron-rich nitrogen, and indole nitrogen is among the least nucleophilic due to the aromaticity of indole and delocalization of its lone pair a electrons over the whole molecule.[64] In certain embodiments, NAIs can be further functionalized with an alkyne handle by our established synthetic route (FIGS. 8A-8B), yielding NAI-alkyne (NAIA) as a cysteine-reactive probe for gel-based and Mass Spectrometry (MS)-based Activity-Based Protein Profiling (ABPP) experiments. In certain embodiments, NAIA shows a faster reaction with cysteine in aqueous buffer solution than the conventional cysteine probe IAA. A negative control compound, N-acryloylindoline (NAine), which lacks the delocalization of π electrons from the acrylamide warhead over the whole molecule, reacts much slower than NAIA. In certain embodiments, despite the higher reactivity, NAIA can retain excellent selectivity for cysteine over other amino acids, as well as good biostability. NAIA can be capable of labeling cysteines in both cell lysates and live cells. In certain embodiments, NAIA can be used to image thiol oxidation in cells under oxidative stress by confocal fluorescence microscopy.

In certain embodiments, NAI and/or NAIA can serve as probes for imaging thiol reactivity and functionality in biological samples. In addition to the application for fluorescence imaging, NAIA can be utilized as a probe for MS-based ABPP experiments and capture a larger and a significantly different populations of cysteines than IAA, particularly those involved in gene expression and regulation.

BRIEF DESCRIPTION OF THE DRAWINGS

FIGS. 1A-1J. LC-MS analysis on the reaction between Cys-reactive compounds and small amino acids in aqueous buffer solution. (FIG. 1A) Chemical equation showing thiol-Michael addition of NAIA-5 with N-acetylcysteine methyl ester (N-Ac-Cys-OMe), a N- and C-terminal protected cysteine, to form the adduct product. (FIGS. 1A-1E) NAIA-5 (10 μM) in aqueous buffer solution (PBS-MeOH, 4:1, v/v) was incubated with N-Ac-Cys-OMe (250 μM). At indicated time intervals, an aliquot of the solution mixture was sent for LC-MS analysis. Selected ion chromatograms (SIC) at m/z=325 and 524, corresponding to the molecular ion of $[NAIA-5+H]^+$ and $[Adduct+Na]^+$ respectively, show a consumption of NAIA-5 with concomitant formation of the Cys adduct. The mass spectra (MS) at 6.20 and 5.60 min confirm the identity of NAIA-5 and adduct. (FIGS. 1F-1G) Changes in Cys-reactive compound concentration over time upon incubation with N-Ac-Cys-OMe (250 μM) in aqueous buffer solution (PBS-MeOH, 4:1, v/v). (FIG. 1H) Biomolecular rate constant of reactions between cysteine-reactive compounds and N-Ac-Cys-OMe. (FIG. 1I) Changes in level of NAIA-5 after incubation with amino acids for 30 min, showing excellent selectivity toward Cys over other amino acids. (FIG. 1J) Stability of NAIA-5 in the aqueous buffer solution in the absence of Cys (n=3).

(FIG. 2A) Gel-based ABPP analysis of NAIA-5 and IAA on in vitro Cys labeling of HepG2 cell lysates. HepG2 cell lysates (100 μg) were incubated with NAIA-5 or IAA at indicated concentrations for 1 h, following by CuAAC reaction with azide-fluor 545 (25 μM). The labeled proteins were then boiled with sampling buffer, and read out by in-gel fluorescence after SDS-PAGE. (FIG. 2B) HepG2 cell lysates (100 μg) were pre-incubated with NAIA-5 or IAA at indicated concentrations and time intervals. The labeled proteins were then reacted with azide-fluor 545 (5 μM) by CuAAC reaction, boiled with sampling buffer, and read out by in-gel fluorescence after SDS-PAGE. (FIG. 2C) HepG2 cells were incubated with NAIA-5 or IAA at indicated concentrations and time intervals. The cells were then lysed, labeled with azide-fluor 545 (5 μM) by CuAAC reaction, boiled with sampling buffer, and the labeled proteins were then visualized by in-gel fluorescence after SDS-PAGE. (FIG. 2D and FIG. 2E) Quantification data for the experiments in (FIG. 2A) and (FIG. 2C) respectively. Quantified data were shown in average±SD from n=3 (for FIG. 2A) and 2 (for FIG. 2C) biological replicates/group. Statistical significance is expressed as *$p<0.05$; $p<0.01$; *$p<0.001$; ****$p<0.0001$.

(FIG. 3A) HepG2 cells on 8-well chambered slide were incubated with NAIA-5 or IAA (10 μM) for the indicated time intervals. The cells were then washed with PBS and fixed by 4% paraformaldehyde. The fixed cells were washed with PBS, permeabilized by PBS+0.3 vol % Triton X-100 and reacted with azide-fluor 545 (20 μM) by CuAAC reaction at room temperature in dark for 1 h. The stained cells were washed with PBS and further incubated with Hoechst (8.2 μM) for 15 min. The cells were then washed by PBS and imaged by confocal fluorescence microscopy. (FIG. 3B) Cellular fluorescence intensity as determined by ImageJ. Quantified data were shown in average±SD from n=30 cells from 3 different biological replicates/group. Statistical significance is expressed as ****$p<0.0001$; $^{\#\#\#\#}p<0.0001$ between NAIA-5 and IAA with the same incubation time. (FIG. 3C) Cell viability of 231MFP cells after incubation with NAIA-4 or IAA for 2 h, as indicated by WST-8 assay. Quantified data were shown in average±SD from n=3 different biological replicates/group.

(FIG. 4A) Schematic cartoon illustrating the experimental setup to monitor oxidative modifications of cellular thiols. HepG2 cells were first pretreated by solvent vehicle or $H_2O_2$(0.5 or 1 mM) in complete medium for 15 min. The cells were then washed with PBS and incubated with high concentration of NAIA-5 or IAA (50 μM) in complete medium at 37° C. for 10 min. This short and fast snapshot of free cellular thiols is important because thiol oxidative modifications are in general unstable and highly reversible. Then, the cells were washed with PBS, fixed by 4% paraformaldehyde and permeabilized by PBS with 0.5% Triton X-100. NAIA-5 labeled proteins were then installed with Fluor 545 through CuAAC reactions with azide-fluor 545 (4 μM). After the reaction, the cells were washed, stained with Hoechst 33342, washed and imaged in PBS by confocal fluorescence microscope. A decrease in cellular fluorescence intensity should be observed if the probe can monitor changes in free thiol level in cells under oxidative stress. (FIG. 4B) Confocal fluorescence microscopy images of HepG2 cells after snapshot by NAIA-5 and IAA (50 μM, 10 min). The two images were recorded by the same imaging parameters. (FIGS. 4C-4F) Confocal fluorescence microscopy images of HepG2 cells probed by NAIA-5 or IAA. Merged images are composed of images from brightfield, NAIA-5/IAA and Hoechst channel. Cellular fluorescence intensity was determined by ImageJ. Quantified data were shown in average±SD from n=30 cells from 3 different biological replicates/group. Statistical significance is expressed as $p<0.01$ and **$p<0.0001$; n.s. denotes not significant. Scale bar=20 μm.

(FIG. 5A) Number of probe-modified peptides identified in the MS experiment outlined in FIG. 13. Quantified data were shown in average±SD from n=3 different replicates/group. (FIG. 5B) Modifications on different amino acids by NAIA-5 and IAA, respectively, as identified from the MS experiment. (FIG. 5C) Number of probe-modified proteins identified in the triplicate experiment. (FIG. 5D) Analysis on probe-modified proteins by NAIA-5 and IAA, respectively, using DrugBank database, and the functions of these proteins by Gene Ontology database. (FIG. 5E) Gene Ontology analysis of the biological processes involved by the probe-modified proteins, with the top 20 unique processes regulated by NAIA-5 shown in the bar chart. Those highlighted in red are associated with gene expression and regulation.

FIGS. 6A-6D. LC-MS/MS-based chemoproteomics experiment to investigate in-cell Cys profiling of HepG2 by NAIA-5 and IAA. (FIG. 6A) Number of cysteine labeled by NAIA-5 and IAA (10 μM) in live HepG2 cells from a duplicate experiment. (FIG. 6B) Number of probe-modified proteins identified in the duplicate experiment. (FIG. 6C) Analysis using DrugBank database to determine the availability of pharmacophores to drug NAIA-5-labeled proteins. (FIG. 6D) New protein targets associated with gene expression and regulations and their cysteines which are liganded by NAIA-5 only but not by IAA.

is not suitable for live-cell experiment due to high toxicity. NAine has slow reaction kinetics with cysteine ($k<10^0$ $M^{-1}$ $s^{-1}$) and no delocalization of π electrons of the acrylamide warhead over the whole molecule. NAIs have excellent selectivity toward cysteine, fast reaction kinetics with cysteine ($k>10^2$ $M^{-1}$ $s^{-1}$), delocalization of π electrons making the acrylamide warhead highly electrophilic and reactive toward cysteine, and lower cellular toxicity and can be used in gel-based and MS-based cysteine-profiling experiments.

Figure 8A:
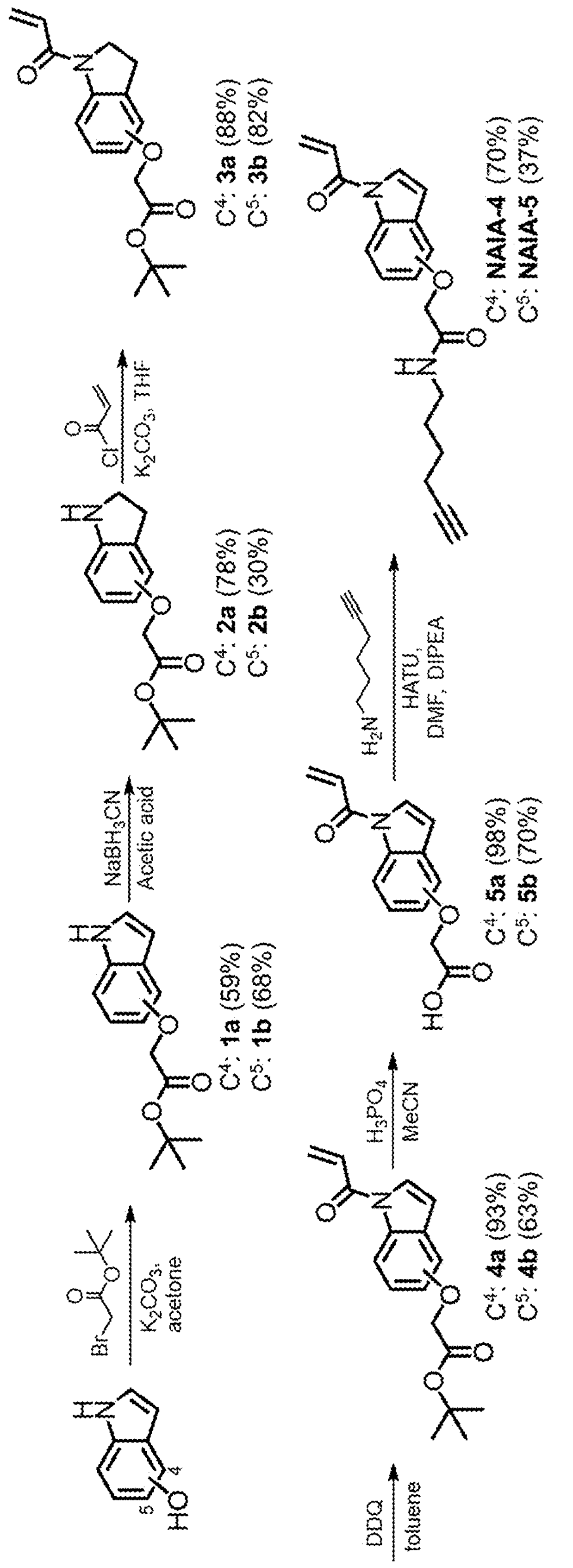
Figure 8B:
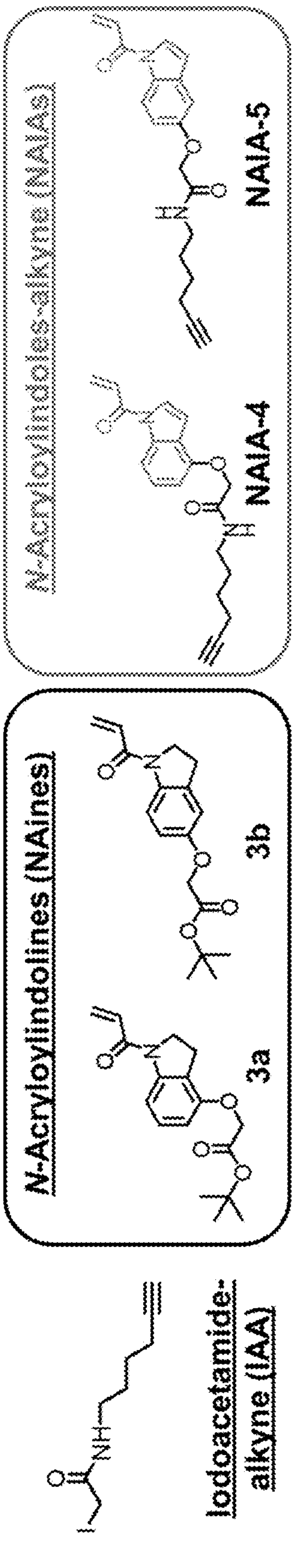
Figure 9A:
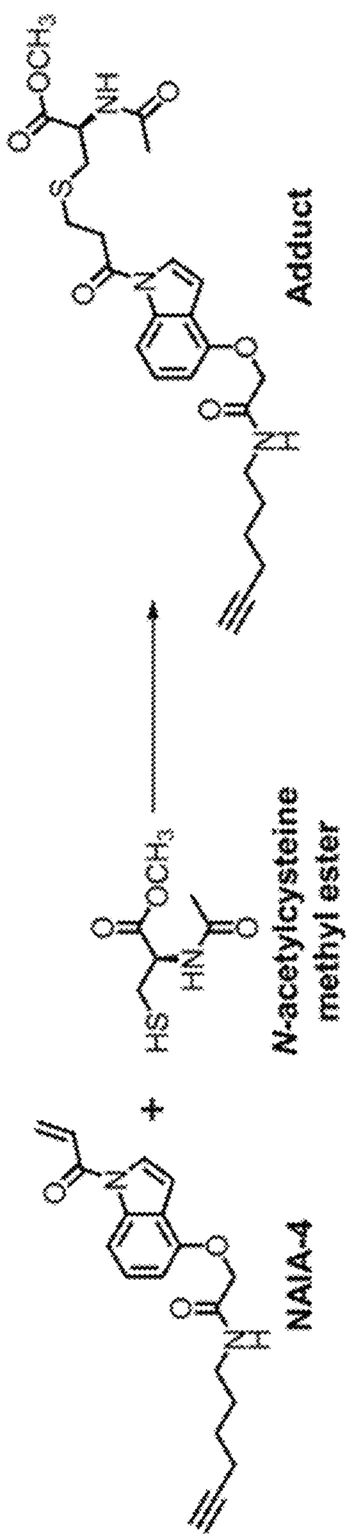
Figure 9B:
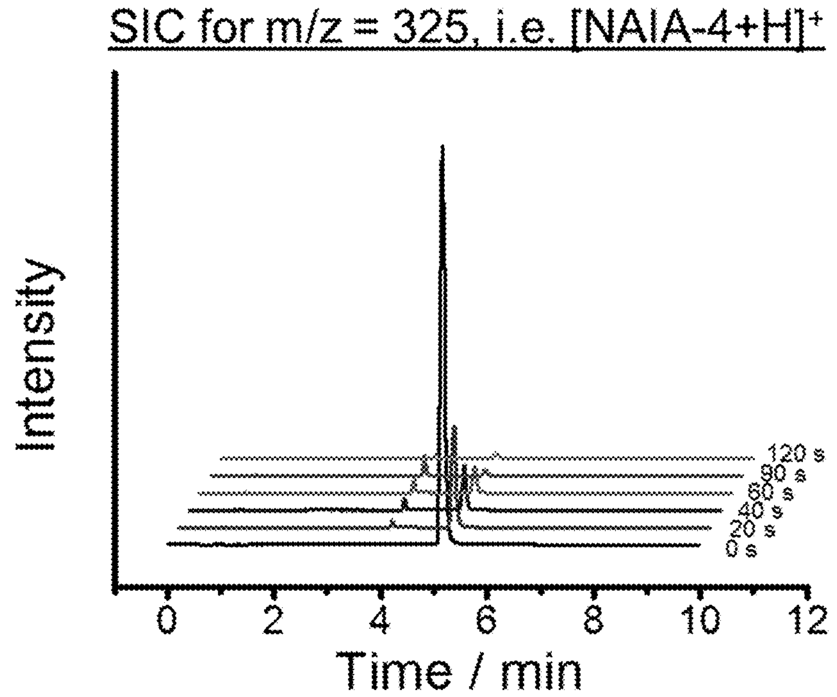
Figure 9C:
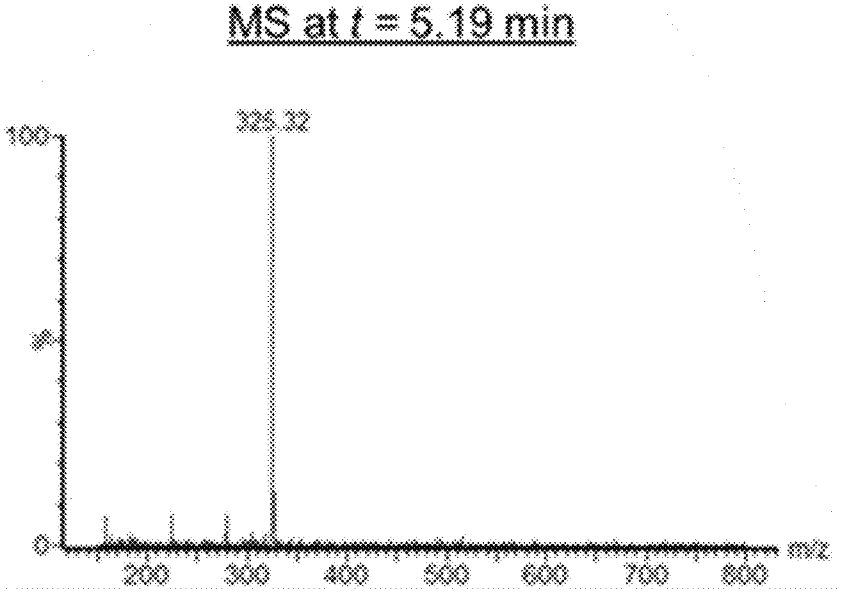
Figure 9D:
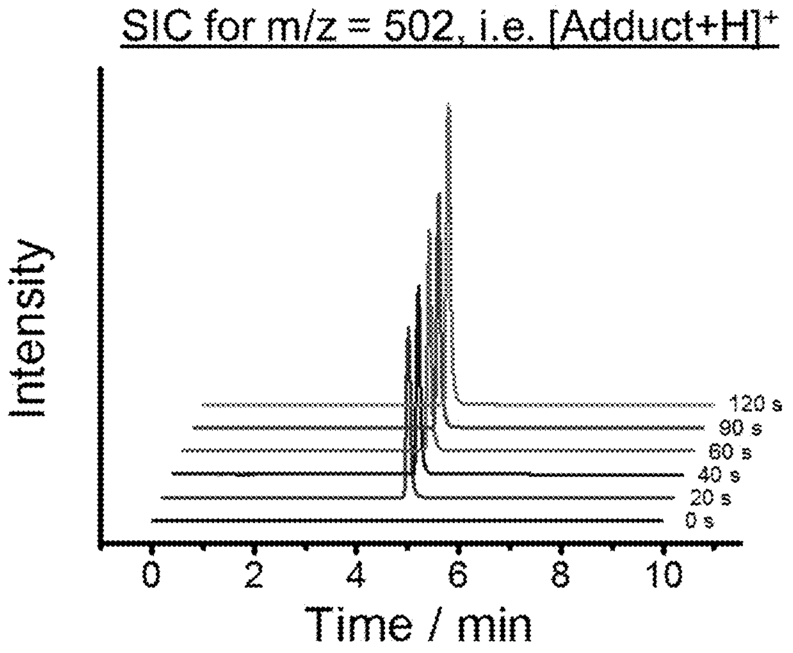
Figure 9E:
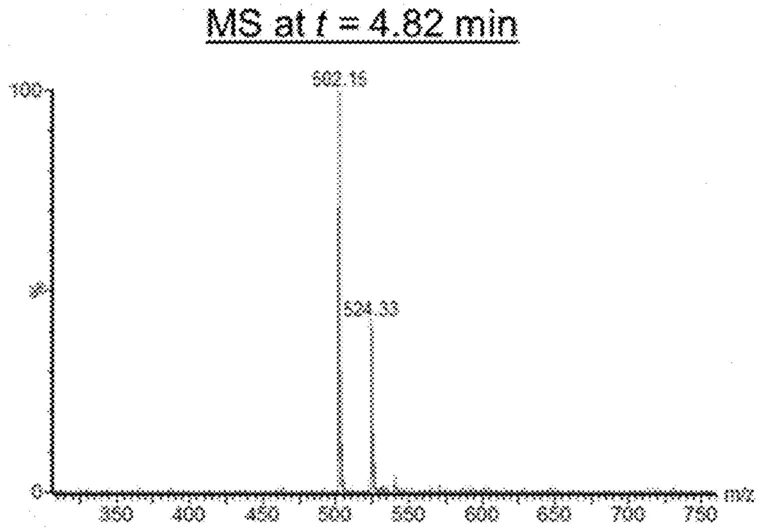
Figure 9F:
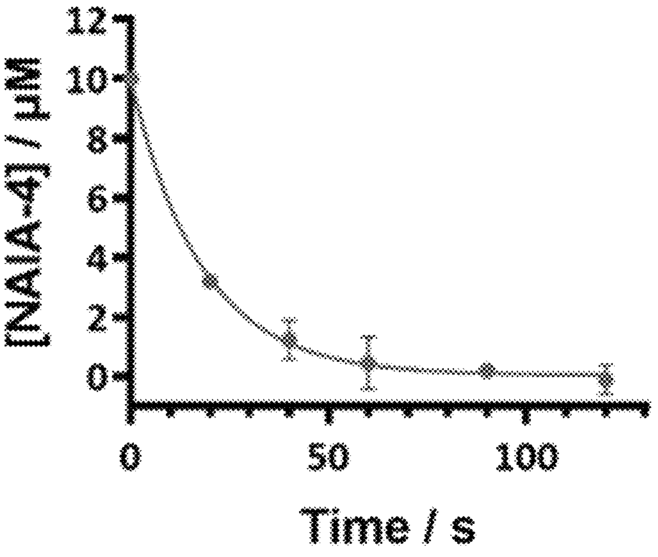
Figure 9G:
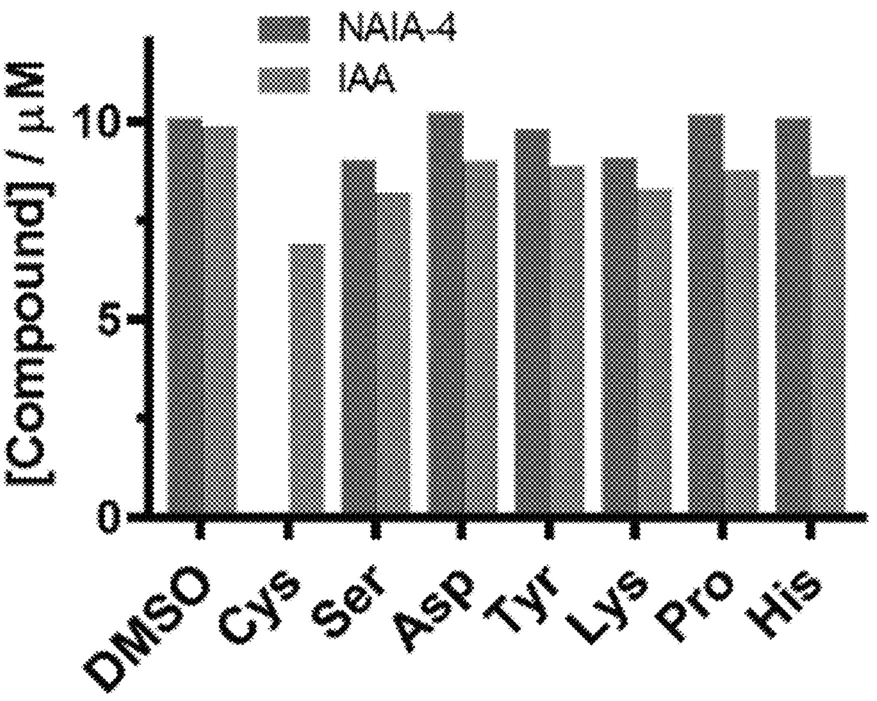

FIGS. 8A-8B. (FIG. 8A) Synthetic scheme for N-acryloylindole-alkynes, and negative control compounds, N-acryloylindolines. (FIG. 8B) Chemical structures of commonly used cysteine-reactive probe, iodoacetamide-alkyne (IAA), and novel NAines and NAIAs reported in this study FIGS. 9A-9G. LC-MS analysis on the reaction between NAIA-4 and small amino acids in aqueous buffer solution. (FIG. 9A) Chemical equation showing thiol-Michael addition of NAIA-4 with N-acetylcysteine methyl ester (N-Ac-Cys-OMe), a N- and C-terminal protected cysteine, to form the adduct product. (FIGS. 9B-9E) NAIA-4 (10 μM) in aqueous buffer solution (PBS-MeOH, 4:1, v/v) was incubated with N-Ac-Cys-OMe (250 μM). At indicated time intervals, an aliquot of the solution mixture was sent for LC-MS analysis. Selected ion chromatograms (SIC) at m/z=325 and 502, corresponding to the molecular ion of $[NAIA-45+H]^+$ and $[Adduct+H]^+$ respectively, show a consumption of NAIA-4 with concomitant formation of the Cys adduct. The mass spectra (MS) at 5.19 and 4.82 min confirm the identity of NAIA-5 and adduct. (FIG. 9F) Changes in NAIA-4 level over time upon incubation with N-Ac-Cys-OMe (250 μM) in aqueous buffer solution (PBS-MeOH, 4:1, v/v). (FIG. 9G) Selectivity of NAIA-4 toward reaction with Cys over other nucleophilic amino acids, as compared to IAA.

FIGS. 10A-10D. Gel-based ABPP experiments of NAIA-4 to investigate its ability to label Cys in cell lysates and live cells. (FIGS. 10A-10B) 231MFP cell lysates (20 μg) were incubated with NAIA-4 or IAA at indicated concentrations for 30 min, following by CuAAC reaction with azide-fluor 545 (5 μM). The labeled proteins were then boiled with sampling buffer, and read out by in-gel fluorescence after SDS-PAGE. Quantified data were shown in average±s.e.m. from n=3 replicates/group. Statistical significance vs untreated control is expressed as *p<0.05; *p<0.001, and vs different treatment groups is expressed as ##p<0.01; ###p<0.001. (FIGS. 10C-10**D) 231MFP cells were pre-treated with NAIA-4 or IAA at indicated concentrations for 1 h. The cells were then washed with DPBS and lysed in DPBS by probe sonication. The cell lysates were labeled with azide-fluor 545 (25 μM) by CuAAC reaction, and the labeled protein were detected by in-gel fluorescence after SDS-PAGE. Quantified data were shown in average±s.e.m. from n=3 biological replicates/group. Statistical significance is expressed as *p<0.05; ***p<0.001.

Figure 11:
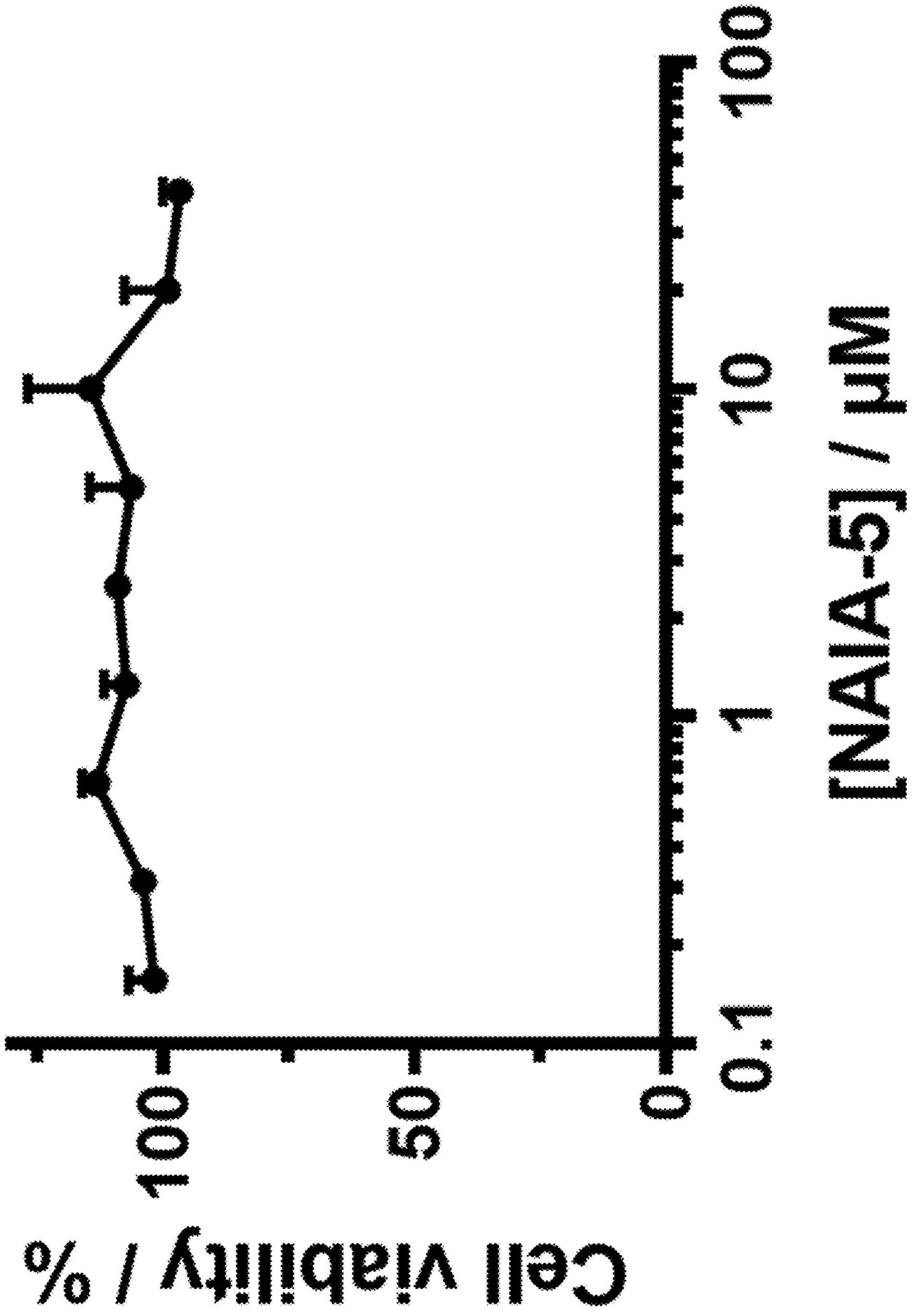

FIG. 11. MTT assay reveals no significant changes in viability of HepG2 cells after treatment with NAIA-5 for 1 h. Quantified data were shown in average±SD from n=3 biological replicates/group.

Figure 12A:
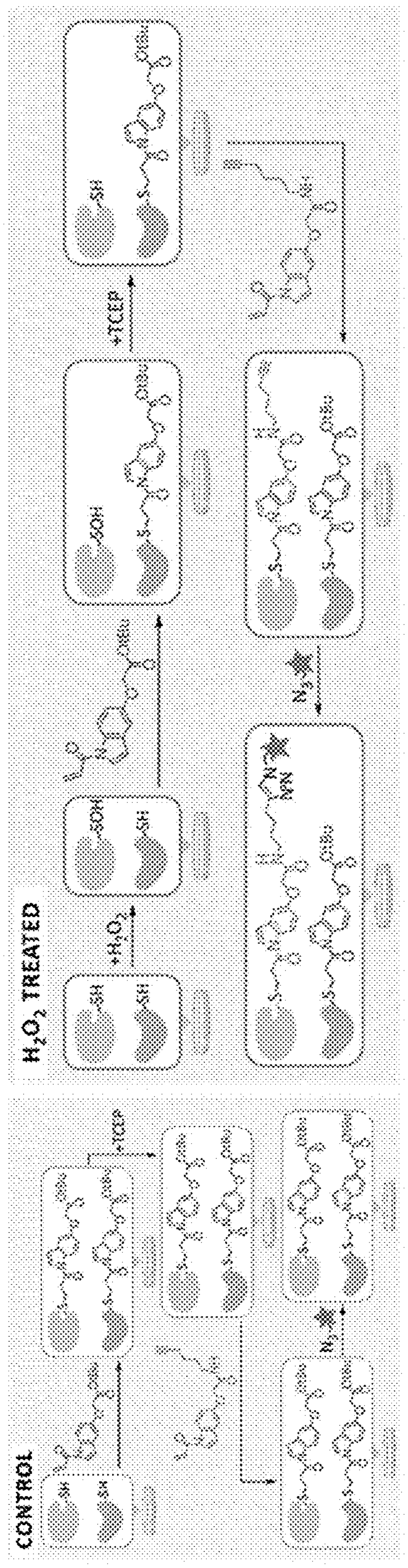
Figure 12B:
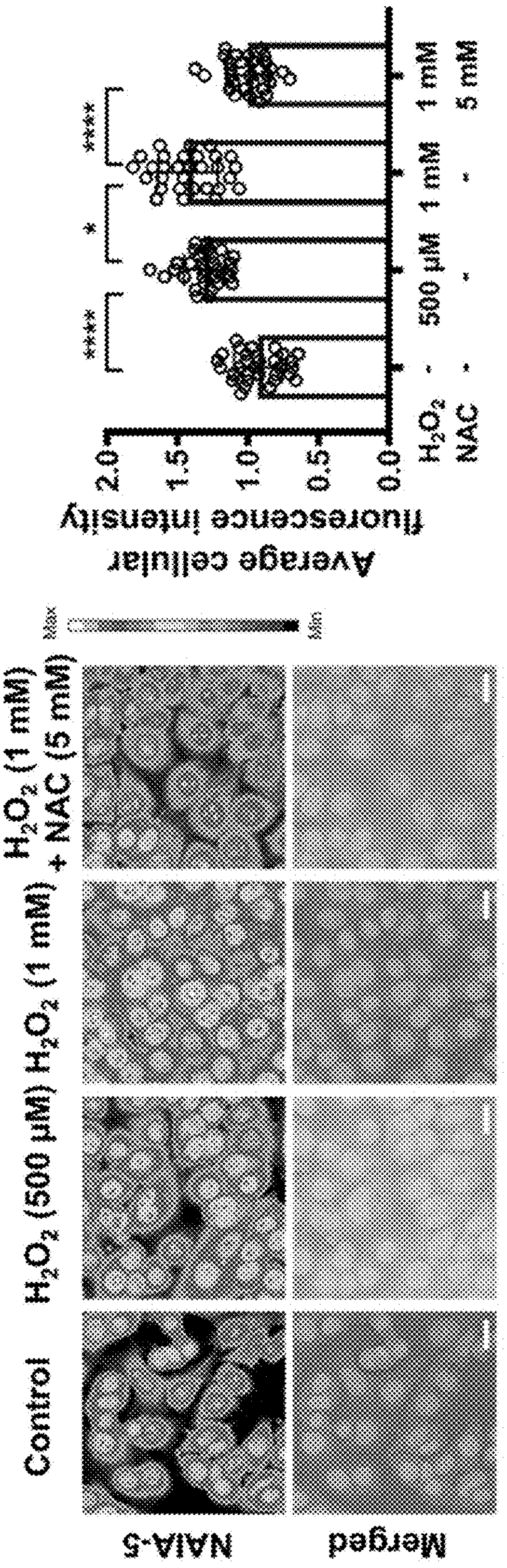

FIGS. 12A-12B. NAI/NAIA-5 couple allows successful labeling and imaging of oxidized thiols in cells under oxidative stress. (FIG. 12A) Schematic cartoon illustrating the working principle of NAI/NAIA-5 couple to label and image oxidized thiols. HepG2 cells were first pretreated by solvent vehicle or $H_2O_2$ (0.5 or 1 mM) in complete medium for 15 min. The cells were then washed with PBS and incubated with high concentration of NAI compound 3 (50 μM) in complete medium at 37° C. for 10 min to react with the free thiols. Then, the cells were washed with PBS, fixed by 4% paraformaldehyde and permeabilized by PBS with 0.5% Triton X-100. The fixed cells were treated with TCEP (1 mM) in PBS for 1 h to reduce oxidized thiols, followed by incubation with NAIA-5 (10 μM) in PBS to label the newly formed free thiols. The cells were washed with PBS, followed by CuAAC reactions with azide-fluor 545 (4 μM). After the reaction, the cells were washed and imaged in PBS by confocal fluorescence microscope. In this experimental setup oxidized thiols in cells under oxidative stress were labeled with Fluor 545 and show strong fluorescence, allowing direct visualization by confocal fluorescence imaging. (FIG. 12B) Confocal fluorescence microscopy images of HepG2 cells probed by NAI/NAIA-5 couple. Merged images are composed of images from brightfield, NAIA-5 and Hoechst channel. Cellular fluorescence intensity was determined by ImageJ. Quantified data were shown in average±SD from n=30 cells from 3 different biological replicates/group. Statistical significance is expressed as *p<0.05 and ****p<0.0001. Scale bar=20 μm.

Figure 13:
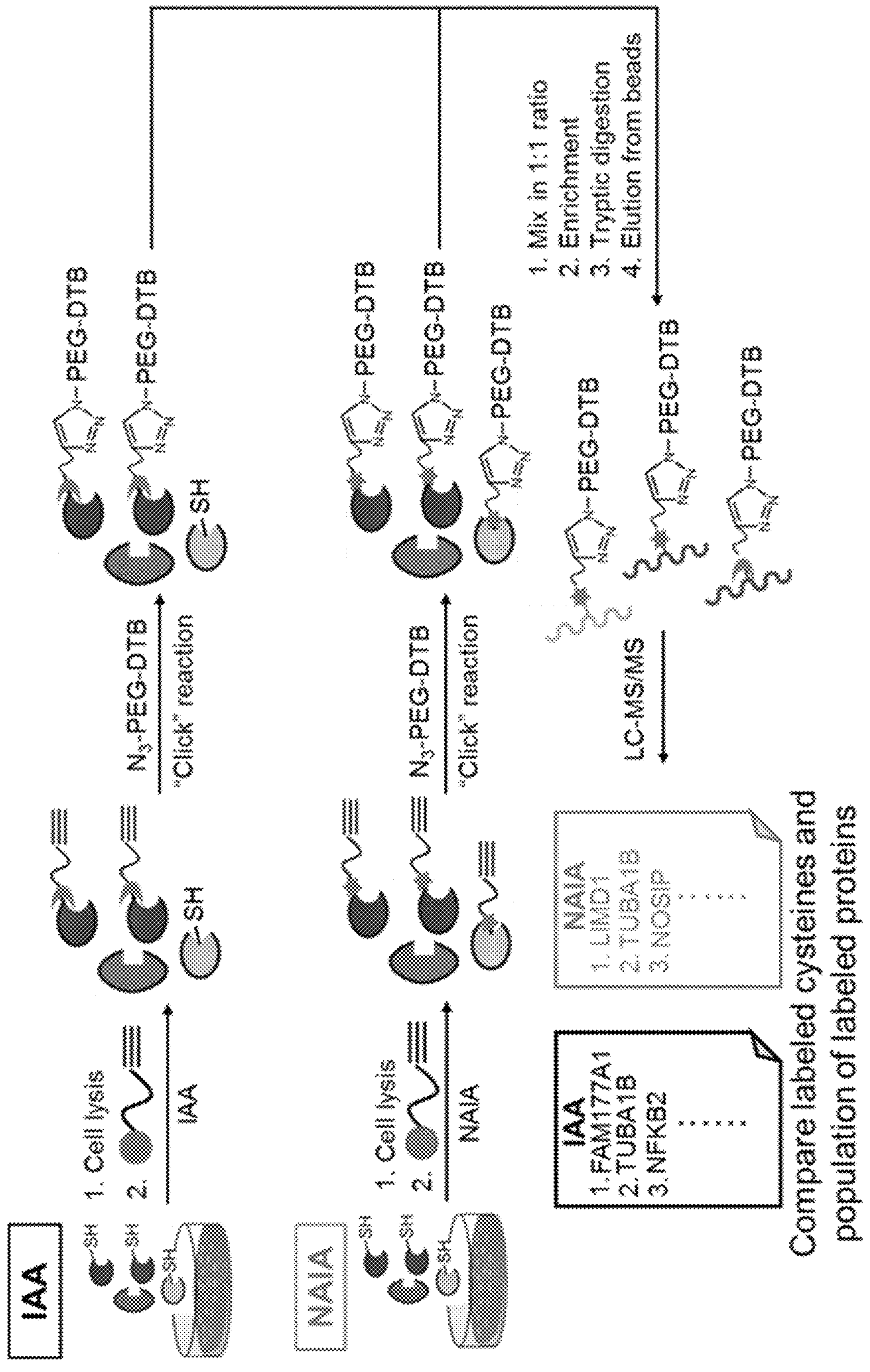

FIG. 13. Schematic cartoon illustrating workflow of MS-based chemoproteomics experiment to compare cysteine profiling by NAIA vs IAA. For cell lysate labeling experiment, cells in PBS were lysed by sonication and cell debris were removed by centrifugation. After protein assay and normalization, the cell lysates were incubated with NAIA-5 (10 μM) or IAA (10 μM) at room temperature for 1 h, followed by installation of desthiobiotin (DTB) onto the labeled proteins by CuAAC reaction with DTB-PEG-azide. Then NAIA-5 and IAA treated samples were mixed in 1:1 ratio, and subjected to streptavidin bead pull-down, cysteine carbamidomethylation, on-bead tryptic digestion and peptide elution from the bead using acetonitrile-water mixture. The eluted peptides were sent for LC-MS/MS analysis. The MS data were then searched for peptides with NAIA-5 and IAA specific modifications on Cys by MaxQuant. For live-cell labeling experiment, the cells were incubated with NAIA-5 (10 μM) or IAA (10 μM) in complete media for 2 h, washed with PBS and lysed by sonication. Then the samples were subjected to the same preparation procedure as the cell lysate labeling experiment.

Figure 14A:
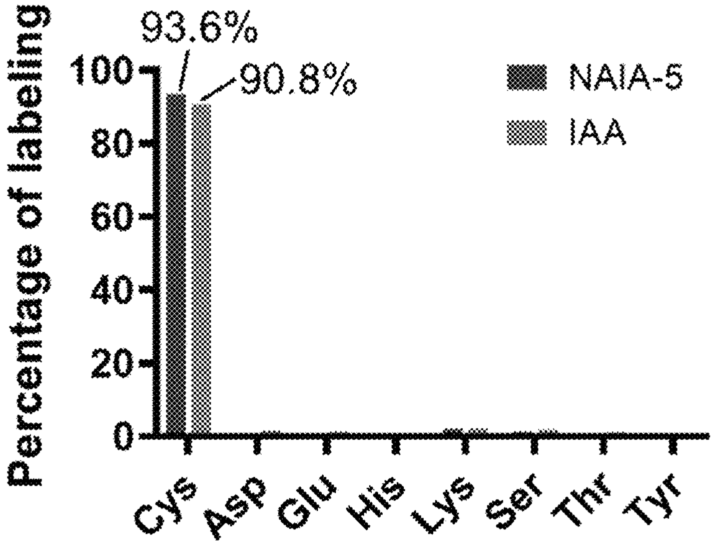
Figure 14B:
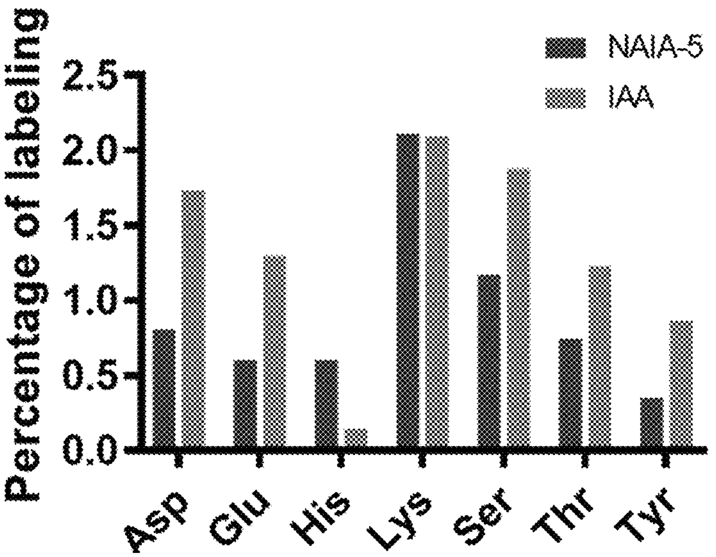

FIGS. 14A-14B. (FIG. 14A) Percentage of probe modifications on different amino acids in HepG2 cell lysates labeled by NAIA-5 and IAA respectively. (FIG. 14B) A plot without Cys for better visualization of the labeling on other amino acids.

FIGS. 15A-15E. LC-MS/MS-based chemoproteomics experiment with Multidimensional Protein Identification Technology (MudPIT) to investigate Cys profiling of 231MFP cell lysates by NAIA-4 and IAA at 100 μM which is the typical working dose of IAA. (FIGS. 15A-15B) Total number of probe-modified peptides and number of unique cysteines being identified in the MudPIT experiment. The two lower numbers of IAA indicate better labeling of much larger population of functional cysteines by NAIA-4. (FIG. 15C) Number of probe-modified proteins identified in the MudPIT experiment. (FIG. 15D) Analysis on probe-modified proteins in 231MFP cells by NAIA-4 and IAA, respectively, using DrugBank database, and analysis on the functions of these proteins by Gene Ontology database. (FIG. 15E) Gene Ontology analysis of the biological processes involved by the probe-modified proteins, with the top 20 unique processes regulated by NAIA-4 shown in the bar chart.

Figure 16:
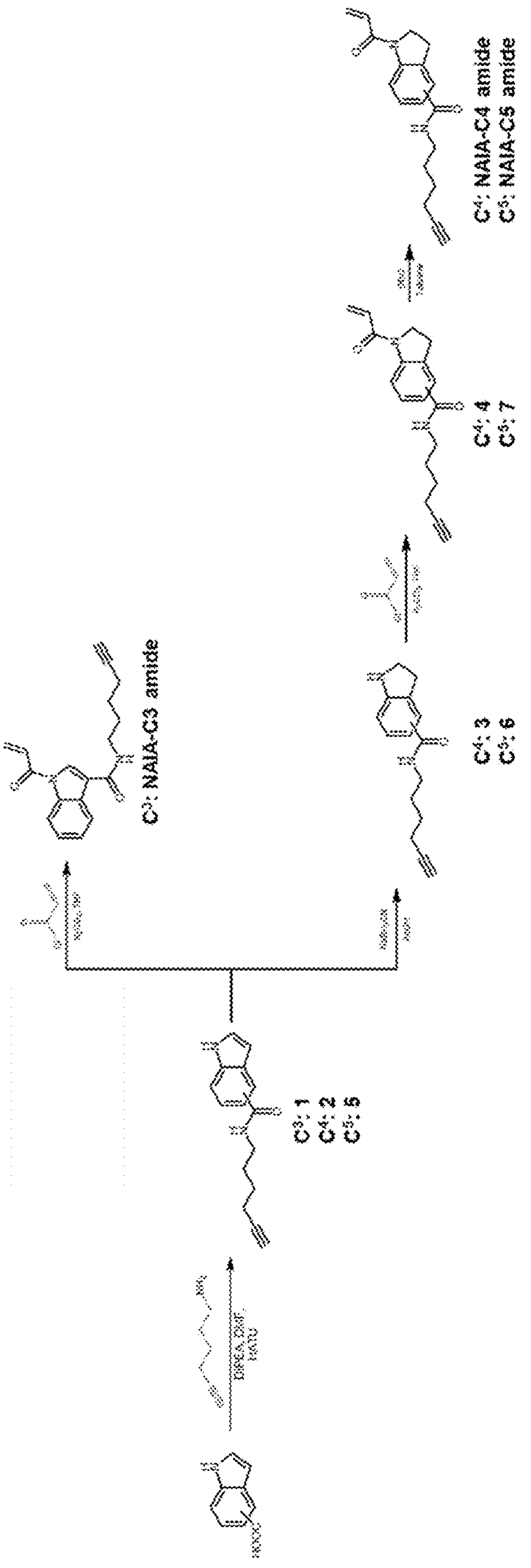

FIG. 16 Synthetic scheme for NAIA-C3-amide, NAIA-C4-amide and NAIA-C5-amide.

FIGS. 17A-17F (FIG. 17A) Chemical equation showing thiol-Michael addition of NAIA-C5-amide with N-acetyl-cysteine methyl ester (N-Ac-Cys-OMe), a N- and C-terminal protected cysteine, to form the adduct product. (FIG. 17B) NAIA-C5-amide (10 μM) in aqueous buffer solution (PBS-MeOH, 4:1, v/v) was incubated with N-Ac-Cys-OMe (250 μM). At indicated time intervals, an aliquot of the solution mixture was sent for LC-MS analysis. Selected ion chromatograms (SIC) at m/z=295 and 472, corresponding to the molecular ion of $[NAIA\text{-}C5\text{-}amide+H]^+$ and $[Adduct+H]^+$ respectively. The mass spectra (MS) at 5.09 and 4.80 min confirm the identity of NAIA-C5-amide and adduct. (FIG. 17C) Changes in Cys-reactive compound concentration over time upon incubation with N-Ac-Cys-OMe (250 μM); n=3. (FIG. 17D) Biomolecular rate constant of reactions between cysteine-reactive compounds and N-Ac-Cys-OMe. (FIG. 17E) Changes in level of NAIA-5 after incubation with amino acids (30 μM) for 30 min (n=3). (FIG. 17F) Stability of NAIA-5 in the aqueous buffer solution in the absence of Cys (n=3).

Figure 18A:
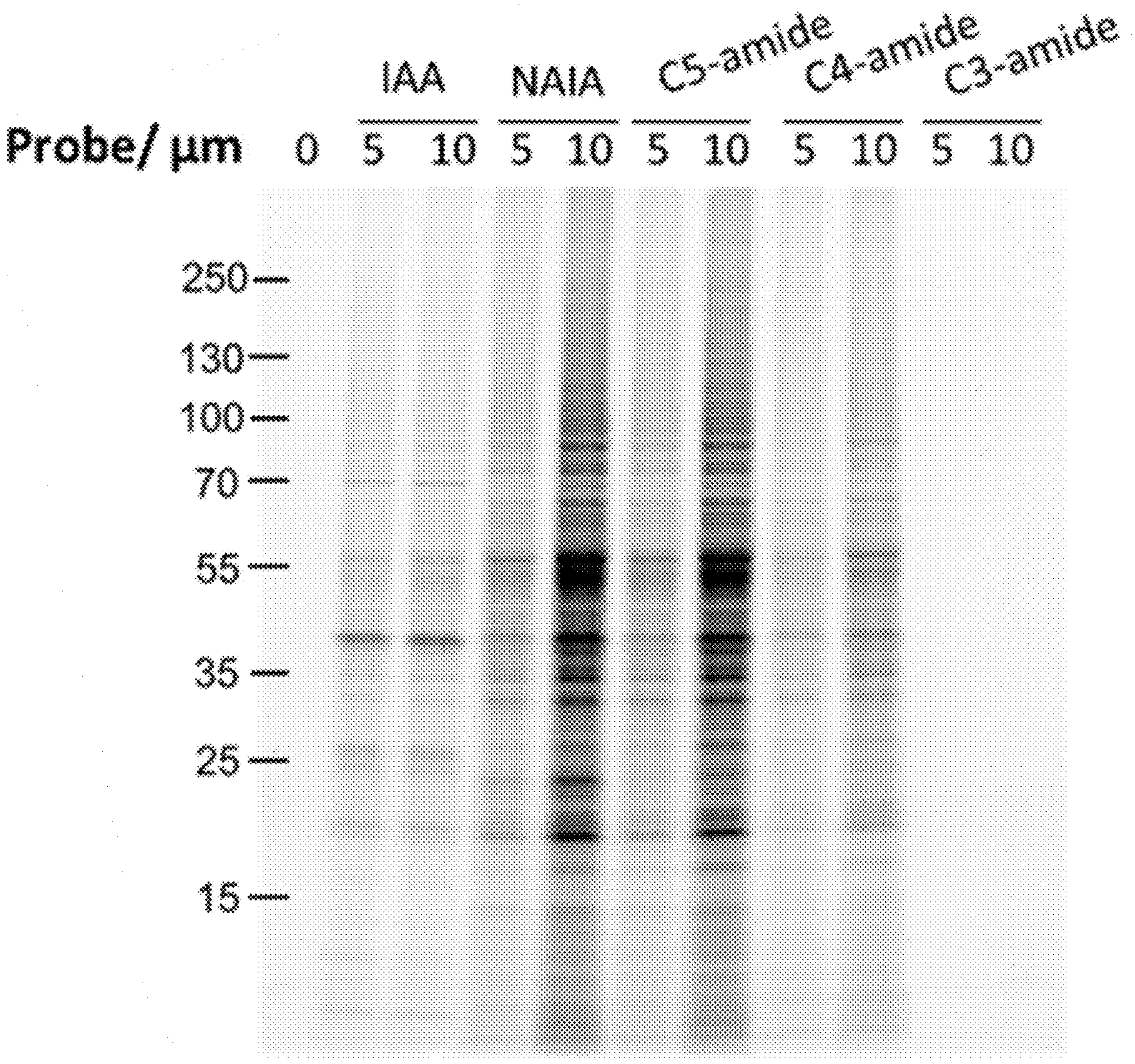
Figure 18B:
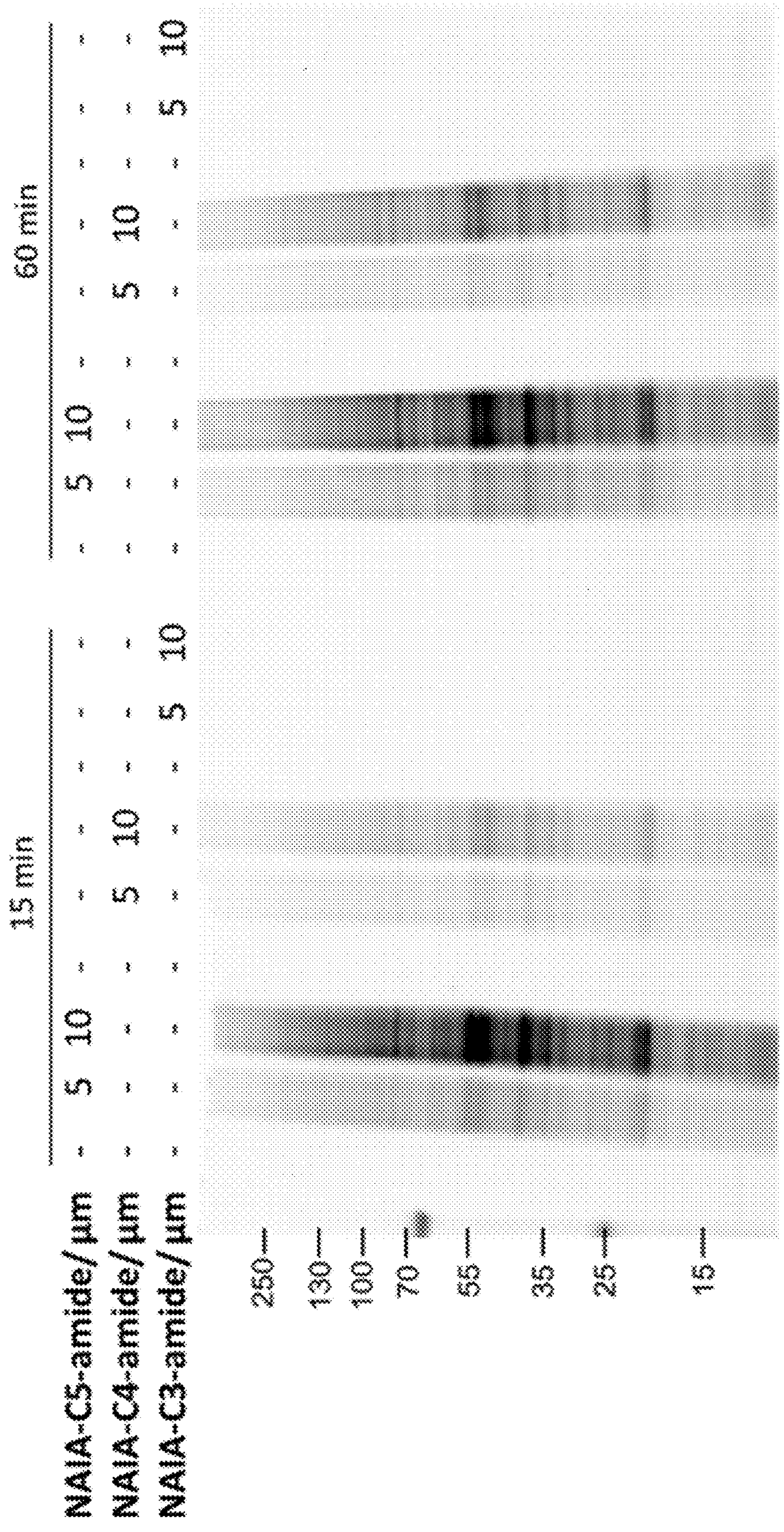

FIGS. 18A-18B Gel-based ABPP analysis of NAIA-amides, NAIA-5 and IAA on Cys labeling of HCT116 cell lysates in vitro. HCT116 cell lysates (100 μg) were incubated with the compounds at indicated concentrations and time intervals, following by CuAAC reaction with azide-fluor 545 (25 μM). The labeled proteins were then boiled with sampling buffer, and read out by in-gel fluorescence after SDS-PAGE.

Figure 19:
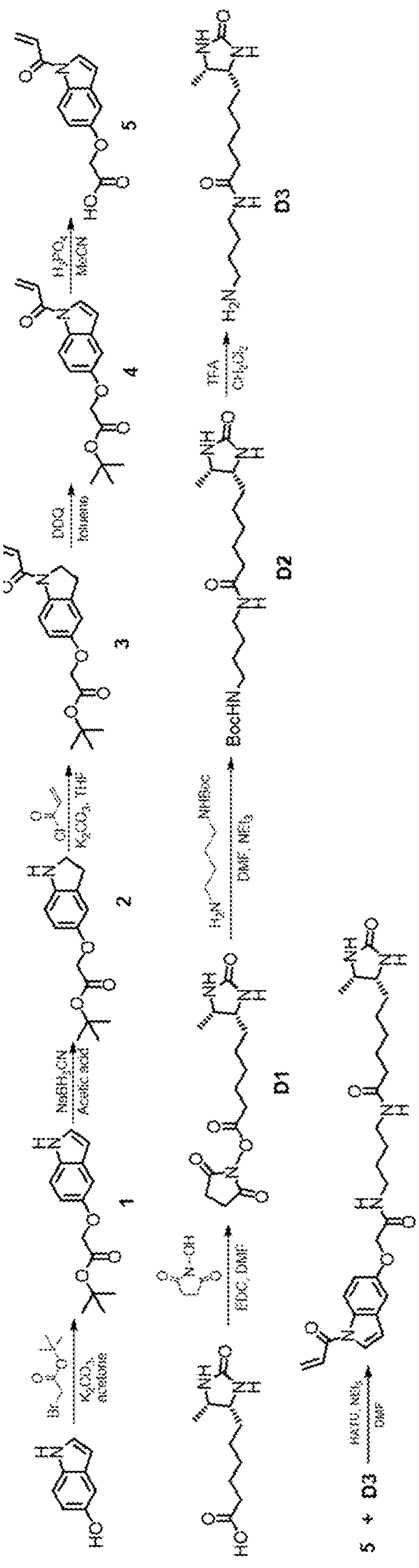

FIG. 19 Synthetic scheme of NAI-DTB

Figure 20:
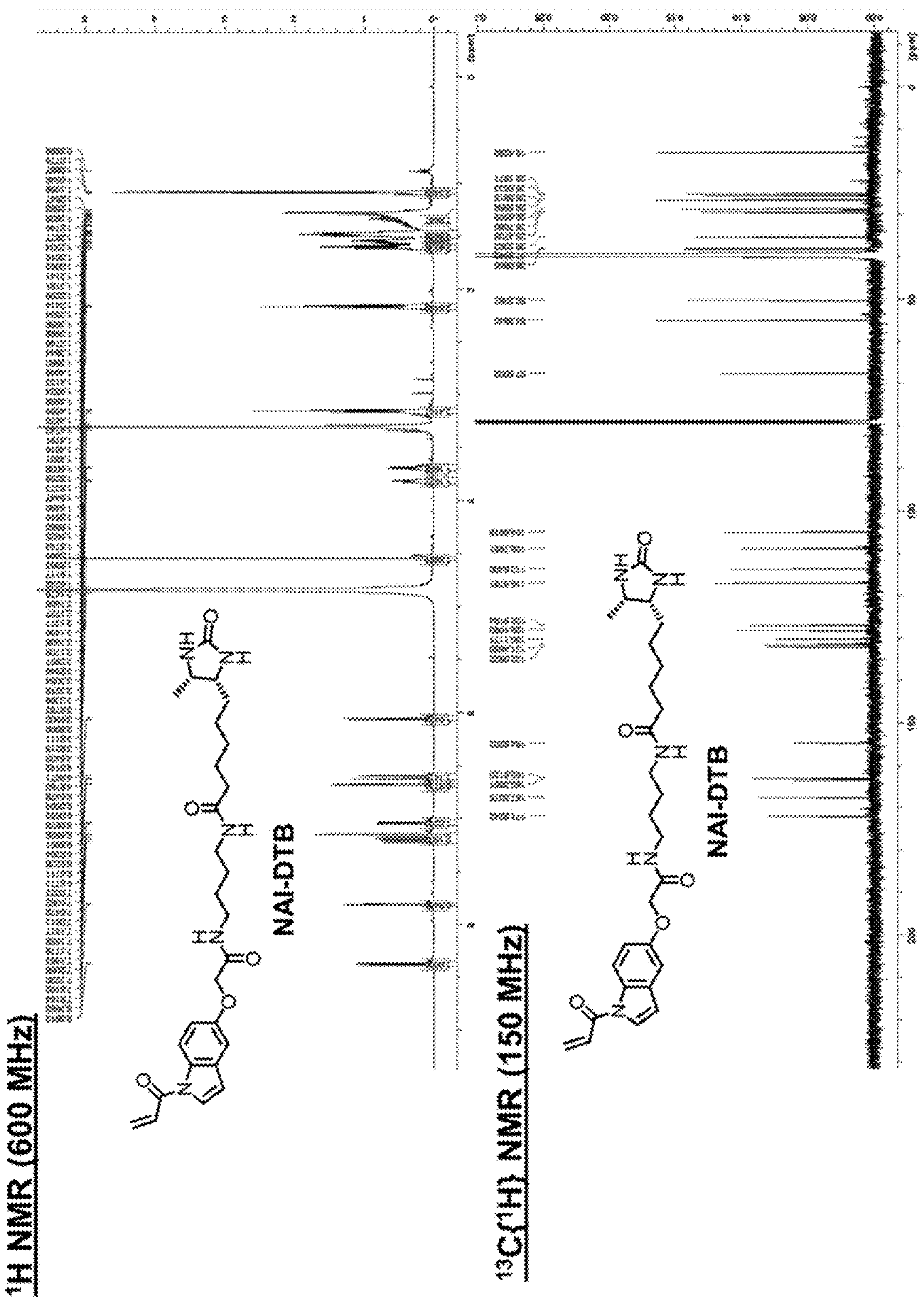

FIG. 20 $^1H$ NMR and $^{13}C\{^1H\}$ NMR spectra of NAI-DTB in CD30D and d6-DMSO respectively.

FIGS. 21A-21F (FIG. 21A) Schematic cartoon illustrating MS-based ABPP platform using NAI-DTB to identify differential ligandability of cysteines in normal and disease samples. (FIG. 21B) Investigation of Cys ligandability in MiHa (immortalized normal liver cells), HepG2 (liver cancer cells) and MHCC97L (invasive liver cancer cells). A number of ligandable Cys was found to show higher signals (>4 fold) in HepG2 cells only, MHCC97L cells only, or both HepG2 and MHCC97L cells as compared to the normal MiHa cells. (FIG. 21C) HTATSF1 is a representative protein with more than 1 ligandable Cys, and only one of them (Cys462) shows higher reactivity with statistically significance in HepG2 and MHCC97L cells, suggesting differential reactivity (not just expression levels) of ligandable Cys in these three cell lines. (FIG. 21D) Metastatic markers, (FIG. 21E) liver cancer driver and (FIG. 21F) poor prognostic marker for liver cancers with ligandable Cys have been identified by our MS-based ABPP experiment. All these Cys are uniquely profiled by NAI-DTB, and should be good targets for developing anti-metastatic and anti-cancer compounds. *p<0.05 vs MiHa; n.s.=Not significant vs MiHa.

FIGS. 22A-22E (FIG. 22A) Investigation of Cys ligandability in Lenvatinib-resistant and Lenvatinib-sensitive Huh7 cells. The Cys showing hyper-ligandability in the Lenvatinib-resistant cells were located at top right quadrant. (FIG. 22B) Differential reactivities of ligandable Cys were found in the Lenvatinib-resistant Huh7 cells (squares) as compared to the sensitive cells (circles), using RPL4 and MDH2 as representative examples. (FIG. 22C) Differential reactivity of ligandable Cys was also found in Lenvatinib-resistant PLC/PRF/5 cells (squares) as compared to the sensitive cells (circles). (FIG. 22D) 17 hyper-ligandable Cys were found in both the experiments on Huh7 pairs and PLC/PRF/5 pairs. (FIG. 22E) One of the 17 common targets, EEF1A2, shows hyper-ligandability on Cys326 but not Cys111 in Lenvatinib-resistant cells (squares) as compared to the sensitive cells (circles). *p<0.05, **p<0.01, n.s.=Not significant.

DETAILED DISCLOSURE OF THE INVENTION

Selected Definitions

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which depends in part on how the value is measured, i.e., the limitations of the measurement system. In the context of compositions containing amounts of ingredients where the terms "about" is used, these compositions contain the stated amount of the ingredient with a variation (error range) of 0-10% around the value (X±10%). In other contexts the term "about" provides a variation (error range) of 0-10% around a given value (X±10%). As is apparent, this variation represents a range that is up to 10% above or below a given value, for example, X±1%, X±2%, X±3%, X±4%, X±5%, X±6%, X±7%, X±8%, X±9%, or X±10%.

In the present disclosure, ranges are stated in shorthand to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are explicitly included.

As used herein, an "isolated" or "purified" compound is substantially free of other compounds. In certain embodiments, purified compounds are at least 60% by weight (dry weight) of the compound of interest. Preferably, the preparation is at least 75%, more preferably at least 90%, and most preferably at least 99%, by weight of the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

By "reduces" is meant a negative alteration of at least 1%, 5%, 10%, 25%, 50%, 75%, or 100%.

By "increases" is meant as a positive alteration of at least 1%, 5%, 10%, 25%, 50%, 75%, or 100%.

As used herein, the term "sample" refers to a sample comprising at least one cysteine residue, including in an peptide or protein. In one embodiment, a "biological sample," as that term is used herein, refers to a sample obtained from a subject, wherein the sample comprises at least one cysteine residue, including in an peptide or protein. While not necessary or required, the term "biological sample" is intended to encompass samples that are processed prior to assaying using the systems and methods described herein.

As used herein, the term "subject" refers to a plant or animal, particularly a human, from which a biological sample is obtained or derived from. The term "subject" as used herein encompasses both human and non-human animals. The term "non-human animals" includes all vertebrates, e.g., mammals, such as non-human primates, (particularly higher primates), sheep, dog, rodent (e.g., mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. In some embodiments, the term "subject" refers to a mammal, including, but not limited to, murines, simians, humans, felines, canines, equines, bovines, mammalian farm animals, mammalian sport animals, and mammalian pets.

As used herein, the terms "determining," "measuring," and "assessing," and "assaying" are used interchangeably and include both quantitative and qualitative determinations.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Preparation of Cysteine-Reactive Probes and Compositions Thereof

In certain embodiments, a novel class of cysteine-reactive probes can be synthesized. In certain embodiments, the probes can be used for proteome-wide cysteine imaging and profiling and imaging of thiol oxidative modifications. In certain embodiments, the probes are N-acryloylindoles (NAIs), including, for example, compounds according to formula (I), N-acryloylindole-alkynes (NAIAs), including, for example, compounds according to formula (II) (NAIA-4), formula (III) (NAIA-5), formula (IV), formula (V), formula (VI), formula (VII), formula (VIII), formula (IX), formula (X) (N-acryloylindoline 3a), formula (XI) (N-acryloylindoline 3b), formula (XII) (NAIA-C3 amide), formula (XIII) (NAIA-C4 amide), formula (XIV) (NAIA-C5 amide), and formula (XV) (NAI-DTB). NAIA-4, according to formula (II), and NAIA-5, according to formula (III), are isomers with different positions functionalized with "clickable" alkyne handles.

Formula (I)

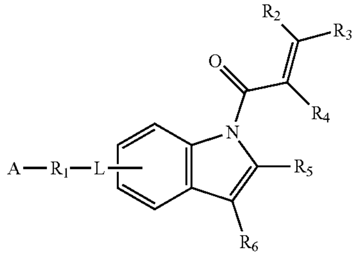

wherein,

A is an analytical handle, independently selected from an alkyne, azide, fluorophore, chromphore, biotin or desthiobiotin group;

$R_1$ is an independently substituted or unsubstituted alkyl, substituted or unsubstituted heteroalkyl, substituted or unsubstituted cycloalkyl, substituted or unsubstituted heterocycloalkyl, or substituted or unsubstituted heteroaryl;

L is an independently substituted or unsubstituted heteroalkylene, —O—, —OC(O)—, $—OCH_2C(O)NH—$, $—OCH_2C(O)O—$, —NH—, —NHC(O)—, —NHC(O)NH—, —NHC(O)O—, —C(O)O—, —S—, $—S(O)_2—$, or substituted or unsubstituted alkylene;

$R_2$, $R_3$, $R_4$, $R_5$ and $R_6$ are independently hydrogen, halogen, $—CX_3$, $—CRX_2$, $—CR_2X$, $—CR_3$, —CN, $—NO_2$, —C(O)NRR', —C(O)OR, —OCRR'R", $—OCXR_2$, $—OCX_2R$, —NRR', —NRC(O)OR', —SR, $—SO_2R$, $—SO_2NRR'$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl; and R, R' and R" are independently hydrogen, substituted or unsubstituted alkyl, substituted or unsubstituted heteroalkyl, substituted or unsubstituted cycloalkyl, substituted or unsubstituted heterocycloalkyl, or substituted or unsubstituted heteroaryl.

Formula (II)

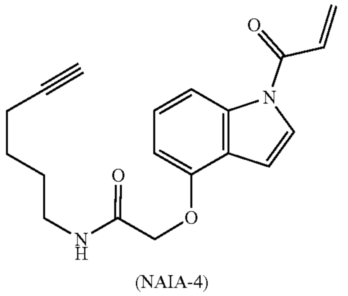

(NAIA-4)

-continued
Formula (III)
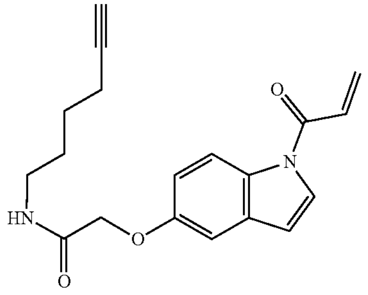
(NAIA-5)
Formula (IV)
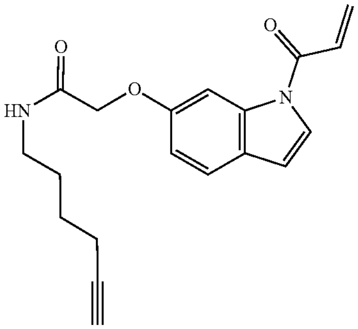
Formula (V)
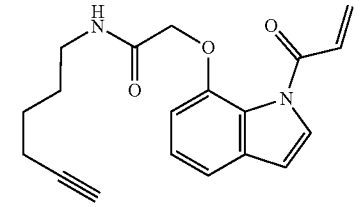
Formula (VI)
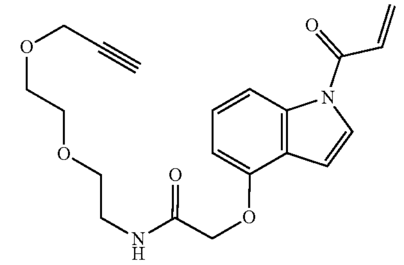
Formula (VII)
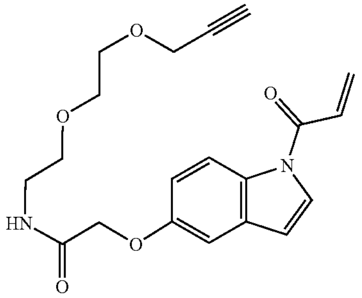
-continued
Formula (VIII)
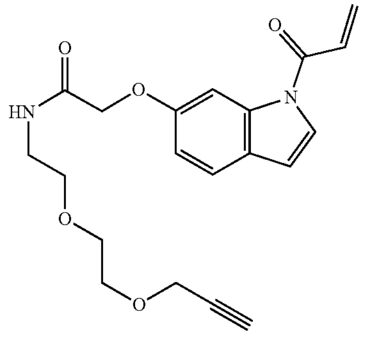
Formula (IX)
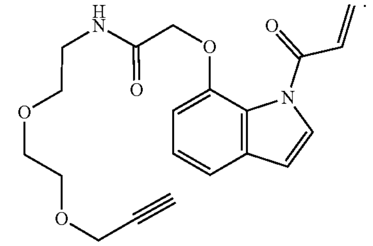
Formula (X)
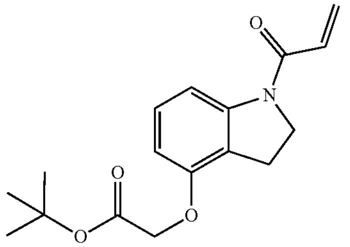
3a
Formula (XI)
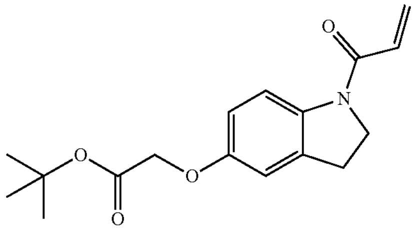
3b
Formula (XII)
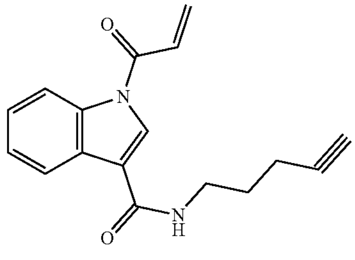

-continued

Formula (XIII)

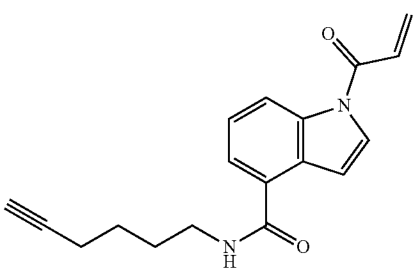

Formula (XIV)

or

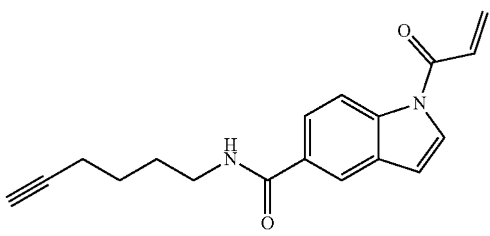

Formula (XV)

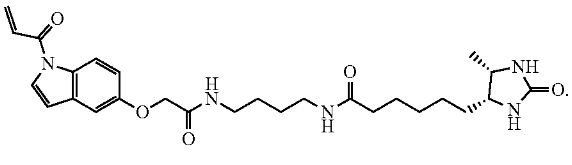

In certain embodiments, to synthesize the NAIA-4 or NAIA-5, $K_2CO_3$ (9.34 g, 67.6 mmol) can be added to 4-hydroxyindole or 5-hydroxyindole (3 g, 22.5 mmol) and tert-butyl bromoacetate (5 mL, 33.8 mmol) in acetone (100 mL) (FIG. 8A). The solution can be heated at 55° C. under reflux overnight. After the reaction, any undissolved solid can be filtered off, and the filtrate can be evaporated under reduced pressure. The crude product can be purified by column chromatography on silica gel using hexane/ethyl acetate (8:1, v/v) as eluent, yielding compound 1a as an off-white solid (3.27 g, 59%) ($^1$H NMR ($CDCl_3$, 400 MHz): δ=8.54 (1H, s), 7.00-7.13 (2H, m), 6.99 (1H, t, J=2.7 Hz), 6.72 (1H, t, J=2.2 Hz), 6.48 (1H, d, J=7.6 Hz), 4.74 (2H, s), 1.56 (9H, s); $^{13}$C{$^1$H} NMR ($CDCl_3$, 100 MHz) δ=168.7, 151.5, 137.5, 123.3,122.1,118.7, 105.6, 100.7, 99.5, 82.3, 66.1, 28.0; MS (ESI$^+$): m/z 248 ([M+H]$^+$) or compound 1b as an off-white solid (6.2 g, Quantitative) ($^1$H NMR ($CDCl_3$, 500 MHz): δ=8.12 (1H, s), 7.28-7.30 (1H, m), 7.19 (1H, t, J=2.8 Hz), 7.07 (1H, d, J=2.30 Hz), 6.93 (1H, dd, J=2.45 and 8.78 Hz), 6.47 (1H, s), 4.55 (2H, s), 1.50 (9H, s); MS (ESI$^+$): m/z 248 ([M+H]$^+$)).

Compound 1a (2.58 g, 10.4 mmol) or 1b (4.2 g, 17.0 mmol) can be dissolved in acetic acid (30 mL). $NaBH_3CN$ (1.96 g, 31.3 mmol or scaled according to compound 1b) can be added to the solution mixture portion wise at about 10° C. The solution mixture can then be stirred at about 10° C. for about 4 h, and then water can be added to quench the reaction. Any organic volatile was removed by evaporation under reduced pressure, and the aqueous layer can be extracted with dichloromethane. The dichloromethane layer can be washed by dilute NaOH solution and then saturated NaCl solution, dried by $MgSO_4$ and filtered. Volatile organic solvent can be evaporated under reduced pressure, and the crude product can be purified by column chromatography on silica gel using hexane/ethyl acetate (10:1, v/v) as eluent, yielding compound 2a as a white solid (2.02 g, 78%) ($^1$H NMR ($CDCl_3$, 400 MHz): δ=6.93 (1H, t, J=7.9 Hz), 6.29 (1H, d, J=7.7 Hz), 6.11 (1H, d, J=8.2 Hz), 4.50 (2H, s), 3.82 (1H, br), 3.52 (2H, t, J=8.5 Hz), 3.04 (2H, t, J=8.4 Hz), 1.48 (9H, s); $^{13}$C{$^1$H} NMR ($CDCl_3$, 100 MHz) δ=168.2, 154.7, 153.6, 128.3, 116.2, 103.6, 102.1, 81.9, 65.6, 47.3, 27.9, 26.8; MS (ESI$^+$): m/z 250 ([M+H]$^+$)) or compound 2b as a white solid (1.3 g, 30%) ($^1$H NMR ($CDCl_3$, 600 MHz): δ=6.77 (1H, s), 6.59 (2H, d, J=1.38 Hz), 4.23 (2H, s), 3.54 (2H, t, J=8.28 Hz), 3.00 (2H, t, J=8.1 Hz), 1.48 (9H, s)).

$K_2CO_3$ (2.24 g, 16.2 mmol) can be added to compound 2a (2.02 g, 8.1 mmol) or 2b (1.1 g, 4.4 mmol) in dry THF (40 mL). At about 0° C., acryloyl chloride (0.71 mL, 8.9 mmol or scaled down according to compound 2b) in dry THF (10 mL) can be added dropwise to the solution mixture with vigorous stirring. The solution mixture can be further stirred at about 0° C. for about 30 min, and then the reaction can be quenched by addition of water. Any organic volatile can be removed by evaporation under reduced pressure, and the aqueous layer can be extracted with ethyl acetate. The ethyl acetate layer was can be washed by saturated NaCl solution, dried by $MgSO_4$ and filtered. Volatile organic solvent can be evaporated under reduced pressure, and the crude product can be purified by column chromatography on silica gel using hexane/ethyl acetate (10:1, v/v) as eluent, yielding compound 3a as a white solid (2.16 g, 88%) ($^1$H NMR ($CDCl_3$, 300 MHz): δ=7.77 (1H, d, J=7.7 Hz), 6.95 (1H, t, J=8.2 Hz), 6.22-6.45 (3H, m), 5.58 (1H, dd, J=2.9 and 9.3 Hz), 4.36 (2H, s), 3.89-3.99 (2H, m), 2.96 (2H, t, J=8.3 Hz), 1.32 (9H, s); $^{13}$C{$^1$H} NMR ($CDCl_3$, 75 MHz) δ=170.5, 167.5, 163.3, 153.8, 144.1, 128.9, 128.4, 119.2, 110.7, 106.7, 81.7, 65.2, 48.1, 27.6, 24.6; MS (ESI$^+$): m/z 304 ([M+H]$^+$)) or compound 3b as a white solid (1.1 g, 82%) ($^1$H NMR ($CDCl_3$, 500 MHz): δ=8.21 (1H, d, J=8.80 Hz), 6.71-6.78 (2H, m), 6.46-70 (2H, m), 5.77 (1H, dd, J=2.00 and 9.78 Hz), 4.49 (2H, s), 4.16 (2H, t, J=8.35), 3.17 (2H, t, J=8.35 Hz), 1.48 (9H, s); MS (ESI$^+$): m/z 304 ([M+H]$^+$))

2,3-Dichloro-5,6-dicyano-p-benzoquinone (DDQ; 603 mg, 2.7 mmol) can be added to compound 3a (2.0 mmol) or 3b (1 g, 3.31 mmol) in dry toluene (15 mL), and the solution mixture can be heated to reflux with vigorous stirring overnight. The reaction mixture can be diluted by ethyl acetate and washed by water and saturated NaCl solution. The organic layer can be dried by $MgSO_4$, filtered and evaporated under reduced pressure. The crude product can be purified by column chromatography on silica gel using hexane/ethyl acetate (10:1, v/v) as eluent, yielding compound 4a as a white solid (560 mg, 93%) ($^1$H NMR ($CDCl_3$, 400 MHz): δ=8.13 (1H, d, J=8.3 Hz), 7.41 (1H, d, J=3.8 Hz), 7.24 (1H, t, J=8.1 Hz), 6.84-6.98 (2H, m), 6.57-6.68 (2H, m), 5.99 (1H, d, J=10.9 Hz), 4.64 (2H, s), 1.48 (9H, s); $^{13}$C{$^1$H} NMR ($CDCl_3$, 100 MHz) δ=168.0, 164.0, 151.1, 137.2, 132.1, 127.9, 125.9, 123.4, 121.1, 110.7, 106.5, 105.5, 82.4, 66.0, 28.1; MS (ESI$^+$): m/z 324 ([M+Na]$^+$)) or yielding 4b as a white solid (626.1 mg, 63%) ($^1$H NMR ($CDCl_3$, 600 MHz): δ=8.42 (1H, d, J=8.94 Hz), 7.50 (1H, d, J=3.78 Hz), 7.03 (1H, d, J=2.46 Hz), 6.99-7.01 (1H, m), 6.93-6.97 (1H, m), 6.67 (1H, dd, J=1.32 and 16.77 Hz), 6.60 (1H, d, J=3.6 Hz), 6.03 (1H, dd, J=1.38 and 10.44 Hz), 4.57 (2H, s), 1.49 (9H, s); MS (ESI$^+$): m/z 324 ([M+Na]$^+$)).

85% $H_3PO_4$ (1 mL) can be added to compound 4a (100 mg, 0.33 mmol) or 4b (84.6 mg, 0.28 mmol) in MeCN (1 mL). The solution mixture can be stiffed at room temperature overnight. The reaction can be quenched by the addition of water, and organic volatile can be removed by evaporation under reduced pressure. The aqueous layer can be extracted with ethyl acetate twice and the combined ethyl acetate fraction can be dried by $MgSO_4$ and filtered. Volatile organic solvent can be evaporated under reduced pressure, and the crude product can be purified by column chromatography on silica gel using dichloromethane/methanol (10:1, v/v) as eluent, yielding compound 5a as a white solid (80 mg, 98%) ($^1$H NMR ($CD_3O_D$, 400 MHz): δ=8.08 (1H, d, J=8.3 Hz), 7.72 (1H, d, J=3.9 Hz), 7.16-7.27 (2H, m), 6.90 (1H, d, J=3.9 Hz), 6.73 (1H, d, J=8.0 Hz), 6.62 (1H, dd, J=1.6 and 15.9 Hz), 6.06 (1H, dd, J=1.6 and 10.3 Hz), 4.79 (2H, s); MS ($ESI^-$): m/z 244 ($[M-H]^-$)) or yielding 5b as a white solid (48.5 mg, 70%) ($^1$H NMR (CD30D, 600 MHz): δ=8.26 (1H, d, J=9.06 Hz), 7.71 (1H, d, J=3.78 Hz), 7.09-7.13 (1H, m), 7.02 (1H, d, J=2.58 Hz), 6.89-6.91 (1H, m), 6.50-6.57 (2H, m), 5.96 (1H, dd, J=1.62 and 10.4 Hz), 4.60 (2H, s); MS ($ESI^-$): m/z 244 ($[M-H]^-$)).

HATU (48.2 mg, 0.13 mmol) can be added to compound 5a (30 mg, 0.12 mmol) or 5b (50.9 mg, 0.21 mmol) in dry DMF (2 mL) and the reaction mixture can be stirred at about room temperature for about 15 min. After that, hex-5-yn-1-amine (12.8 μL, 0.11 mmol or scaled up according to the amount of 5b) in dry DMF (1 mL) can be added to the solution mixture, followed by the addition of DIPEA (57.8 μL, 0.33 mmol or scaled up according to the amount of 5b). The solution can be stirred at room temperature overnight. The reaction can be then quenched by the addition of water. Any organic volatile can be removed by evaporation under reduced pressure, and the aqueous layer can be extracted with ethyl acetate twice. The combined ethyl acetate fraction can be washed by saturated NaCl solution, dried by $MgSO_4$ and filtered. Volatile organic solvent can be evaporated under reduced pressure, and the crude product can be purified by column chromatography on silica gel using dichloromethane/methanol (20:1, v/v) as eluent, yielding NAIA-4 as a white solid (25 mg, 70%) ($^1$H NMR ($CDCl_3$, 400 MHz): δ=8.18 (1H, d, J=8.4 Hz), 7.49 (1H, d, J=3.8 Hz), 7.30 (1H, t, J=8.2 Hz), 6.98 (1H, dd, J=10.4 and 16.0 Hz), 6.80 (1H, d, J=3.8 Hz), 6.67-6.74 (2H, m), 6.61 (1H, br), 6.08 (1H, dd, J=1.4 and 10.4 Hz), 4.65 (2H, s), 3.40 (2H, q, J=6.8 Hz), 2.22 (2H, dt, J=2.7 and 6.8 Hz), 1.95 (2H, t, J=2.6 Hz), 1.64-1.73 (2H, m), 1.50-1.59 (2H, m); $^{13}C\{^1H\}$ NMR ($CDCl_3$, 100 MHz) δ=168.3, 164.1, 150.4, 137.3, 132.6, 127.9, 126.3, 123.9, 120.9, 111.4, 106.2, 105.8, 84.0, 68.9, 68.0, 38.6, 28.7, 25.7, 18.2. HRMS (ESI) m/z $[M+Na]^+$ calcd for $C_{19}H_{20}N_2O_3Na$, 347.1366; found, 347.1367) or yielding NAIA-5 as a white solid (24.9 mg, 37%) ($^1$H NMR ($CDCl_3$, 600 MHz): δ=8.45 (1H, d, J=9.00 Hz), 7.53 (1H, d, J=3.72 Hz), 7.05 (1H, d, J=2.58 Hz), 7.01 (1H, dd, J=2.52 and 9.00 Hz), 6.96 (1H, dd, J=10.4 and 16.7 Hz), 6.68 (2H, dd, J=1.32 and 16.7 Hz), 6.62 (1H, d, J=3.72), 6.05 (1H, dd, J-1.32 and 5.25 Hz), 4.25 (2H, s), 3.39 (2H, q, J=6.9 Hz), 2.22 (2H, td, J=2.58 and 6.94 Hz), 1.95 (1H, t, J=2.64 Hz), 1.66-1.71 (2H, m), 1.54-1.58 (2H, m). $^{13}C\{^1H\}$ NMR ($CDCl_3$, 150 MHz) δ=168.3, 163.6, 154.2, 132.2, 131.7, 131.2, 127.6, 125.6, 118.0, 113.9, 109.2, 104.7, 83.9, 38.5, 28.6, 25.6, 18.1; MS ($ESI^+$): m/z 325 ($[M+H]^+$)).

In preferred embodiments, the compositions and methods according to the subject invention utilize a novel compound as a cysteine-reactive probe, such as, for example, NAIs or NAIAs. The NAI or NAIA compounds may be in a purified form. NAI or NAIA compounds may be added to compositions at concentrations of 0.01 to 99.99% by weight (wt %), preferably 50 to 99.99 wt %, and more preferably 90 to 99.99 wt %. In another embodiment, a purified NAI or NAIA compound may be in combination with an acceptable carrier, in that NAI or NAIA compound may be presented at concentrations of 0.001 to 50% (v/v), preferably, 0.01 to 50% (v/v).

Carriers and/or excipients according the subject invention can include any and all solvents, diluents, buffers (such as, e.g., neutral buffered saline, phosphate buffered saline, or optionally Tris-HCl, acetate or phosphate buffers), oil-in-water or water-in-oil emulsions, aqueous compositions with or without inclusion of organic co-solvents suitable for, e.g., IV use, solubilizers (e.g., Polysorbate 65, Polysorbate 80), colloids, dispersion media, vehicles, fillers, chelating agents (e.g., EDTA or glutathione), amino acids (e.g., glycine), proteins, disintegrants, binders, lubricants, wetting agents, emulsifiers, sweeteners, colorants, flavorings, aromatizers, thickeners (e.g. carbomer, gelatin, or sodium alginate), coatings, preservatives (e.g., Thimerosal, benzyl alcohol, polyquaterium), antioxidants (e.g., ascorbic acid, sodium metabisulfite), tonicity controlling agents, absorption delaying agents, adjuvants, bulking agents (e.g., lactose, mannitol) and the like. Except for any conventional media or agent that is incompatible with the target composition, carrier or excipient use in the subject compositions may be contemplated.

Methods of Using Compounds of the Subject Invention

In certain embodiments, the subject invention provides methods for the detection of cysteine residues by novel compounds and compositions thereof. Applications of these compounds and compositions thereof for the detection of cysteine residues are also presented.

In certain embodiments, any sample can be tested using the methods and compounds described herein, provided that the sample comprises at least one cysteine residue. The term "biological sample" can refer to any sample containing a cysteine residue, such as, for example, blood, plasma, serum, urine, gastrointestinal secretions, homogenates of tissues or tumors, circulating cells and cell particles (e.g., circulating tumor cells), synovial fluid, feces, saliva, sputum, cyst fluid, amniotic fluid, cerebrospinal fluid, peritoneal fluid, lung lavage fluid, semen, lymphatic fluid, tears, prostate fluid, cell culture media, or cellular lysates. A sample can also be obtained from an environmental source, such as water sample obtained from a lake or other body of water, a liquid sample obtained from a food source, or a plant sample.

In certain embodiments, the compounds of the subject invention can be used to image, detect, or assay cysteine residues, such as, in cell lysates and live cells. Through delocalization of x electrons from the acrylamide warhead over the whole indole scaffold, this significantly increases electrophilicity of the acrylamide on NAIAs and hence activates it for fast and selective thiol-Michael addition reaction with nucleophilic cysteine.

In certain embodiments, NAIAs, including, for example, NAIA-4 and NAIA-5, can be utilized to profile functional cysteines in samples, such as, for example, cell lysates and live cells. In certain embodiments, NAIAs can label unique functional cysteines. The identity of these new functional cysteines can be determined by MS-based ABPP experiments, and a number of these cysteines can be found on proteins associated with gene expression and regulations, such as, for example, transcription factors. NAIAs can be used in competitive binding experiments with a covalent ligand library so that new drug compounds targeting these proteins, which could have good therapeutic values but remain currently undrugged, can be developed. In addition, NAIAs can work at low working concentrations, such as, about 10 μM, as well as with both simple experimental setup (using short LC gradient) and MudPIT for proteome-wide cysteine profiling.

In certain embodiments, NAIAs can be used in labeling functional cysteines in cell lysates and live cells. In certain embodiments, samples, such as, for example, cell lysates (100 μg) can be first incubated with an NAIA at a concentration of about 0.1 μM to about 100 μM, about 1 μM to about 10 μM, or about 5 μM for about 1 min to about 4 hours, about 10 mins to about 2 hours, about 15 mins to about 1.5 h, about 30 mins to about 1 h, or about 1 h at about room temperature, and then reacted with a labeling molecule, such as, for example, azide-fluor 545, through, for example, copper(I)-catalyzed alkyne-azide cycloaddition (CuAAC). After the reaction, the protein mixture can be resolved by sodium dodecyl sulphate-polyacrylamide gel electrophoresis (SDS-PAGE) and in-gel fluorescence can be measured.

In certain embodiments, samples, such as, for example, live cells, can be incubated with NAIA in complete medium at a concentration of about 0.1 μM to about 100 μM, about 1 μM to about 10 μM, or about 5 μM for about 1 min to about 4 hours, about 10 mins to about 2 hours, about 15 mins to about 1.5 h, about 30 mins to about 1 h, or about 1 h at about room temperature. The treated cells can be washed and lysed in PBS by probe sonication. After protein assay and normalization, the protein samples can be reacted with a labeling molecule, such as, for example, azide-containing fluorophores such as azide-fluor 545, azide-fluorescein, azide-rhodamine, azide-cyanines, through, for example, copper(I)-catalyzed alkyne-azide cycloaddition (CuAAC). After the reaction, the protein mixture can be resolved by sodium dodecyl sulphate-polyacrylamide gel electrophoresis (SDS-PAGE) and in-gel fluorescence can be measured.

In certain embodiments, NAI/NAIAs can be used for imaging dynamic changes in cellular thiol activity through oxidative modifications. The fast thiol reaction kinetics and good cellular penetration allow NAI/NAIA to capture and image oxidized thiols in cells by confocal fluorescence microscopy. In certain embodiments, NAI/NAIAs can be used to determine the spatial information of modified thiols in cells under different stimulations or in disease-relevant conditions.

In certain embodiments, NAIs/NAIAs can be used to trap cellular thiols in live cells that can allow for identification of cysteine oxidative modifications. In certain embodiments, samples, such as, for example, HepG2 cells, can be pretreated with solvent vehicles, $H_2O_2$, or $H_2O_2$+N-acetyl cysteine (NAC), in which NAC can scavenge $H_2O_2$ and relieve the oxidative stress in the HepG2 cells. After the pretreatment, the cells can be incubated with NAIs/NAIAs 0.1 μM to about 100 μM, about 1 μM to about 50 μM, or about 50 μM for about 1 min to about 4 hours, about 10 mins to about 2 hours, about 10 mins to about 1.5 h, about 00 mins to about 1 h, or about 10 min to ligand and snap-shot free cellular thiols. The cells can then be fixed, permeabilized, and, optionally, reduced by TCEP to reduce thiols with reversible oxidative modifications back to the free thiol form. In certain embodiments, the cells can be stained with a labeling molecule, such as, for example, azide-containing fluorophores such as azide-fluor 545, azide-fluorescein, azide-rhodamine, azide-cyanines, through, for example, a CuAAC reaction, incubated with a nucleic acid stain such as, for example, Hoechst 33342, DAPI and propidium iodide, and imaged.

In certain embodiments, functional cysteines can be labeled by NAIs/NAIAs using MS-based chemoproteomics. In certain embodiments, samples, including, for example, cell lysates, can be incubated in PBS with NAIs/NAIAs at a concentration of about 0.1 μM to about 100 μM, about 1 μM to about 10 μM, or about 10 μM for about 1 min to about 4 hours, about 10 mins to about 2 hours, about 15 mins to about 1.5 h, about 30 mins to about 1 h, or about 1 h at room temperature, followed by CuAAC reaction with desthiobiotin (DTB)-azide or biotin-azide to install a DTB/biotin moiety onto the labeled proteins by NAIs/NAIAs. After processing to remove excess reagents for the CuAAC reaction, such as, for example, using acetone precipitation and methanol washing, the NAI/NAIA-treated sample can be subjected to streptavidin enrichment, cysteine carbamidomethylation, and on-bead tryptic digestion. After washing out the tryptic digests, the DTB-labeled peptides can be eluted from the streptavidin bead using acetonitrile-water mixture (1:1, v/v) with 0.1% formic acid. These eluted peptides can be sent for a simple LC-MS/MS analysis using a short LC gradient of 2 h, and the MS data can be searched for NAIs/NAIAs specific modifications on Cys by MaxQuant to identify peptides labeled by NAIs/NAIAs.

In certain embodiments, NAIs/NAIAs can be used for coupling with MudPIT for cysteine profiling. In certain embodiments, samples, including, for example, cell lysates can be incubated with NAIs/NAIAs at a concentration of about 0.1 μM to about 100 μM, about 1 μM to about 10 μM, or about 10 μM for about 1 min to about 4 hours, about 10 mins to about 2 hours, about 15 mins to about 1.5 h, about 30 mins to about 1 h, or about 1 h at room temperature, and then subjected to sample preparation, including, for example, a CuAAC reaction with desthiobiotin (DTB)-azide or biotin-azide to install a DTB/biotin moiety onto the labeled proteins by NAIs/NAIAs. After processing to remove excess reagents for the CuAAC reaction, such as, for example, using acetone precipitation and methanol washing, the NAI/NAIA-treated sample can be subjected to streptavidin enrichment, cysteine carbamidomethylation, and on-bead tryptic digestion. After washing out the tryptic digests, the DTB-labeled peptides can be eluted from the streptavidin bead using acetonitrile-water mixture (1:1, v/v) with 0.1% formic acid. The eluted peptides were then loaded onto laser-pulled column packed with C18 and strong-cation exchange (SCX) resin and analyzed by LC-MS/MS in a five-step of chromatography run as reported previously.[5,6]

In certain embodiments, NAIs/NAIAs can be used for profiling functional cysteines in live cells. In certain embodiments, the live cells can be incubated with NAIs/NAIAs in complete medium at a concentration of about 0.1 μM to about 100 μM, about 1 μM to about 10 μM, or about 10 μM for about 1 min to about 4 hours, about 10 mins to about 2 hours, about 15 mins to about 1.5 h, about 30 mins to about 1 h, or about 1 h at room temperature. The treated cells can be washed and lysed in PBS by sonication, followed by protein assay and normalization. The samples were then subjected to preparation, including, for example, a CuAAC reaction with desthiobiotin (DTB)-azide or biotin-azide to install a DTB/biotin moiety onto the labeled proteins by NAIs/NAIAs. After processing to remove excess reagents for the CuAAC reaction, such as, for example, using acetone precipitation and methanol washing, the NAI/NAIA-treated sample can be subjected to streptavidin enrichment, cysteine carbamidomethylation, and on-bead tryptic digestion. After washing out the tryptic digests, the DTB-labeled peptides can be eluted from the streptavidin bead using acetonitrile-water mixture (1:1, v/v) with 0.1% formic acid. The eluted peptides were then loaded onto laser-pulled column packed with C18 and strong-cation exchange (SCX) resin and analyzed by LC-MS/MS in a five-step of chromatography run as reported previously.[5,6]

Materials and Methods

Materials and Reagents for Chemical Synthesis 4-hydroxyindole, 5-hydroxyindole, triphenylphosphine and sodium cyanoborohydride were purchased from AK Scientific. Acryloyl chloride, sodium hydride (60% dispersion in mineral oil), acetic acid, 4,5-dichloro-3,6-dioxo-1,4-cyclohexadiene-1,2-dicarbonitrile (DDQ), tert-butyl bromoacetate, potassium carbonate and N,N-diisopropylethylamine (DIPEA) were purchased from Sigma-Aldrich (St. Louis, MO). Hex-5-yn-1-amine was purchased from Combi-Blocks (San Diego, CA). 85% Phosphoric acid was purchased from Alfa Aesar (Haverhill, MA). All other reagents were of analytical grade and were used without further purification. MilliQ water was used in all experiments unless otherwise stated.

Materials and Reagents for Biological Experiments

Azide-fluor 545, iodoacetamide, copper(II) sulfate pentahydrate, Tris(2-carboxyethyl)phosphine hydrochloride (TCEP) and DPBS were purchased from Sigma-Aldrich. N-Hex-5-ynyl-2-iodoacetamide was from Chess Fine Organics. Tris[(1-benzyl-1H-1,2,3-triazol-4-yl)methyl] amine (TBTA) was from Cayman Chemical. WST-8 was from Abcam (228554). FBS (35-015-CV) and 0.25% Trypsin-EDTA (1×; 25200-056) were from Gibco. DMEM (10-013-CV), GluatMax (100×; 25030-081), HyClone™ Leibovitz L-15 Media (SH30525.01) and Pierce™ Streptavidin Agarose beads (20349) were from Thermo Fisher Scientific. Sequencing grade modified trypsin (V51111) and GSH/GSSG-Glo™ Assay kit (V6611) were from Promega. N-Acetyl-L-cysteine methyl ester (9424AL) and N-acetyl-L-aspartic acid (U003) were from AK Scientific. Ac-Glu-OMe (QB-0580) and Ac-Tyr-OMe·$H_2O$ (SS-4784) were from Combi-Blocks. N-Acetyl-L-histidine was from Enamine LLC. N-Fmoc-L-proline (47636) was from Sigma Aldrich.

Physical Measurements and Instrumentation $^1$H NMR and $^{13}$C{$^1$H} spectra were collected at 25° C. on Bruker AVB-400, AVQ-400 and AV-300 at the College of Chemistry NMR Facility at the University of California, Berkeley, or on Bruker AVANCE NEO 600 MHz spectrometer at the Department of Chemistry at the University of Hong Kong. All chemical shifts are reported in the standard δ notation of parts per million relative to residual solvent peak as an internal reference. Splitting patterns are indicated as follows: br, broad; s, singlet; d, doublet; t, triplet; m, multiplet; dd, doublet of doublets; tt, triplet of triplets. High-resolution mass spectra were collected at the QB3/Chemistry Mass Spectrometry Facility at the University of California, Berkeley. UV-Vis absorption and fluorescence from microplates were recorded on SpectraMax i3 (Molecular Devices) or on Perkin Elmer Victor 3 (Molecular Devices). In-gel fluorescence images were recorded on ChemiDoc MP Gel Imaging system (Bio-Rad). Reaction kinetics of cysteine-reactive compounds with amino acids in aqueous buffer solution were measured by liquid chromatography-tandem mass spectrometry on a Waters Autopurification System using a SunFire C18 HPLC column (50×4.6 mm with 5 μm diameter particles, Waters), or an Agilent 6430 QQQ using a Luna reverse-phase C5 column (50×4.6 mm with 5 mm diameter particles, Phenomenex). Confocal microscopic images were recorded on a Zeiss laser scanning microscope 880 with a 20× air objective lens using ZEN 2.3 (Black Version) software (Carl Zeiss) with 3× magnification zoom-in.

Cell Culture

The 231MFP cells were obtained from B. Cravatt and were generated from explanted tumor xenografts of MDA-MB-231 cells as previously described.[76] They were cultured in L-15 medium containing 10% FBS and maintained at 37° C. with 0% $CO_2$ and were subcultured when 80% confluence was reached. HepG2 cells were cultured in DMEM medium containing 10% FBS and 1% PS and maintained at 37° C. with 5% $CO_2$ and were subcultured when 80% confluence was reached.

Reaction Kinetics of Cysteine-Reactive Compounds with N-Acetyl-L-Cysteine Methyl Ester Stock solution of cysteine-reactive compound in DMSO was diluted by PBS/MeOH solution mixture (4:1, v/v; 500 μL), reaching final concentration of 10 μM. Stock solution of N-acetyl-L-cysteine methyl ester in DMSO was then freshly prepared, and added to the compound solution at final concentration of 250 μM. The solution mixture was incubated at room temperature, and at predetermined time intervals, an aliquot of the reaction mixture (10 μL) was sent for LC-MS analysis on Waters Autopurification System using a SunFire C18 HPLC column (50×4.6 mm with 5 μm diameter particles, Waters). Separation was achieved by gradient elution from 5% to 100% MeCN in water (constant 0.1 vol % formic acid) over 4 min, isocratic elution with 100% MeCN (with 0.1 vol % formic acid) from 4 to 8 min, and returning to 5% MeCN in water (with 0.1 vol % formic acid) and equilibrated for 2 min. Selected ion chromatograms, with m/z corresponding to the molecular ion of the compound and/or the adduct, were extracted and the data was analyzed using MassLynx™ software by calculating the area under the curve. The peak area was then calibrated to concentration of the compound/adduct by a set of solution mixtures containing known concentrations of the compound/adduct.

Selectivity of NAI for Reacting with Cys Over Other Amino Acids

Stock solution of NAIA-4 and NAIA-5, respectively, in DMSO was diluted by PBS/MeOH solution mixture (4:1, v/v; 500 μL), reaching final concentration of 10 μM. Stock solution of amino acid in DMSO was then freshly prepared, and added to the compound solution at final concentration of 30 μM. The solution mixture was incubated at room temperature for 30 min. After that, an aliquot of the reaction mixture (10 μL) was sent for LC-MS analysis. Selected ion chromatograms, with m/z=325 corresponding to $[NAIA\text{-}4+H]^+$ or $[NAIA\text{-}5+H]^+$, were extracted and analyzed by integrating the area under curve. Significant decreases in NAIA-4 and NAIA-5 levels were only found in the solution mixture with N-acetyl-L-cysteine methyl ester, indicating the high selectivity of NAIs toward reactions with Cys.

Stability of NAIA-5 in Aqueous Buffer Solution Over Time

NAIA-5 (10 μM) was dissolved in PBS/MeOH solution mixture (4:1, v/v; 500 μL) and stay at room temperature. At predetermined time intervals, an aliquot of the reaction mixture (10 μL) was sent for LC-MS analysis on Waters Autopurification System using a SunFire C18 HPLC column (50×4.6 mm with 5 μm diameter particles, Waters). Separation was achieved by gradient elution from 5% to 100% MeCN in water (constant 0.1 vol % formic acid) over 4 min, isocratic elution with 100% MeCN (with 0.1 vol % formic acid) from 4 to 8 min and returning to 5% MeCN in water (with 0.1 vol % formic acid) and equilibrated for 2 min. Selected ion chromatograms, with m/z=325 corresponding to $[NAIA\text{-}5+H]^+$, were extracted and analyzed by integrating the area under curve. No significant changes in NAIA-5 level in the aqueous buffer solution over time was found, suggesting the high stability of NAIA-5 in the aqueous buffer solution.

In-Gel Fluorescence for Visualizing Cys Labeling by NAIAs and IAA In Vitro

HepG2 or 231MFP cells were lysed by probe sonication in DPBS, and cell debris were removed by centrifugation at 1,000 g for 5 min. Protein concentration of the lysates was determined by bicinchoninic acid (BCA) assay, and the lysates were then diluted to 2 mg/mL by DPBS. 50 μL of the lysates were incubated with indicated concentrations of NAIA-4, NAIA-5 or IAA for indicated time interval at room temperature. A master mix for CuAAC were prepared from azide-fluor 545 (5 mM), copper(II) sulfate (9.5 mM), TBTA (1 mM) and freshly prepared TCEP (50 mM) and added to the lysates with the final concentrations of azide-fluor 545, copper(II) sulfate, TBTA and TCEP in the solution mixture at 25 μM, 1 mM, 100 μM and 1 mM respectively. The solution was incubated in dark at room temperature with shaking for 1 h, and then the reaction was quenched with 4× reducing Laemmli SDS sample loading buffer (Alfa Aesar) and heated at 90° C. for 5 min. Samples were then separated by molecular weight on precast 4-20% TGX gels (Thermo Scientific) and scanned by ChemiDoc MP (Bio-Rad Laboratories, Inc) for measuring in-gel fluorescence. After that, the gel was washed twice by MilliQ water, and then incubated with SimplyBlue™ SafeStain (ThermoFisher Scientific; LC6060) for 1 h with gentle shaking. The staining solution was discarded, and the gel was washed with MilliQ water for 1 h with gentle shaking, replaced with new MilliQ water and washed again for 1 h. The gel was then scanned by ChemiDoc MP for imaging the blue staining.

In-Gel Fluorescence for Visualizing Cys Labeling by NAIAs and IAA in Live Cells

231MFP or HepG2 cells were grown in 10-cm plates in complete medium. At ca. 80% confluency, the cells were treated with DMSO solvent control, NAIA-4, NAIA-5, or IAA at indicated concentrations in complete medium for indicated time interval. The cells were then washed by DPBS and lysed by probe sonication in DPBS. Cell debris were removed by centrifugation at 1,000 g for 5 min. Protein concentration of the lysates was determined by BCA assay, and the lysates were diluted to 2 mg/mL by DPBS. 50 μL of the lysates were labeled with azide-fluor 545 by CuAAC according to the procedures described above. The samples were then added with 4× reducing Laemmli SDS sample loading buffer, boiled at 90° C. for 5 min, and separated by molecular weight on precast 4-20% TGX gels and scanned by ChemiDoc MP for measuring in-gel fluorescence. After that, the gel was stained with SimplyBlue™ SafeStain as described above, washed and scanned by ChemiDoc MP for imaging the blue staining.

WST-8 Cell Viability Assay of Cells Treated with NAIA-4 or IAA

231MFP cells were plated on 96-well plates (Corning, 3904) at 30,000 cells per well and allowed to grow in complete medium overnight. The cells were then incubated with DMSO solvent control, NAIA-4 or IAA at indicated concentrations for 2 h. The solution was replaced with new culture medium containing 10 μL of WST-8 solution (Abcam; ab228554) and incubated for 2 h in dark at 37° C. Cell viability were then assayed by the absorption at 460 nm on SpectraMax i3 (Molecular Devices).

MTT Cell Viability Assay of Cells Treated with NAIA-5

HepG2 cells were plated on 96-well plates (Corning, 3904) at 30,000 cells per well in 100 μL of complete medium and allowed to grow overnight. The cells were then incubated with DMSO solvent control or NAIA-5 at indicated concentrations for 1 h. The treated cells were then added with 10 μL of MTT solution in PBS (5 mg/mL) and incubated in dark at 37° C. with 5% $CO_2$ for 4 h. After that, 100 μL of SDS solution in PBS (0.5 g/mL with 0.01M HCl) was added for cell lysis. The plates were kept in dark overnight and cell viability were assayed by the absorption at 580 nm on Perkin Elmer Victor 3 (Molecular Devices).

HepG2 Cells Labeled by NAIA-5 or IAA with Different Time Intervals for Imaging Experiments HepG2 cells were plated on a 8-well Nunc Lab-Tek chambered slide system (ThermoFisher Scientific; 177402) and allowed to grow in complete medium at 37° C. with 5% $CO_2$ to ca. 70% confluency. The cells were incubated with NAIA-5 and IAA (10 μM) respectively in complete medium for the indicated time interval, washed with PBS and then fixed by 4% paraformaldehyde in PBS at room temperature for 15 min. After washing with PBS, the fixed cells were permeabilized by PBS with 0.5 vol % Triton X-100 at room temperature for 30 min. The cells were then washed and incubated with a master mix solution containing $CuSO_4$, THTPA, azide-fluor 545 and sodium ascorbate at final concentrations of 100, 500, 20 and 5000 μM respectively. After incubation in dark at room temperature for 1 h, the cells were washed with PBS and stained by Hoechst 33342 in PBS (final concentration=8.2 μM) at room temperature for 15 min. The cells were washed thrice with PBS and then imaged by confocal fluorescence microscopy. Hoechst 33342 was excited with a 405 nm diode laser, and emission was collected on a META detector between 371 and 507 nm. Fluor 545 was excited by a 561 nm diode laser and emission was collected on a META detector between 576 and 683 nm. Image analysis was performed by use of ImageJ. A region of interest (ROI) was created around individual cell, and cellular fluorescence intensity was measured. The reported average cellular fluorescence intensity was determined by averaging the measured intensity from 30 different cells from 3 different biological replicates/group. Statistical analyses were performed with a two-tailed Student's t-test (MS Excel).

Imaging a Decrease in Free Thiol Level in HepG2 Cells Under Oxidative Stress by NAIA-5 or IAA HepG2 cells were plated on a 8-well Nunc Lab-Tek chambered slide system and allowed to grow in complete medium at 37° C. with 5% $CO_2$ to ca. 70% confluency. The cells were then pretreated with solvent vehicles, $H_2O_2$ (0.5 or 1 mM) or $H_2O_2$ (1 mM)+NAC (5 mM) in complete medium for 15 min at 37° C. The cells were washed with PBS and incubated with NAIA-5 or IAA (50 μM) in complete medium for 10 min at 37° C. After that, the cells were washed with PBS and fixed by 4% paraformaldehyde in PBS at room temperature for 15 min. The fixed cells were washed with PBS, permeabilized by PBS with 0.5 vol % Triton X-100 at room temperature for 30 min, washed again with PBS and incubated with a master mix solution containing $CuSO_4$, THTPA, azide-fluor 545 and sodium ascorbate at final concentrations of 100, 500, 20 and 5000 μM respectively. After incubation in dark at room temperature for 1 h, the cells were washed with PBS and stained by Hoechst 33342 in PBS (final concentration=8.2 μM) at room temperature for 15 min. The cells were washed thrice with PBS and then imaged in PBS by confocal fluorescence microscopy.

Imaging Oxidized Thiols in HepG2 Cells Under Oxidative Stress by NAI/NAIA Couple HepG2 cells were plated on a 8-well Nunc Lab-Tek chambered slide system and allowed to grow in complete medium at 37° C. with 5% $CO_2$ to ca. 70% confluency. The cells were then pretreated with solvent vehicles, $H_2O_2$ (0.5 or 1 mM) or $H_2O_2$ (1 mM)+NAC (5 mM) in complete medium for 15 min at 37° C. The cells were washed with PBS and incubated with NAI compound 3 (50 μM) in complete medium for 10 min at 37° C. After that, the cells were washed with PBS and fixed by 4% paraformaldehyde in PBS at room temperature for 15 min. The fixed cells were washed with PBS, permeabilized by PBS with 0.5 vol % Triton X-100 at room temperature for 30 min, washed again with PBS and incubated with TCEP (1 mM) in PBS at room temperature for 1 h. The cells were then incubated with NAIA-5 (10 μM) in PBS at room temperature for 1 h, followed by washing with PBS and incubation with a master mix solution containing $CuSO_4$, THTPA, azide-fluor 545 and sodium ascorbate at final concentrations of 100, 500, 20 and 5000 μM respectively. After incubation in dark at room temperature for 1 h, the cells were washed with PBS and stained by Hoechst 33342 in PBS (final concentration=8.2 μM) at room temperature for 15 min. The cells were washed thrice with PBS and then imaged in PBS by confocal fluorescence microscopy.

Confocal Fluorescence Microscopy Imaging

Confocal fluorescence microscopy imaging was performed with a Zeiss laser scanning microscope 880 with a 20× water-immersion objective lens using ZEN 2.3 (Black Version) software (Carl Zeiss) with 3× magnification zoom-in. Hoechst 33342 was excited with a 405 nm diode laser, and emission was collected on a META detector between 371 and 507 nm. Fluor 545 was excited by a 561 nm diode laser and emission was collected on a META detector between 576 and 683 nm. Image analysis was performed by use of ImageJ. A region of interest (ROI) was created around individual cell, and cellular fluorescence intensity was measured. The reported average cellular fluorescence intensity was determined by averaging the measured intensity from 30 different cells from 3 different biological replicates/group. Statistical analyses were performed with a two-tailed Student's t-test (MS Excel).

MS-Based ABPP Experiments to Identify Liganded Cysteines in HepG2 Cell Lysates by NAIA-5 or IAA.

HepG2 cells were lysed in PBS by sonication. After BCA assay and protein normalization, HepG2 cell lysates in PBS (2 mg/mL, 2 mL) were incubated with NAIA-5 and IAA (10 μM), respectively, at room temperature for 1 h with vortexing. Then, the samples were incubated with a master mix solution for CuAAC reaction, containing $CuSO_4$, TBTA, DTB-PEG-azide and TECP (final concentrations are 1 mM, 100 μM, 100 μM and 1 mM respectively). After incubation at room temperature for 1 h with vortexing, pre-chilled acetone (12 mL) was added to the samples and proteins were allowed to precipitate out by storing at −20° C. overnight. The samples were centrifuged at 5,000 g at 4° C. for 10 min, and the supernatant was discarded. The protein pellets labeled by NAIA-5 and IAA were then combined and washed with pre-chilled methanol twice. The protein pellets were then re-dispersed in 1.2% SDS in PBS (w/v), followed by heating at 80° C. for 5 min. Any insoluble solids were discarded by centrifugation at 6,500 g for 5 min, and the supernatant were transferred to PBS solution containing Pierce™ Streptavidin Agarose beads (20349; Thermo Scientific) with final concentration of SDS equal to 0.2% (w/v). The samples and beads were incubated at 4° C. with rotation overnight. The beads were then washed with PBS and water, and re-dispersed in 6M urea in PBS. The samples were reduced by TCEP (1 mM) at 65° C. for 20 min, followed by alkylation with iodoacetamide (18 mM) at 37° C. for 30 min in dark. The beads were then spun down by centrifugation at 1,400 g for 2 min, washed with PBS and re-suspended in 2M urea in PBS. The proteins on the beads were then digested by sequencing grade trypsin (Promega) at 37° C. overnight. After tryptic digestion, the beads were spun down by centrifugation at 1,400 g for 2 min and the supernatant was discarded. The beads were washed thrice with PBS and thrice with water, followed by the addition of elution buffer solution (MeCN/$H_2O$, 1:1, v/v; with 0.1% formic acid) to the beads and incubation for 5 min at 37° C. The probe-modified peptides were eluted out from the beads and the supernatant was collected. The beads were incubated with a new elution buffer solution, spun down and the supernatant solution was combined with the previous solution. The combined solution containing the eluted probe-modified peptides were dried and desalted by C18 Stage tips, and the peptides (200 ng) were sent for LC-MS/MS analysis using Aurora C18 UHPLC column (75 μm i.d.×25 cm length×1.6 μm particle size; IonOpticks, Australia) coupled to timsTOF Pro mass spectrometer (Bruker).

Chromatographic separation was carried out using buffer A (buffer A: 98:2 water:acetonitrile, 0.1% formic acid) and B (acetonitrile: 0.1% formic acid) with the gradient from 98% buffer A to 30% buffer B at a flow rate of 300 nL/min over 100 min, followed by an increase from 30% to 44% buffer B over 5 min, an increase to 95% buffer B in 0.5 min, an isocratic gradient of 95% buffer B over 8.5 min, a decrease of buffer B to 2% in 0.5 min and then an isocratic gradient of 2% buffer B for 5.5 min. MS data was collected over a m/z range of 100 to 1700, and MS/MS range of 100 to 1700. During MS/MS data collection, each TIMS cycle was 1.1 s and included 1 MS+an average of 10 PASEF MS/MS scans.

The data was searched against the Uniprot human database using MaxQuant v2.0.3.0, specified with trypsin digestion (allowed up to 3 missed cleavages) and cysteine carbamidomethylation (+57.02146) as a static modification. The search also allowed up to 5 variable modifications for methionine oxidation (+15.99491), N-terminal acetylation (+42.01056), cysteine modification by NAIA-5 (+681.38500) or cysteine modification by IAA (+494.32167). The peptide false discovery rate (FDR) was set to 1%.

MS-Based ABPP Experiments to Identify Liganded Cysteines in 231MFP Cell Lysates by NAIA-4 or IAA Using Working Concentration of IAA and Multidimensional Protein Identification Technology (MudPIT).

231MFP cells were lysed in PBS by sonication. After BCA assay and protein normalization, 231MFP cell lysates in PBS (2 mg/mL, 2 mL) were incubated with NAIA-4 and IAA (100 μM; the working concentration of IAA in many reported MS-based ABPP experiments[74]), respectively, at room temperature for 1 h with vortexing. Then, the sample preparation until the step of peptide elution from streptavidin beads was the same as the one described for the HepG2 cell lysate experiment.

After elution of probe-modified peptides, a fused silica capillary tubing (250 μm inner diameter) packed with 4 cm of Aqua C18 reverse-phase resin (Phenomenex no. 04A-4299) was equilibrated by a high-performance liquid chromatograph using buffer A (buffer A: 95:5 water:acetonitrile, 0.1% formic acid) and B (buffer B 80:20 acetonitrile:water, 0.1% formic acid) with the gradient from 100% buffer A to 100% buffer B over 10 min, followed by a 5 min wash with 100% buffer B and a 5 min wash with 100% buffer A. Then, the eluted probe-modified peptides were pressure-loaded onto the capillary tubing. The tubing containing the peptide samples were then attached using a MicroTee PEEK 360 μm fitting (Thermo Fisher Scientific no. p-888) to a 13 cm laser pulled column packed with 10 cm Aqua C18 reverse-phase resin and 3 cm of strong-cation exchange resin. Samples were analyzed using an Q Exactive Plus mass spectrometer (Thermo Fisher Scientific) with a five-step Multidimensional Protein Identification Technology (MudPIT) program, using 0, 25, 50, 80 and 100% salt bumps of 500 mM aqueous ammonium acetate and using a gradient of 5-55% buffer B in buffer A. Data were collected in data-dependent acquisition mode with dynamic exclusion enabled (60 s). One full mass spectrometry (MS1) scan (400-1,800 mass-to-charge ratio (m/z)) was followed by 15 MS2 scans of the nth most abundant ions. Heated capillary temperature was set to 200° C. and the nanospray voltage was set to 2.75 kV.

Data was searched against the Uniprot human database using ProLuCID search methodology in IP2 v.3 (Integrated Proteomics Applications, Inc.).[77] Cysteine residues were searched with a static modification for carbamidomethylation (+57.02146) and up to two differential modifications for methionine oxidation, and cysteine modification by NAIA-4 or IAA (+681.38500 or +494.32167, respectively). Only fully tryptic peptides were analyzed. ProLuCID data was filtered through DTASelect to achieve a peptide false-positive rate below 5%.

MS-Based ABPP Experiments to Identify Liganded Cysteines in HepG2 Cells by Live-Cell Labeling Using NAIA-5 or IAA.

HepG2 cells were plated on 15 cm tissue culture plates and allowed to grow in complete medium at 37° C. with 5% $CO_2$ to ca. 80% confluency. The cells were then treated with NAIA-5 and IAA (10 μM), respectively, in complete medium and incubated at 37° C. with 5% $CO_2$ for 1 h. The cells were washed, scrapped in PBS and lysed by sonication. After BCA assay, the cell lysates were diluted to 2 mg/mL, and 2 mL of the lysates were used for n=1 sample preparation. The lysates were then subjected to CuAAC reaction with DTB-PEG-azide, acetone precipitation, enrichment by streptavidin beads, reduction by TCEP followed by cysteine carbamidomethylation and tryptic digestion according to the same procedure described for the sample preparation of HepG2 cell lysate experiment except no pairing of the NAIA-5- and IAA-labeled samples. The probe-modified peptides were then eluted by elution buffer solution (MeCN/$H_2O$, 1:1, v/v; with 0.1% formic acid), dried, desalted by C18 Stage tips and sent for LC-MS/MS analysis using Aurora C18 UHPLC column (75 μm i.d.×25 cm length×1.6 μm particle size; IonOpticks, Australia) coupled to timsTOF Pro mass spectrometer (Bruker), with the same experimental settings as described for the experiment on HepG2 cell lysates.

The data was searched using MaxQuant v2.0.3.0 with the same parameters as those used for experiment on HepG2 cell lysates as well.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Design, Synthesis and Characterization of NAIs and NAines

In view of the low nucleophilicity of indole nitrogen (even lower than C3 of indole), the key steps for synthesizing NAI (FIG. 8A) involves first reduction of indole to indoline by $NaBH_3CN$ in acetic acid, followed by reaction of nucleophilic indoline nitrogen with acryloyl chloride to install the acrylamide warhead and form NAine. Then, by 2,3-dichloro-5,6-dicyanobenzoquinone (DDQ)-mediated oxidation, this yielded acrylamide-containing indole, NAI, as the final product. To functionalize NAI into a probe, an alkyne handle was introduced to the NAI scaffold, so that it can undergo click reaction for conjugation to fluorophore or biotin moiety for ABPP, imaging and other profiling experiments. The synthesis of the alkyne derivative started with a 5-hydroxyindole, which reacted with tert-butyl bromoacetate to install the tert-butyl ester group onto the indole scaffold. Then by reduction, acryloyl chloride reaction and DDQ-mediated oxidation, compound 4, a NAI compound with protected carboxylic acid group, was synthesized. Further acid deprotection by $H_3PO_4$ and amide coupling reaction with hex-5-yn-1-amine yielded NAIA-5 as the final product. A positional isomer, NAIA-4, was also synthesized by the same synthetic scheme except using 4-hydroxyindole instead of the 5-hydroxyindole in the first step. All the compounds have been successfully characterized by $^1H$ NMR, $^{13}C\{^1H\}$ NMR, high resolution-MS and/or LC-MS.

Example 2—Cysteine Reactivity and Selectivity of NAIA

Figure 1A:
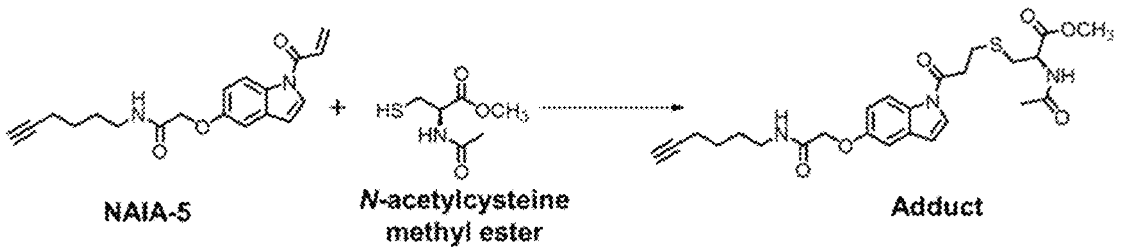
Figure 1B:
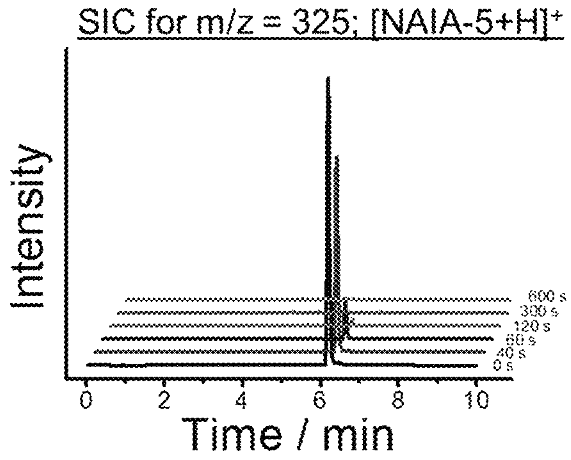
Figure 1C:
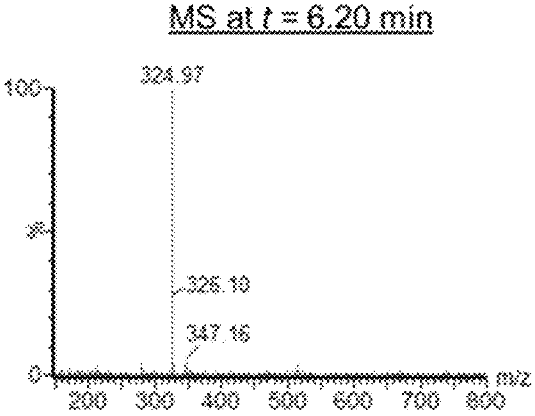
Figure 1D:
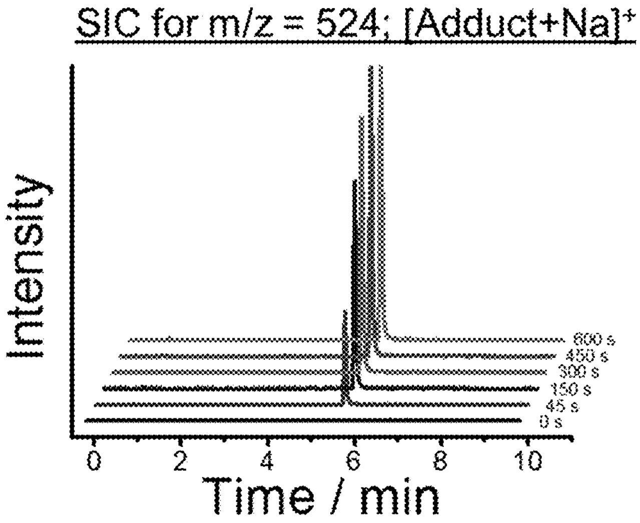
Figure 1E:
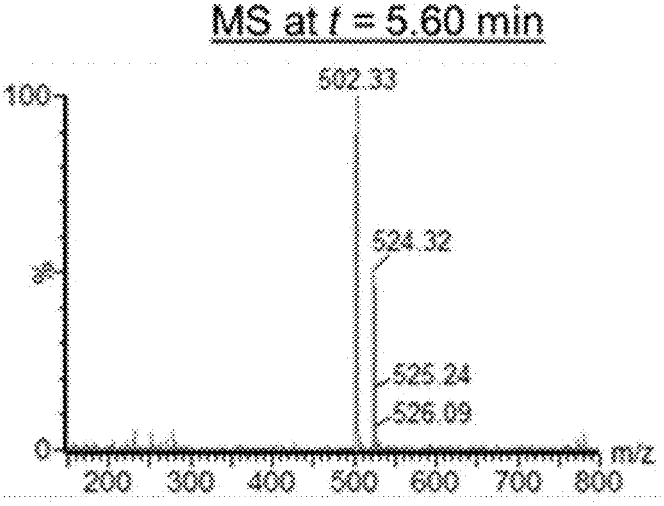
Figure 1F:
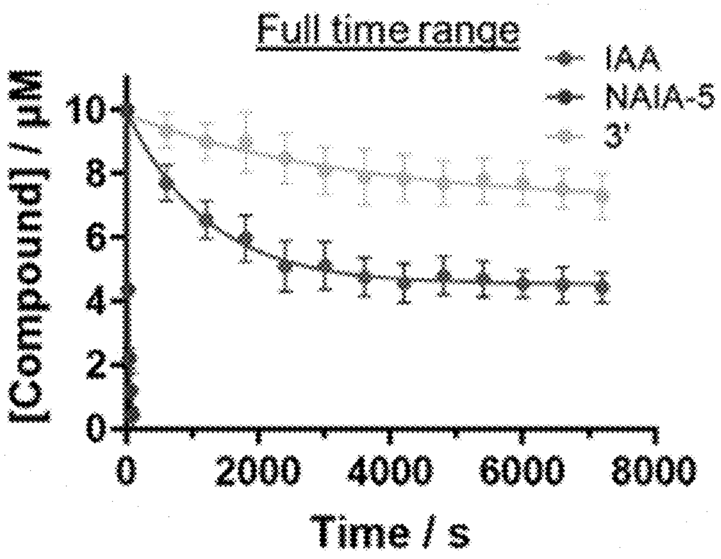
Figure 1G:
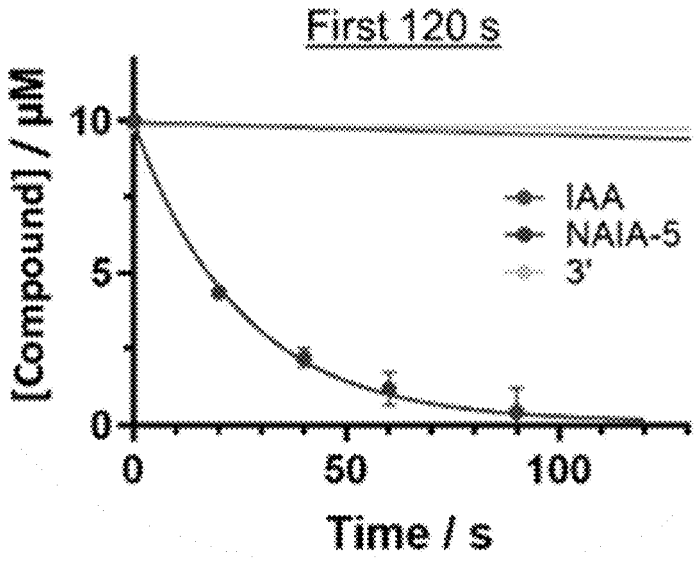
Figure 10A:
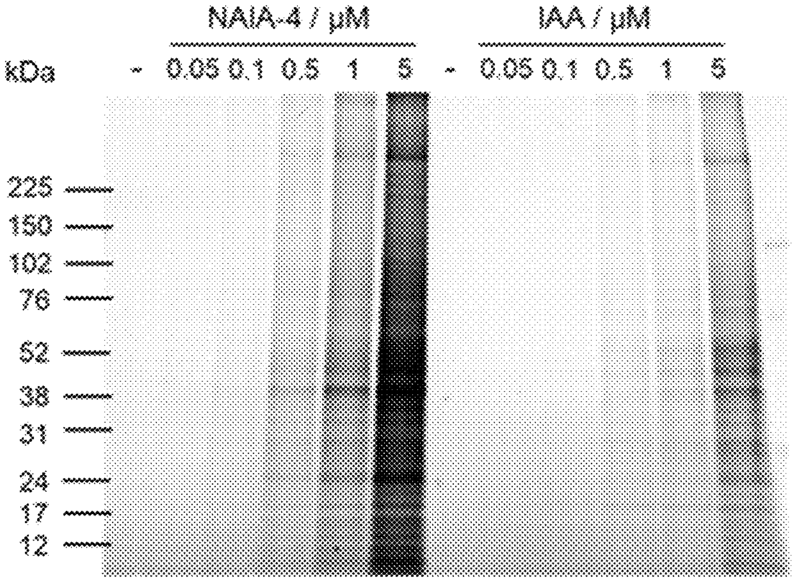
Figure 10B:
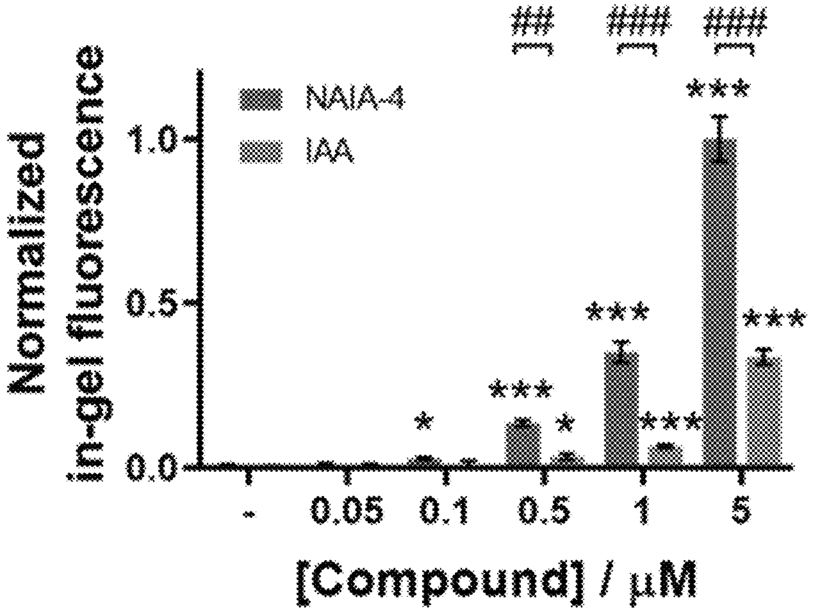
Figure 10C:
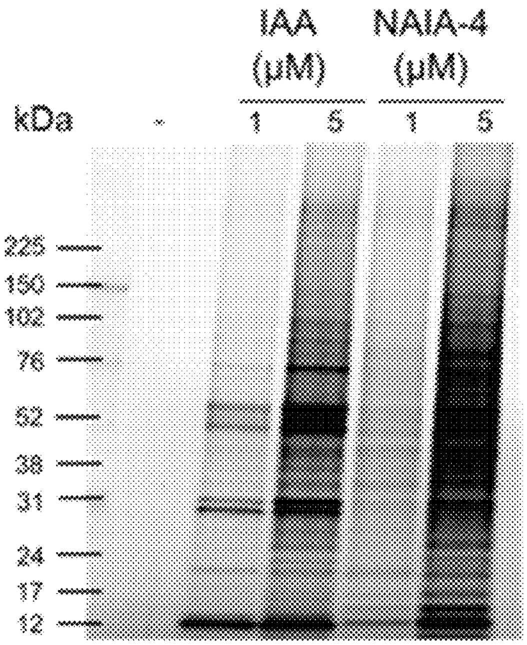
Figure 10D:
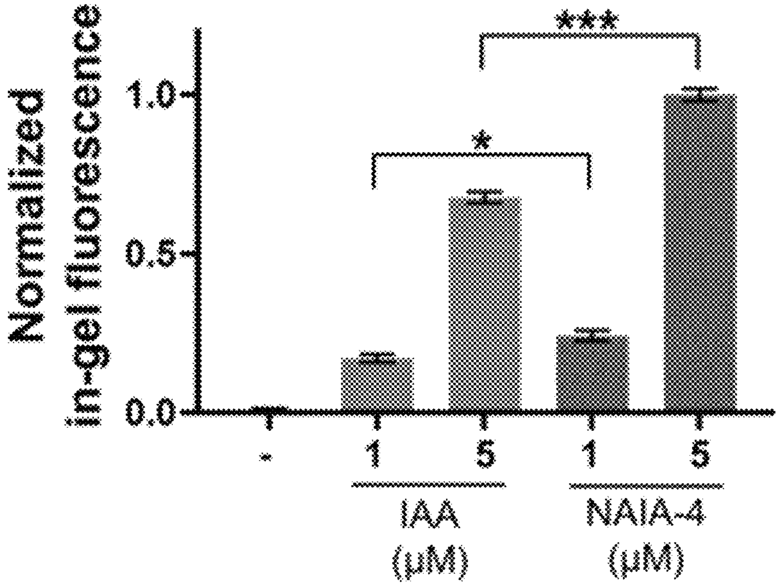

The reactivity of NAIA with cysteine in aqueous buffer solution has been investigated by LC-MS experiments (FIGS. 1A-1J). In the absence of the N- and C-terminal protected cysteine, N-acetylcysteine methyl ester, NAIA-5 (10 μM) in aqueous buffer solution (PBS/MeOH, 4:1, v/v) showed a peak at t=6.20 min in the liquid chromatogram (LC), which originates from the molecular ion $[NAIA\text{-}5+H]^+$ as supported by the mass spectrum (FIGS. 1B-1E). Upon addition of N-acetylcysteine methyl ester (250 μM), NAIA-5 reacted quickly and completely with N-acetylcysteine methyl ester within 300 s, as reflected by the diminishment of the peak of NAIA-5 at t=6.20 min with a concomitant growth of a new peak at t=5.60 min in the LC, which is attributable to the cysteine adduct of NAIA-5 based on the MS (FIGS. 1B-1G). For NAIA-4, it was found to react even faster with N-acetylcysteine methyl ester, and the thiol-Michael addition reaction was complete within 120 s (FIGS. 1A-1G). On the other hand, the conventional cysteine-reactive probe, IAA, was found to react much slower with cysteine than our NAIAs, and more than 40% of IAA was left unreacted according to the LC-MS experiment (FIGS. 1F-1G). Interestingly, compound 3, which is the reduced form of NAI and lacks the delocalization of π electrons to activate the acrylamide warhead, showed even slower cysteine reaction than IAA (FIGS. 1F-1G), and its biomolecular reaction rate constant was more than 330-fold lower than that of NAIA-4 (FIG. 1H). This highlights the important contribution of aromaticity of indole scaffold to increase electrophilicity of acrylamide warhead for fast and complete cysteine reaction in aqueous buffer solution. In addition to the fast reaction kinetics with cysteine, NAIA-4 and NAIA-5 exhibited excellent selectivity toward cysteine over other amino acids (FIGS. 1I and 9A-9G), typical for all acrylamide compounds owing to the high specificity of thiol-Michael addition reaction, while IAA showed undesired reactivity with serine and lysine (FIG. 10D). In view of the susceptibility of hydrolysis of N-acylindole in previous reported studies,[65] we also investigated stability of NAIA-5 in aqueous buffer solution by LC-MS, and found that in PBS solution at pH 7.4, NAIA-5 was stable over 3 hours (FIG.

1J). All these results suggest excellent cysteine reactivity and selectivity of NAIA, and demonstrate the good potential of using NAIA for ABPP and cysteine profiling experiments.

Example 3—Cysteine Labeling in Cell Lysates and Live Cells by NAIA

Figure 2A:
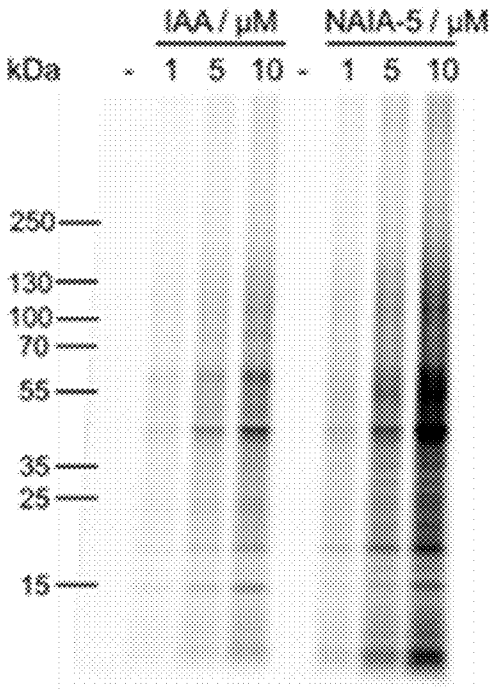
FIGS. 2A-2E. Gel-based experiments demonstrate excellent Cys labeling of cell lysates and live cells by NAIA-5.
Figure 2B:
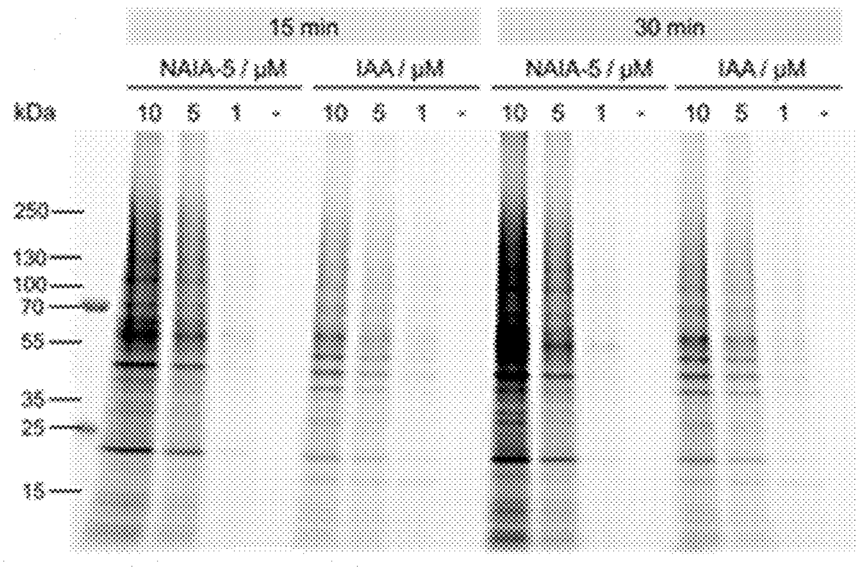
Figure 2C:
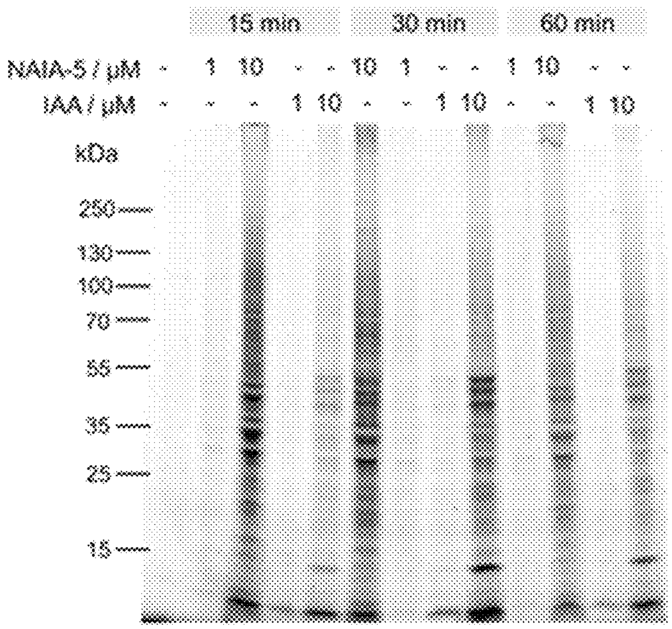
Figure 2D:
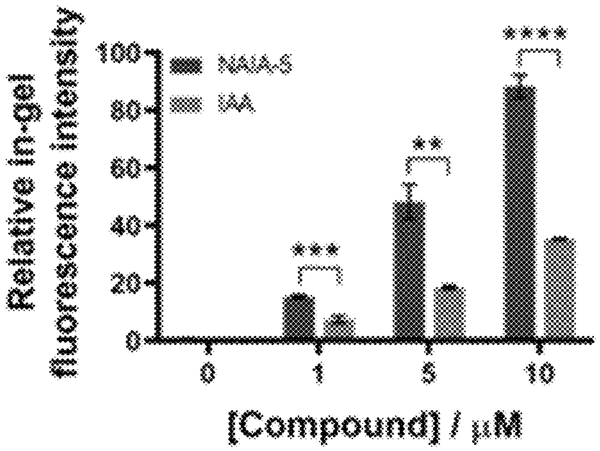

With the in vitro characterization data in hand, we next moved to investigate the ability of NAIA in labeling functional cysteines in cell lysates and live cells. In the experiments with HepG2 cell lysates, the cell lysates (100 μg) were first incubated with NAIA-5 and IAA, respectively, for 1 h at room temperature at indicated concentrations in FIG. 2A, and then reacted with azide-fluor 545 through copper(I)-catalyzed alkyne-azide cycloaddition (CuAAC). After the reaction, the protein mixture was resolved by sodium dodecyl sulphate-polyacrylamide gel electrophoresis (SDS-PAGE) and in-gel fluorescence was measured. Due to the cysteine reactivity from NAIA-5 and IAA, they were capable of labeling proteins in the cell lysates with reactive cysteines. This allows attachment of an alkyne handle onto these proteins; thus they can be conjugated to fluor 545 through CuAAC and hence showed strong fluorescence. The fluorescence intensity from these labeled protein bands can then reflect the degree of cysteine labeling by the probes. It was found that NAIA-5 showed more cysteine labeling than IAA at all the three doses tested with statistical significance (FIGS. 2A and 2D). Also, there were unique proteins labeled by NAIA-5 but not by IAA (FIG. 2A), illustrating the ability of NAIA-5 to expand the pool of ligandable cysteines. There were no significant change in band intensity in the gel stained by SimplyBlue™ SafeStain (FIGS. 12A and 12B), indicating the difference in in-gel fluorescence intensity originates from the different extents of cysteine labeling by NAIA-5 and IAA, instead of different protein loadings. Time-dependent experiments revealed quick labeling of HepG2 cell lysates by NAIA-5 even at 15 min, and the labeling increased with longer incubation time. Also, more cysteine labeling by NAIA-5 than IAA was found at 1 and 10 μM for both 15 and 30 min incubation (FIG. 2B). In addition to HepG2 cell lysates, NAIA also exhibited excellent performance on labeling reactive cysteines in lysates of 231MFP cells, as indicated by better labeling from NAIA-4 than IAA at all the doses tested (FIGS. 10A-10B). The different labeling patterns of NAIA-4 from that of IAA illustrate the potential of using NAIA-4 to identify new ligandable cysteines in 231MFP cells. Taken together, NAIAs are very promising candidates to probe ligandable cysteines in cell lysates, not only those known from IAA labeling but also new sets of cysteines which can be of great interest in the development of novel covalent ligands and inhibitors.

Figure 2E:
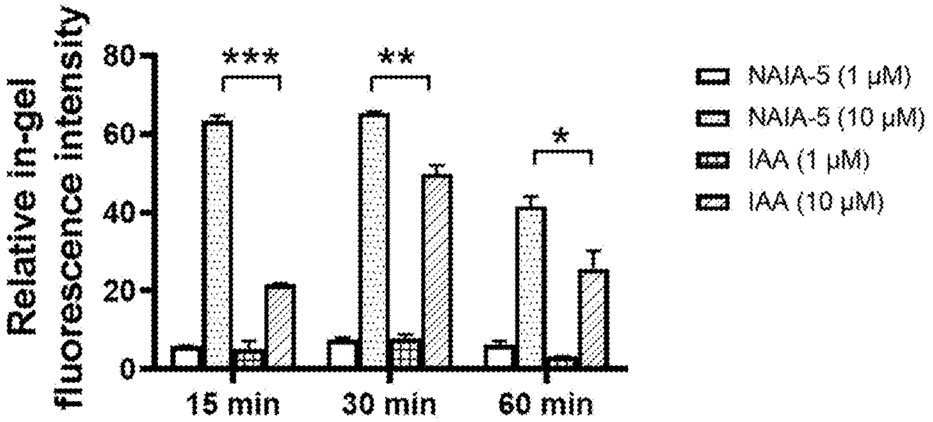
Figure 3A:
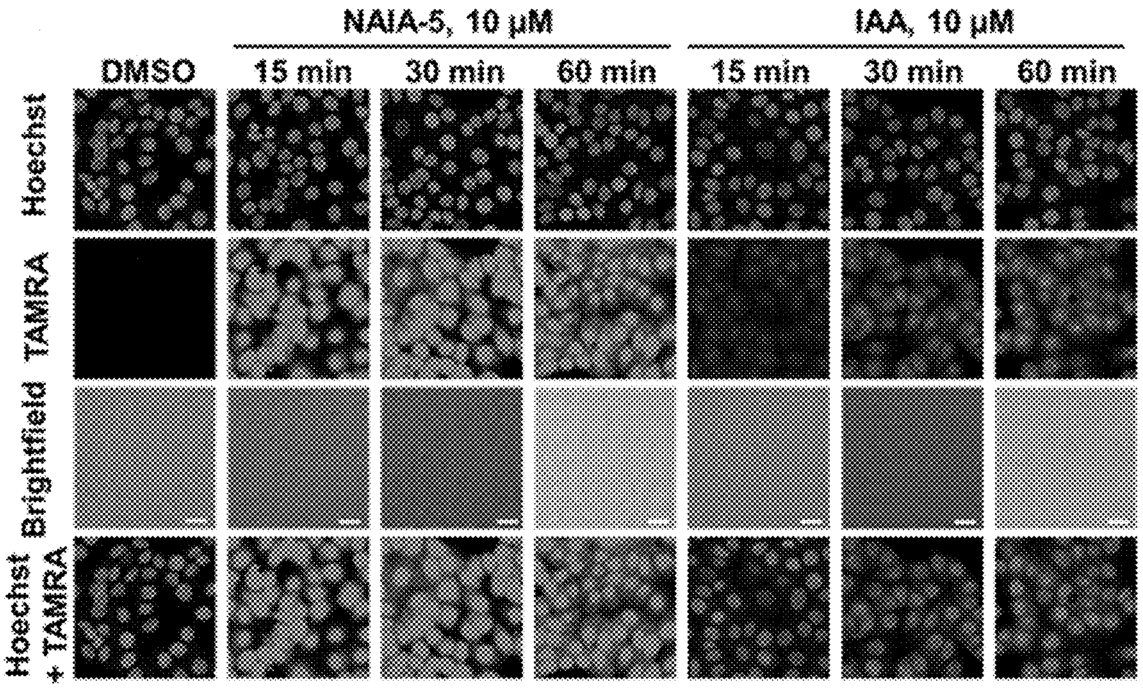
FIGS. 3A-3C. Confocal fluorescence imaging and cell viability assay reveal superior performance of NAIA on cysteine labeling of live cells.
Figure 3B:
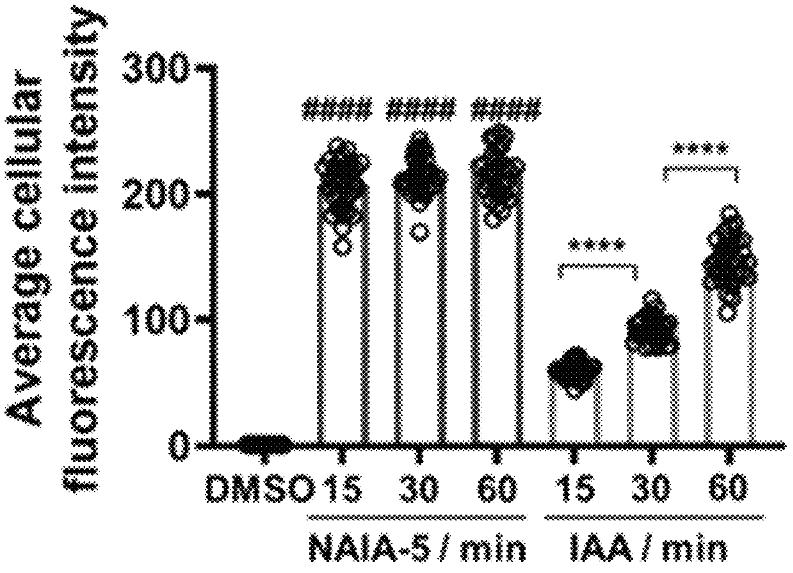
Figure 3C:
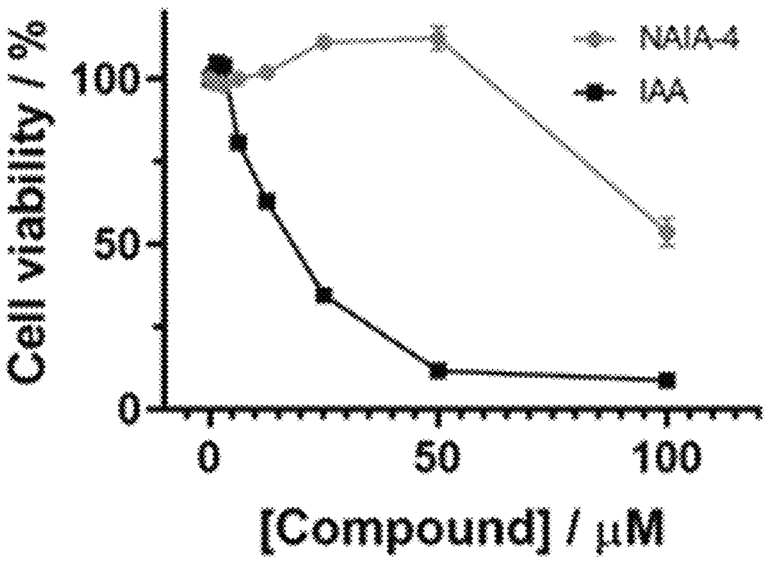

In view of the success in labeling cysteines in cell lysates, we then proceeded to apply NAIA for capturing reactive cysteines in live cells. Live HepG2 cells were incubated with NAIA-5 and IAA, respectively, in complete medium at indicated concentrations and time intervals shown in FIG. 2C. The treated cells were washed and lysed in PBS by probe sonication. After protein assay and normalization, the protein samples were subjected to click reaction with azide-fluor 545, followed by SDS-PAGE and in-gel fluorescence measurement. NAIA-5 was found to show better cysteine labeling than IAA at 10 μM for all the three incubation time intervals (FIG. 2C). Notably, the difference in in-gel fluorescence intensities between NAIA-5-labeled and IAA-labeled cells is huge at 15 min incubation (FIG. 2E). This can be attributable to the fast reaction kinetics of NAIA-5 with cysteines, as supported by the LC-MS experiment (FIGS. 1I-1J), and fast cellular uptake of the probe by HepG2 cells which we will show later in the confocal fluorescence imaging experiment (FIGS. 3A-3C). NAIA-5 also labeled a unique pool of cysteines which were not found by IAA labeling, in consistent to the cell lysate labeling experiment (FIGS. 2A-2B). Similar results on more labeling of functional cysteines by NAIA-4 than IAA were found in the experiments with 231MFP cells, showing that the superior performance of cysteine labeling by NAIA is not limited to a particular cell line.

To examine the underlying mechanism of better cysteine labeling in live cells by NAIA, we conducted confocal fluorescence imaging experiments on HepG2 cells treated with NAIA-5 and IAA respectively (both at 10 μM). After treatment for the indicated time intervals, the cells were washed with PBS, fixed by 4% paraformaldehyde in PBS and reacted with azide-fluor 545 through CuAAC. The stained cells were then washed with PBS and imaged by confocal fluorescence microscopy. Significantly higher fluorescence intensities were found in cells treated with NAIA-5 than IAA for all the three time points tested (15, 30 and 60 min; FIGS. 3A-3B), indicating more labeling of functional cysteines by NAIA-5. Notably, cells treated with NAIA-5 for 15 min already showed very strong fluorescence intensity, with no significant increase in intensity over time, while IAA-treated cells showed much weaker fluorescence at 15 min and the signal increased significantly with increasing incubation time (FIGS. 3A-3B). This suggests that NAIA-5 showed good cellular permeability and fast reaction kinetics with cysteine in live cells, where the latter is in consistent with our in vitro findings from LC-MS experiments (FIGS. 1A-1J), allowing NAIA-5 to quickly capture and label functional cysteines in cells. The weaker fluorescence from IAA-treated cells should be attributable to its relatively slow reactivity with cysteines in live cells, as it is known to show good cellular permeability. IAA has also been reported to show high cellular cytotoxicity, similar to what we found in the WST-8 assay on IAA-treated 231MFP cells (FIG. 3C). On the other hand, NAIA-4 and NAIA-5 exhibited much lower cytotoxicity as shown in WST-8 and MTT assay respectively ($IC_{50}$>40 μM; FIG. 3C), suggesting that they are better cysteine probes than IAA in live cells. More interestingly, NAIA-5 was found to show good labeling of proteins in both cytosol and nucleus, while the labeling of nuclear proteins by IAA is relatively smaller, as indicated by the lower Manders' colocalization coefficient of the protein fluorescence channel with the Hoechst channel. This again demonstrates the potential of using NAIAs to label new ligandable cysteines which is not feasible using conventional cysteine-reactive probe, particularly those on nuclear proteins. In view of the fast and better labeling of reactive cysteines in live cells, we anticipate that NAIAs can be good candidates for capturing cysteines with dynamic changes in reactivity/modifications in cells. The ability of NAIAs to work nicely with confocal fluorescence microscopic imaging also illustrates their potential application as imaging probes for cellular cysteine reactivity. All these prompt us to investigate further on the capability of NAIAs to image cysteine oxidation in cells under oxidative stress.

Example 4—Confocal Fluorescence Microscopy Imaging of Thiol Oxidation in Cells Under Oxidative Stress by NAI/NAIA Oxidative modifications of cysteines are known in cells facing oxidative stress, and these modifications can lead to significant changes in protein functions and activities, resulting in complex signaling cascades that can contribute to disease development and progression.[1,11,71] Identification of these oxidized cysteines and proteins would be critical for us to better understand physiology and pathology of these cysteine oxidative modifications, but this remains challenging because many of these modifications are highly dynamic and unstable. In view of the much lower reactivity of iodoacetamide with oxidized thiol as compared to the reaction with free thiol on cysteine, iodoacetamide and its derivatives have been employed for studying thiol oxidation using the global thiol trapping techniques such as OxICAT (ICAT=Isotope-coded Affinity Tag).[5,71-73] In these trapping techniques, cell lysis was performed using cell lysis buffer containing high concentrations of iodoacetamides so that free thiols could react with iodoacetamides and were trapped. Then, the oxidized thiols in the samples were reduced by reducing agents such as tris(2-carboxyethyl) phosphine (TCEP), followed by reaction with an iodoacetamide derivative. As a result, oxidized thiols can be differentiated from the unoxidized one, and this allows further identification of the proteins containing oxidized cysteines by MS experiments. These global thiol trapping techniques are powerful in studying oxidized thiols, but highly dynamic nature of thiol oxidative modifications may result in loss of oxidative modifications throughout cell lysis process. Trapping free thiols in live cells should be more preferable. Yet, the relatively slow reaction kinetics between iodoacetamide and cysteine require the use of large excess of iodoacetamide (100 mM in some reported studies[74,75]) which is far too toxic for live cell experiment, and hence thiol trapping by iodoacetamides was limited to experiments with cell lysates only.

Figure 4A:
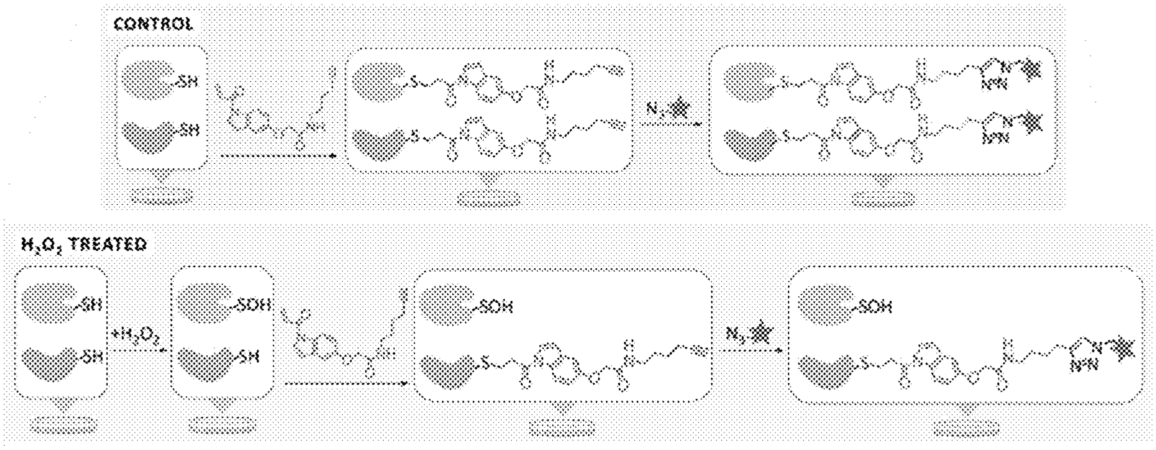
FIGS. 4A-4F. NAIA-5 allows successful imaging of changes in thiol reactivity in cells under oxidative stress by confocal fluorescence microscopy.
Figure 4B:
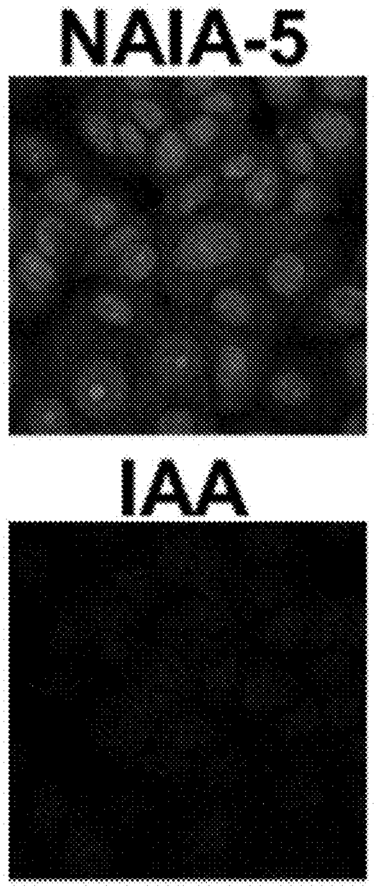
Figure 4C:
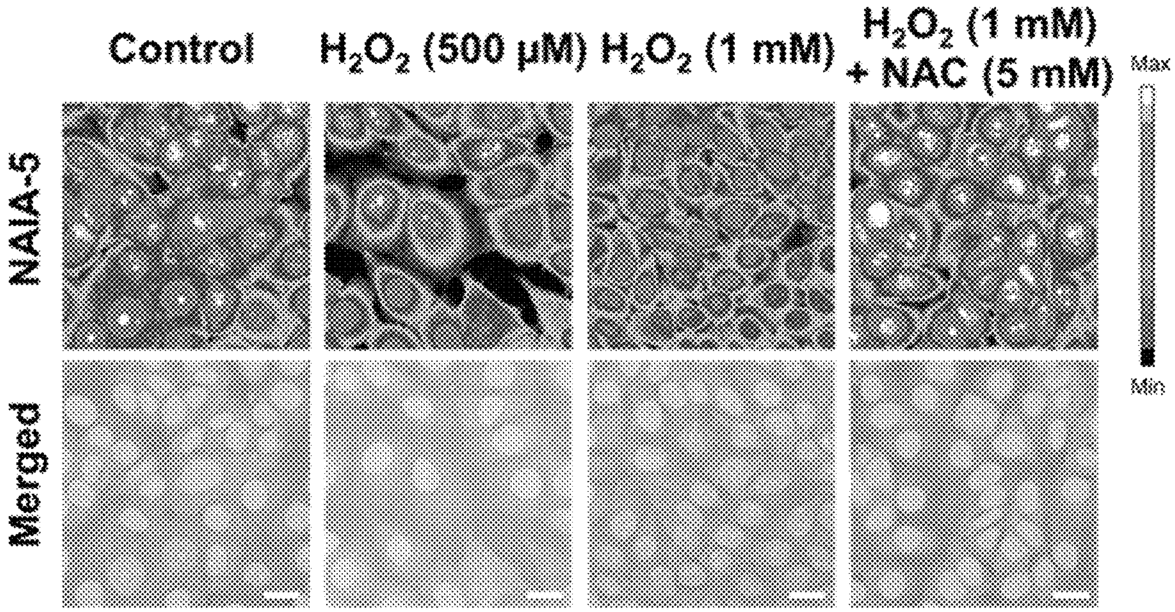
Figure 4D:
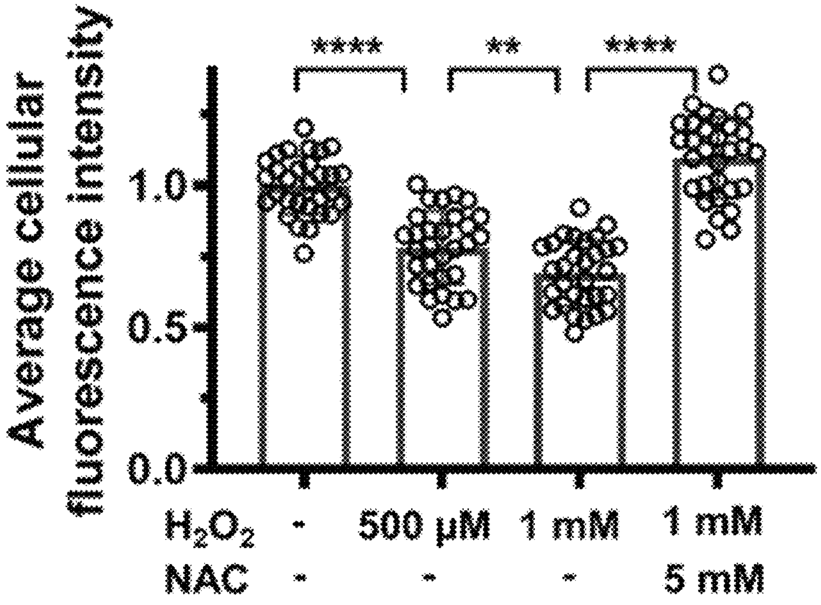
Figure 4E:
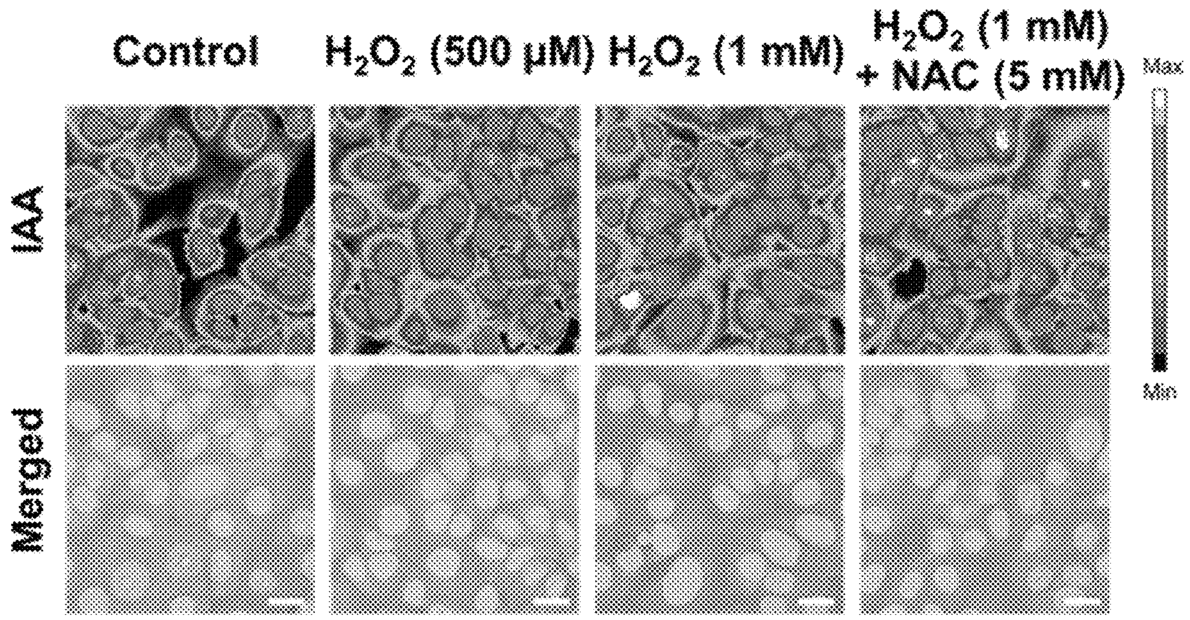
Figure 4F:
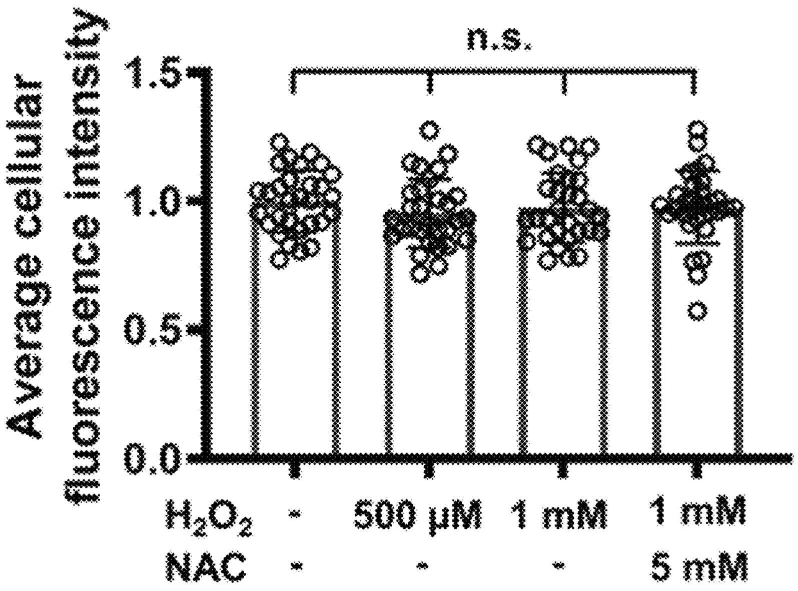

We have demonstrated fast and superior labeling of cellular thiols by NAIA-5 in live cells as compared to IAA (FIGS. 3A-3C), owing to its fast cysteine reaction kinetics and good cellular permeability. These attractive features indicate the good potential of using NAIs/NAIAs to trap cellular thiols in live cells that should allow better identification of cysteine oxidative modifications. To explore this potential application, we first sought to capture and image free thiols by NAIA-5 in live HepG2 cells by confocal fluorescence microscopy (FIG. 4A). HepG2 cells were pretreated with solvent vehicles, $H_2O_2$ or $H_2O_2$+N-acetyl cysteine (NAC), where NAC can scavenge $H_2O_2$ and relieve the oxidative stress in the HepG2 cells. After the pretreatment, the cells were incubated with NAIA-5 or IAA (50 μM) for 10 min to ligand and snap-shot free cellular thiols. The cells were then fixed, permeabilized, stained with azide-Fluor 545 through CuAAC reaction, incubated with Hoechst 33342 and imaged (FIGS. 4B-4F). For the cells pretreated with solvent control only, we observed strong fluorescence from NAIA-5 labeling, while almost no fluorescence can be detected in IAA-labeled cells using the same imaging parameters (FIG. 4B). This suggests much faster labeling and trapping of free thiols by NAIA-5 than IAA. On the other hand, a $H_2O_2$ dose-dependent decrease in cellular fluorescence intensity was found in cells labeled by NAIA-5, and co-incubation with NAC could restore the fluorescence intensity (FIGS. 4C-4D). This is attributable to the increase in thiol oxidations with increasing exogenous $H_2O_2$ concentration, leading to a decrease in free thiol level and hence reduced labeling by NAIA-5 that results in a lower cellular fluorescence intensity. NAC co-incubation with $H_2O_2$ can recuse cells from oxidative stress, so the fluorescence intensity from cells co-treated with NAC is significantly higher than those treated with $H_2O_2$ only. Interestingly, we cannot see statistically significant changes in fluorescence intensity from IAA-labeled cells upon $H_2O_2$ stimulation (FIGS. 4E-4F), even at high laser power to better capture the weaker fluorescence from IAA-labeled cells. We rationalize this by the slow thiol reaction kinetics of IAA, leading to incomplete trapping of cellular free thiols. As a result, IAA failed to monitor changes in free thiol level in cells pretreated with $H_2O_2$ or NAC. All these results highlight the importance of fast cysteine reaction kinetics and good cellular permeability of NAIA-5, thus allowing it to function as imaging probe to monitor changes in thiol reactivity and levels of thiol oxidations in cells, while the conventional cysteine probe IAA cannot work with the live cell labeling and imaging experiment.

This would be more advantageous to label and image oxidized thiols instead of the unoxidized ones for better determination of their identity and subcellular localization and hence understanding of their redox biology. Therefore, we sought to utilize the NAI/NAIA couple to capture oxidized thiols and image them by confocal fluorescence microscopy (FIGS. 12A-12B). In this experiment, HepG2 cells pretreated with solvent vehicles, $H_2O_2$ or $H_2O_2$+NAC, were incubated with our NAI compound 3b (50 μM, 10 min), which does not contain an alkyne handle, to trap and snap-shot free cellular thiols. Then the cells were fixed, permeabilized and reduced by TCEP to reduce thiols with reversible oxidative modifications back to the free thiol form. NAIA-5 (10 μM) was then added to the cells to label and capture these newly formed thiols. After that, Fluor 545 was installed onto NAIA-5-labeled proteins through CuAAC reaction with azide-Fluor 545. The cells were washed, stained with Hoechst 33342 and imaged by confocal fluorescence microscope. A $H_2O_2$ dose-dependent increase in fluorescence intensity was found (FIG. 12B), indicating the success of our NAI/NAIA couple to capture and image oxidized thiols as well as monitoring their elevated levels in cells facing oxidative stress. NAC co-incubation with $H_2O_2$ was found to attenuate the enhanced fluorescence intensity (FIG. 12B). This not only shows the ability of NAI/NAIA couple to image dynamic changes of thiol oxidative modifications in cells under different treatment conditions, but also confirms the excellent trapping of free thiols by NAI compound 3b in live cells so that NAIA-5 can specifically capture oxidized thiols for imaging. In view of the fact that many reported thiol trapping techniques are applicable for cell lysates only, they cannot work with imaging experiments to detect and monitor thiol oxidations with high spatial resolution. The readiness of NAI/NAIA to trap/label cellular thiols in live cells enables them to function as probes for imaging experiments. This can be a good methodology to investigate cellular thiol oxidative modifications, as well as other dynamic changes in thiol functionality and activity.

Example 5—MS-Based Chemoproteomics Analysis on Cysteine Profiling by NAIAS

NAIAs have been found to label a larger and new population of functional cysteines in the gel-based ABPP experiments (FIGS. 2A-2E). To identify these functional cysteines, MS-based chemoproteomics experiments have been applied for investigations of NAIA-treated cell lysates and live cells respectively. We first started with cell lysates as IAA is known to be a good probe for profiling cysteines in cell lysates, so a comparative study between NAIA and IAA can be made. For this identification experiment, we utilized the MS-based ABPP platform, which has been demonstrated to be powerful for studying functional amino acids such as cysteine, serine and lysine,[20-25, 57] with small modifications as illustrated in FIG. 13. HepG2 cell lysates in PBS were incubated with NAIA-5 and IAA (both at 10 μM), respectively, at room temperature for 1 h, followed by CuAAC reaction with desthiobiotin (DTB)-PEG-azide to install DTB moiety onto the labeled proteins by NAIA-5 and IAA. After acetone precipitation and methanol washing to remove excess reagents for the CuAAC reaction, the NAIA-5-treated sample was mixed with IAA-treated sample in 1:1 ratio, and then subjected to streptavidin enrichment, cysteine carbamidomethylation and on-bead tryptic digestion. After washing out the tryptic digests, the DTB-labeled peptides were eluted from the streptavidin bead using acetonitrile-water mixture (1:1, v/v) with 0.1% formic acid. These eluted peptides were sent for a simple LC-MS/MS analysis using a short LC gradient of 2 h, and the MS data were searched for NAIA-5 and IAA specific modifications on Cys by MaxQuant to identify peptides labeled by NAIA-5 and IAA respectively. It is noteworthy that in this experiment, the NAIA-5-treated sample was first mixed with IAA-treated sample before tryptic digestion and LC-MS/MS analysis, thus any difference found in labeling by NAIA-5 or IAA should not be attributable to discrepancy in sample preparation or MS running condition and hence this allows good comparison of NAIA-5 with IAA for proteome-wide cysteine profiling. Also, the incubation concentration of IAA with the cell lysates (10 μM) was much lower than its working concentration reported in previous studies for cysteine profiling (>100 μM), as we are aiming to develop a better cysteine probe that can profile cysteine effectively even at low working concentrations and NAIA-5 has been found to label cysteines well at 10 μM in the gel-based ABPP experiments (FIGS. 2A-2E). Together with the using of a short 2 h-gradient LC run, it is expected that the number of IAA-labeled peptides identified from this set of experiment should be smaller than those found in reported studies.

Figure 5A:
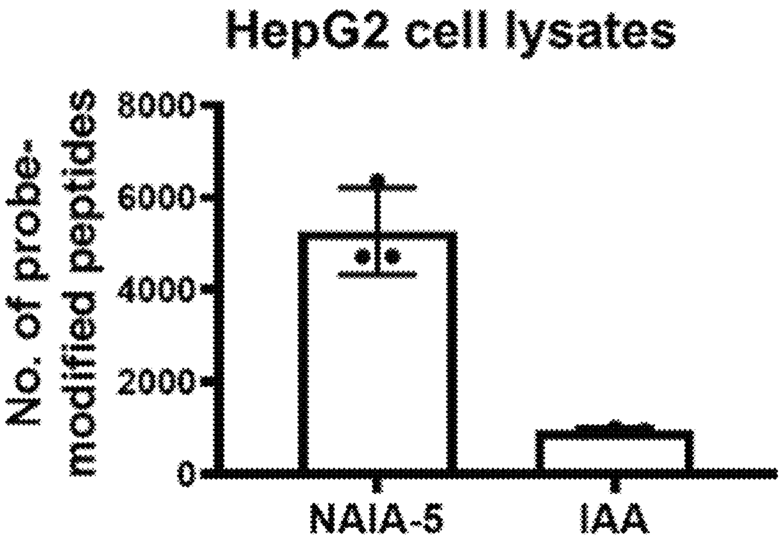
FIGS. 5A-5E. LC-MS/MS-based chemoproteomics experiment to investigate Cys profiling of HepG2 cell lysates by NAIA-5 and IAA.
Figure 5B:
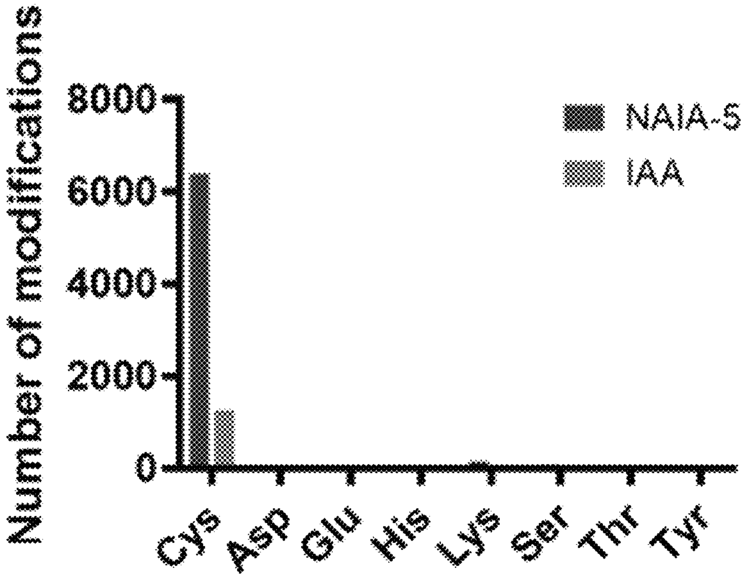
Figure 5C:
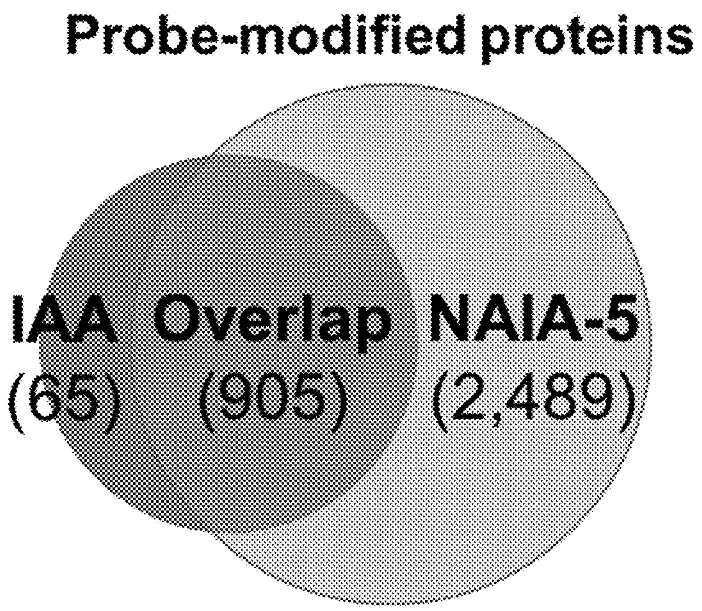

We found that there were significantly higher number of peptides modified by NAIA-5 than IAA in all the triplicate samples (average numbers with modifications by NAIA-5 and IAA are 5,269 and 957 respectively; FIG. 5A). NAIA-5 also profiled a larger population of cysteines than IAA in aggregate (6,387 vs 1,257; FIG. 5B), with less undesired off-target labeling onto other amino acids as compared to IAA (FIGS. 14A-14B). These profiled cysteines by NAIA-5 were on 3,394 different proteins, showing overlap with only 905 proteins which were also labeled by IAA, while the remaining 2,489 proteins represent the unique pool of proteins with functional cysteines profiled by NAIA-5 in this experiment (FIG. 5C). These results indicate the capability of NAIA-5 in coupling with MS-based chemoproteomics experiment for proteome-wide cysteine profiling. In addition, the significantly higher number of profiled cysteines as well as unique labeling by NAIA-5 demonstrates its potential to unravel new ligandable cysteines for biological studies and drug research.

Figure 5D:
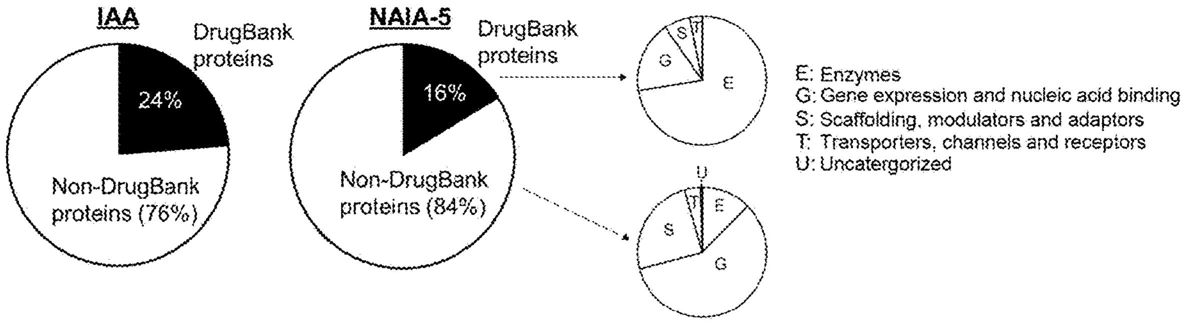
Figure 5E:
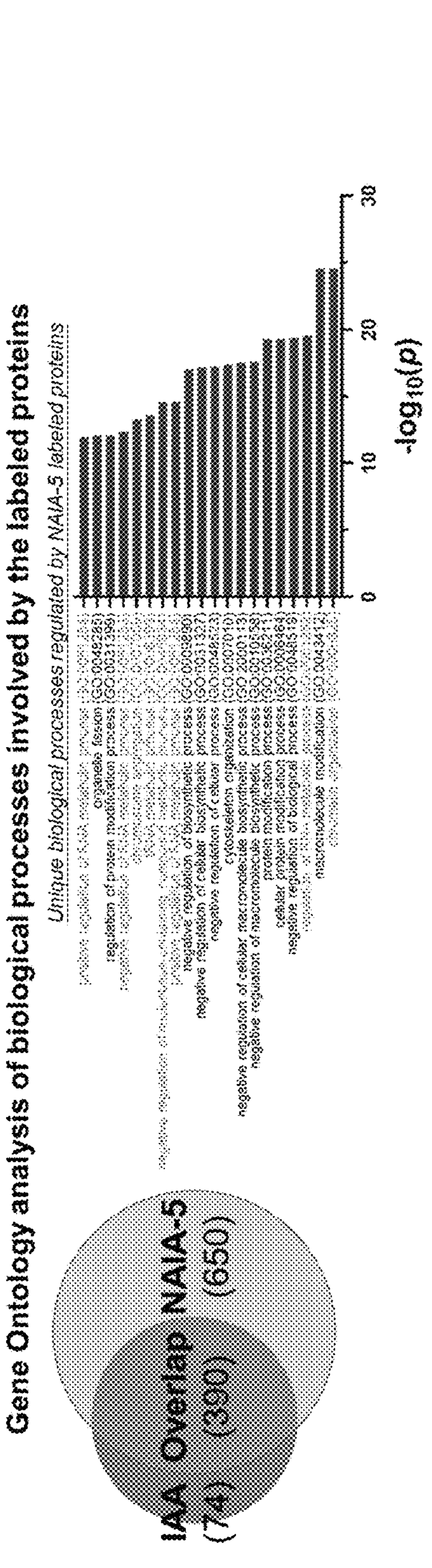

To further investigate properties of labeled proteins by NAIA-5 and IAA, we utilized DrugBank database[66, 67] and Gene Ontology (GO) analysis[68] to examine the availability of pharmacophores to drug these labeled proteins and their biological functions respec-tively. It was found that 84% of proteins labeled by NAIA-5 were not on the list of DrugBank (non-DrugBank proteins) and it is more than the 76% found for IAA (FIG. 5D), suggesting the potential application of NAIA-5 to identify and study new protein targets which have not yet been drugged currently. More interestingly, for the proteins on the list of DrugBank (DrugBank proteins) with NAIA-5 labeling, they are mostly enzymes according to GO analysis. The non-DrugBank pro-teins show very different profiles in term of their biological functions, with proteins involved in gene expression and regulation as the largest category (FIG. 5D). Further GOanalysis on biological processes regulated by the profiled proteins from NAIA-5 revealed 650 processes which are unique for NAIA-5 and not found in IAA profiling, with a significant contribution from processes associated with gene expression and regulation (FIG. 5E) on the top 20 unique processes. In view of the fact that transcription factors and their associated proteins are often considered as one of the most important protein targets for therapy but remain mostly undrugged,[22, 24, 26-28, 31] this is anticipated that NAIA-5, when it is employed in competitive binding experiment with covalent ligands, can be a valuable tool for identifying new covalent drug lead compounds to target these important proteins. It would also be useful for studying changes in protein functions and activities after compound binding to determine therapeutic values of the compounds.

Figure 15A:
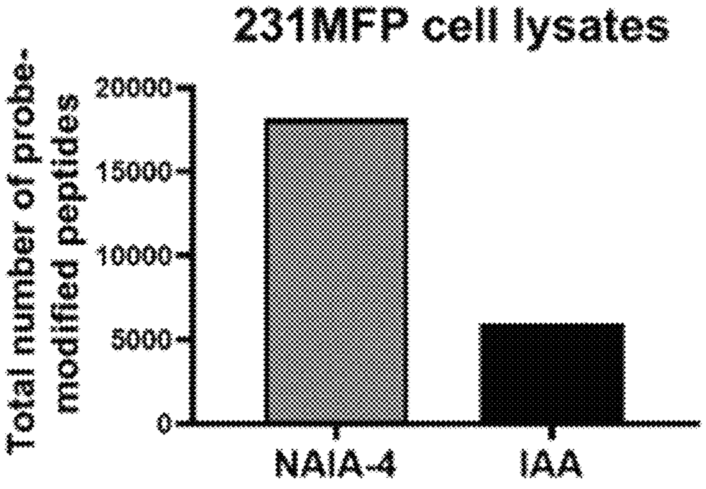
Figure 15B:
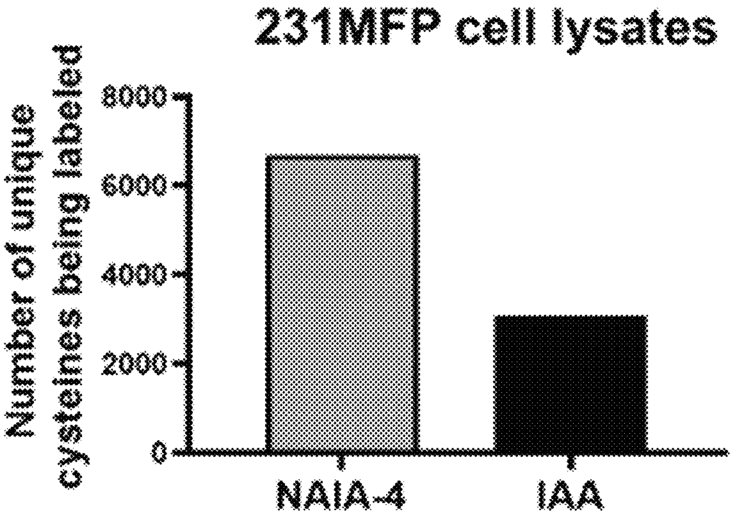
Figure 15C:
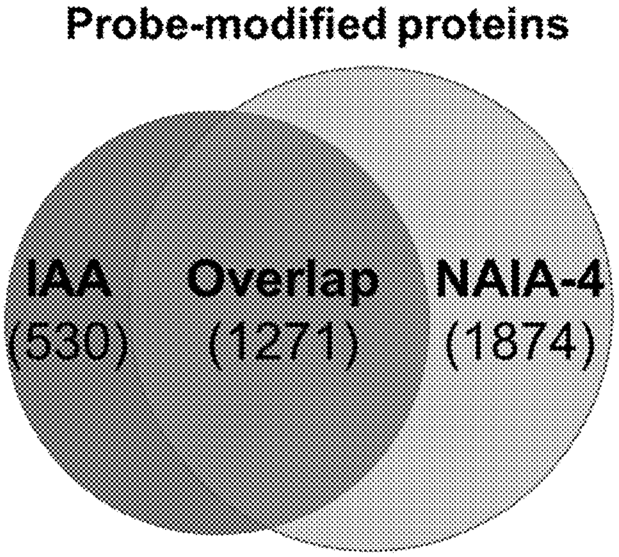
Figure 15D:
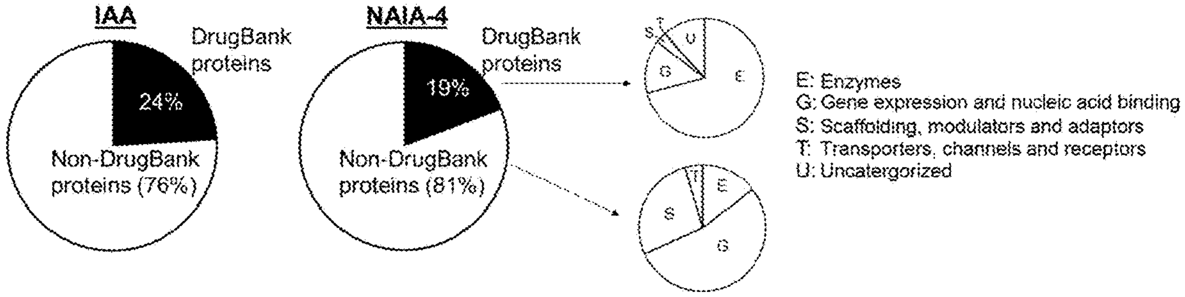
Figure 15E:
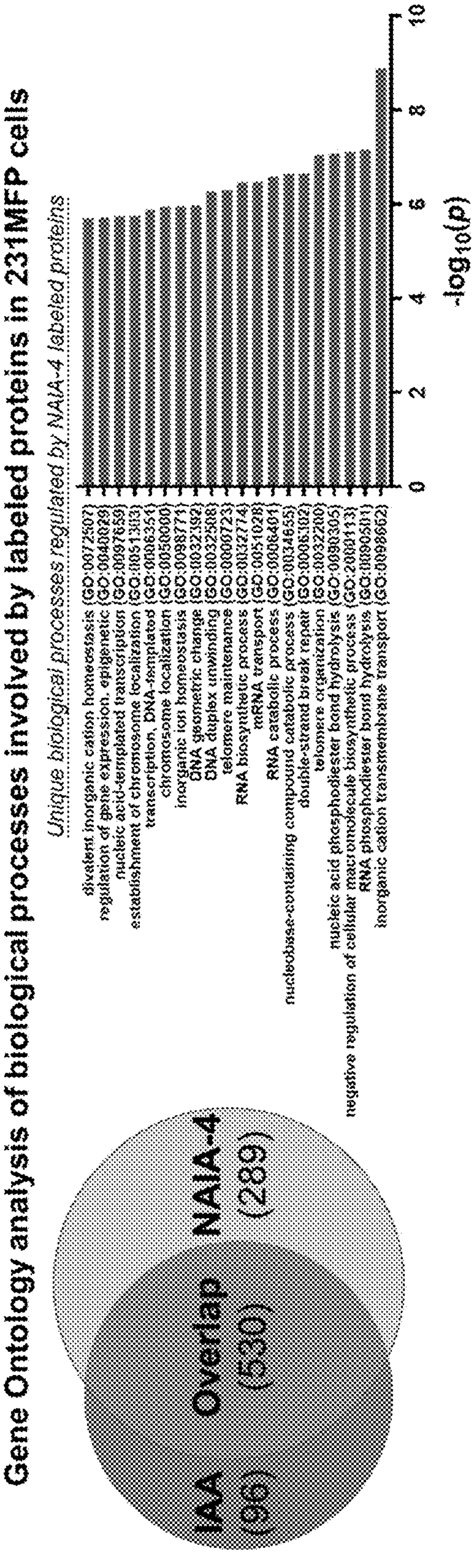

IAA has been widely used for cysteine profiling of cell lysates by Multidimensional Protein Identification Technology (MudPIT)[5,6,69], which can significantly enhance peptide separation and hence increase resolution and number of identified peptides in LC-MS/MS experiments. To investigate the applicability of NAIA for coupling with MudPIT for cysteine profiling, we treated 231MFP cell lysates with NAIA-4 and IAA (both at 100 μM; the working concentration of IAA in many reported studies), respectively, at room temperature for 1 h, and then subjected to similar sample preparation as outlined in FIG. 13 until peptide elution. The eluted peptides were then loaded onto laser-pulled column packed with C18 and strong-cation exchange (SCX) resin, and analyzed by LC-MS/MS in a five-step of chromatography run as reported previously.[5,6] In this experiment, both NAIA-4 and IAA liganded and identified more functional cysteines than the experiment with short LC gradient, but NAIA-4 still showed a larger number of probe-modified peptides (18,241 for NAIA-4 vs 6,104 for IAA) and better profiling of a larger population of cysteines than IAA (6,692 for NAIA-4 and 3,072 for IAA; FIGS. 15A-15B). Similar to the finding in the experiment with HepG2 cell lysates (FIG. 5C), a large population of proteins uniquely profiled by NAIA-4 but not by IAA were found in the MudPIT experiment with 231MFP cell lysates (~1,800; FIG. 15C), again illustrating the potential of using NAIA to expand the pool of ligandable cysteines for functional studies and drug research. DrugBank analysis revealed a larger percentage of non-DrugBank proteins profiled by NAIA-4 as compared to those profiled by IAA, and over half of these proteins were found to involve in gene expression and nucleic acid binding (FIG. 15D). GO analysis indicated that 292 biological processes were regulated by proteins profiled by NAIA-4 only, and many of the top 20 processes are associated with gene expression and transcription (FIG. 15E). All these results are in consistent to the findings from the HepG2 experiments, supporting the robust applications of NAIAs for proteome-wide cysteine profiling in different biological samples. In addition, although the total number of probe-modified peptides by NAIA were found to increase significantly by using higher concentration of NAIA (100 vs 10 μM) and coupling with MudPIT, the population of cysteines being profiled by NAIA only shows a small increment (6,692 vs 6,387), while the increase in population of profiled cysteines is huge for IAA (3,072 vs 1,257). This further highlights the attractive features of using NAIAs as activity-based probe for proteome-wide cysteine profiling, which are its lower working concentration and its readiness in performing reasonably good cysteine profiling using a simple experimental setup.

Figure 6A:
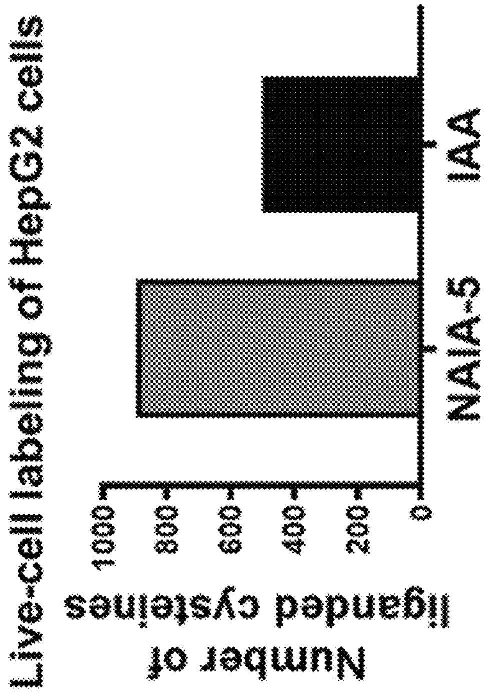
Figure 6B:
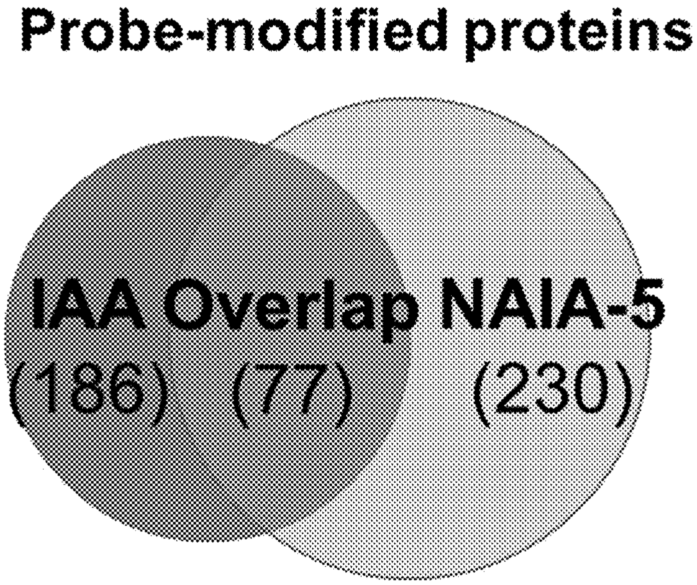
Figure 6C:
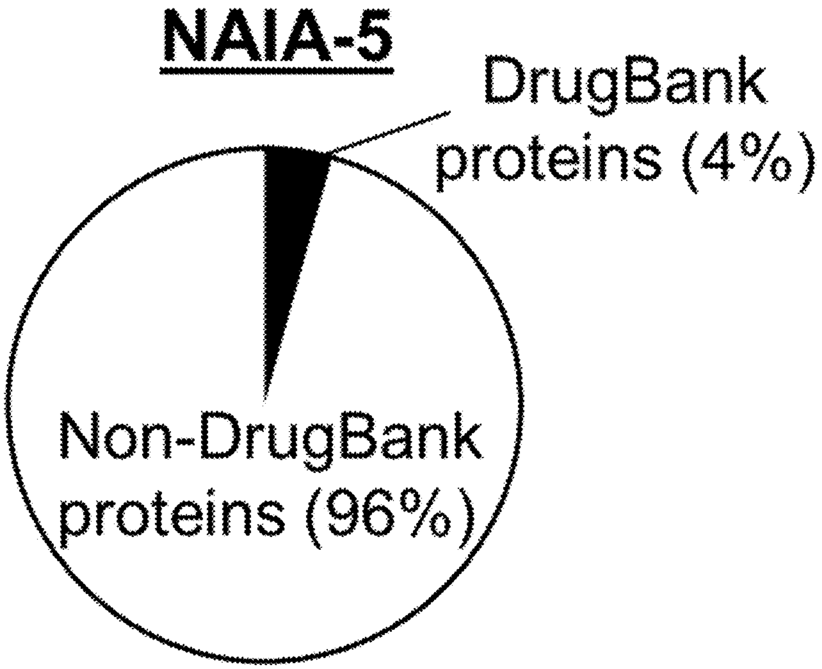
Figure 7:
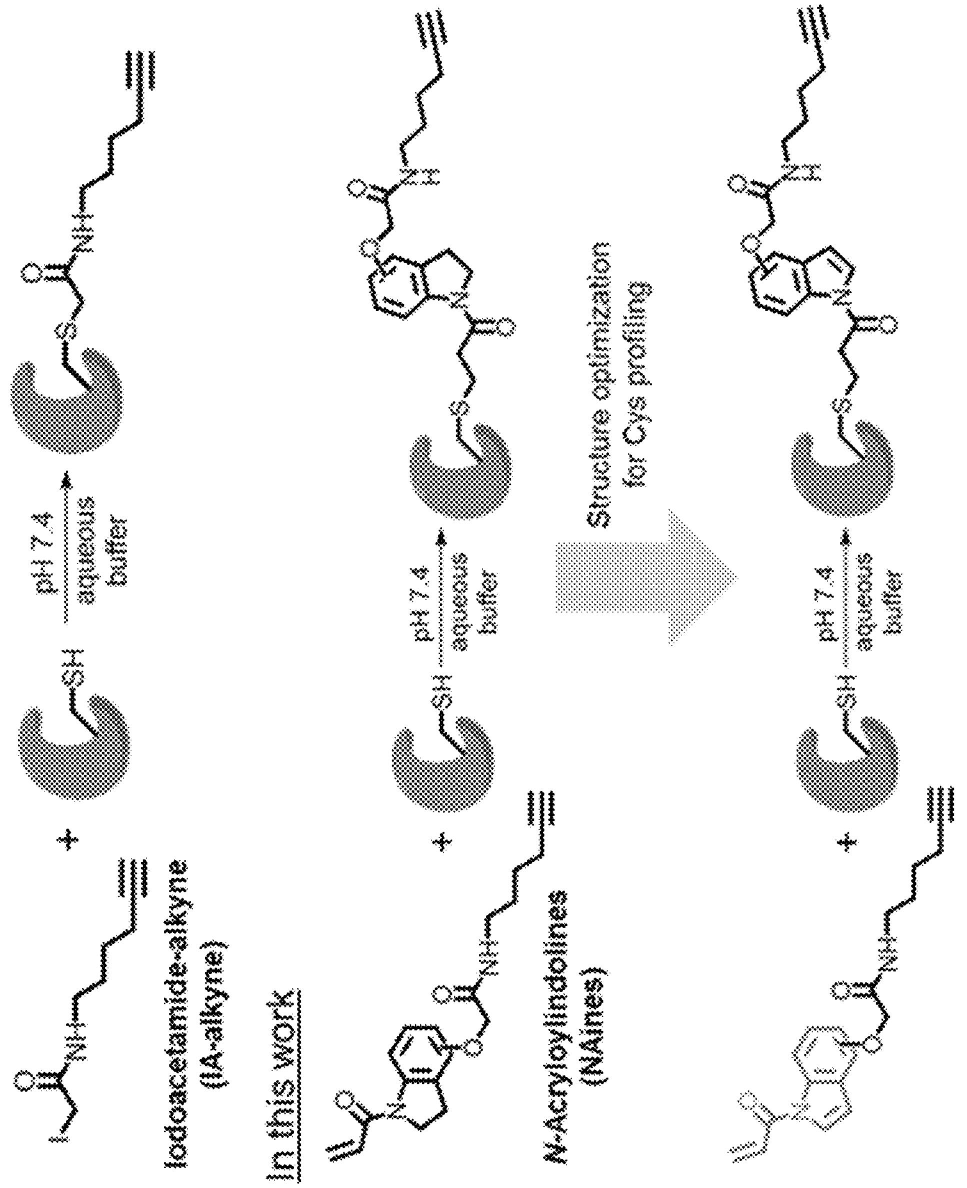
FIG. 7. N-Acryloylindole (NAI) as a new chemical tool for Cys profiling. Delocalization of a electrons over NAI increases electrophilicity of the acrylamide warhead, resulting in activation of the acrylamide for fast and complete reaction with nucleophilic Cys, which is not found in other acrylamide compounds such as the negative control N-acryloylindoline (NAine). Together with good selectivity toward Cys, low cellular toxicity and formation of stable Cys-adduct readily detectable by MS, NAI enables both in vitro and live-cell Cys profiling by gel-based and MS-based chemoproteomic experiments. IAA can have side reaction with sulfenic acid, lysine, and serine. IAA has low stability, has only fair reaction kinetics with cysteine ($k\sim10^0\ M^{-1}\ s^{-1}$)

Finally, we sought to utilize NAIA for profiling functional cysteines in live cells. To this end, live HepG2 cells were incubated with NAIA-5 and IAA, respectively, in complete medium at 10 μM for 1 h at room temperature, where no significant cellular toxicity was found as indicated by MTT and WST-8 assays (FIG. 3C). The treated cells were washed and lysed in PBS by sonication, followed by protein assay and normalization. The samples were then subjected to the same MS preparation protocol for cell lysates as outlined in FIGS. 14A and 14B, except no mixing of the NAIA-5-treated sample with IAA sample after the click reaction because live-cell labeling efficiency is expected to be lower than that in cell lysates and separate LC-MS/MS runs should prevent ionization suppression and allow better cysteine profiling. NAIA-5 was found to show a higher number of labeled cysteines than IAA (FIG. 6A) and many of these cysteines were on the proteins which cannot be profiled by IAA (FIG. 6B). This indicates that NAIA-5 is a promising activity-based probe for live-cell cysteine profiling, particularly on expanding the pool of ligandable cysteines. In addition, over 96% of proteins labeled by NAIA-5 remain undrugged currently according to DrugBank analysis (FIG. 6C), and interestingly quite a number of them, especially those involved in gene expression and regulations, have not been found to be liganded even in cell lysates by IAA or other conventional cysteine probes[70] (FIG. 6D). The ability of NAIA-5 to label these proteins uniquely in live cells suggests that NAIs, with the activated acrylamide warhead for fast and selective reactions with cysteine, are of good potentials for further development into covalent ligands or even drug lead compounds to target this unique pool of proteins for therapy.

Example 6—Synthesis and Characterization of Amide Derivatives of NAIA, NAIA-Amide NAIA-amides were synthesized according to the synthetic scheme shown in FIG. 16. Details of the experimental procedures and characterization data can be found below.

General Procedure: Amide Coupling

DIPEA (3.0 equiv.) was added to corresponding carboxylic acid (1.0 equiv.) in dry DMF (2 mL) followed by the addition of HATU (1.1 equiv.) on ice. The solution mixture was stirred for 10 min. After that, hex-5-yn-1-amine (1.5 equiv.) was added to the solution mixture and stirred overnight at room temperature. The reaction was then quenched by water, and the aqueous layer was extracted with ethyl acetate and washed with brine twice. Organic solvent was dried over $MgSO_4$ and evaporated to dryness. The crude product was purified by column chromatography on silica gel as described below.

Synthesis of NAIA-C3-Amide

Compound 1. Indole-3-carboxylic acid (100 mg) was reacted with hex-5-yn-1-amine following the general procedure for amide coupling. The crude was eluted by column chromatography using dichloromethane/methanol (20:1, v/v) to afford 1 as a white crystal (55 mg, 50.1%). 1H NMR (600 MHz, Chloroform-d) δ 9.93 (s, 1H), 7.93 (ddt, J=8.2, 5.0, 2.3 Hz, 1H), 7.68 (dd, J=3.0, 1.4 Hz, 1H), 7.46-7.34 (m, 1H), 7.26-7.18 (m, 2H), 6.17 (q, J=5.1 Hz, 1H), 3.52 (dt, J=8.2, 6.8 Hz, 2H), 2.24 (tdd, J=7.0, 2.8, 1.2 Hz, 2H), 1.96 (t, J=2.6 Hz, 1H), 1.81-1.71 (m, 2H), 1.67-1.57 (m, 2H).

NAIA-C3 amide. Compound 1 (55 mg, 1.0 equiv.) was dissolved in dry THF (4 mL) on ice, $K_2CO_3$ (94.9 mg, 3.0 equiv.) was added to the stirring solution. At 0° C., acryloyl chloride (37 μL, 2 equiv.) in dry THF (1 mL) was added dropwise to the solution mixture with vigorous stirring at 0° C. The solution mixture was stirred overnight, and then the reaction was filtered to obtain the organic phase. Organic solvent was dried over $MgSO_4$ and evaporated to dryness, and the crude product was purified by column chromatography on silica gel using hexane/ethyl acetate (10:1, v/v) as eluent, yielding NAIA-C3 amide as a white-off solid (6 mg, 10.2%). 1H NMR (600 MHz, Chloroform-d) δ 8.79 (s, 1H), 8.11-8.06 (m, 1H), 7.59 (d, J=3.1 Hz, 1H), 7.46-7.43 (m, 1H), 7.35-7.30 (m, 2H), 6.26 (dd, J=16.7, 1.9 Hz, 1H), 6.18 (dd, J=16.7, 10.1 Hz, 1H), 5.41 (dd, J=10.0, 1.8 Hz, 1H), 3.96 (t, J=7.4 Hz, 2H), 2.22 (td, J=7.1, 2.6 Hz, 2H), 1.91 (t, J=2.6 Hz, 1H), 1.84 (ddt, J=12.4, 8.0, 3.7 Hz, 2H), 1.61 (d, J=7.8 Hz, 2H). 13C NMR (151 MHz, Chloroform-d) δ 169.05, 168.18, 136.26, 132.14, 131.04, 127.18, 125.54, 124.26, 122.96, 121.35, 114.53, 111.80, 84.06, 68.61, 45.63, 32.75, 31.93, 31.59, 30.95, 30.04, 29.70, 29.37, 28.25, 25.95, 22.70, 22.66, 18.14, 14.13.

Synthesis of NAIA-C4-Amide

Compound 2. Indole-4-carboxylic acid (200 mg) was reacted with hex-5-yn-1-amine following the general procedure for amide coupling. The crude was eluted by column chromatography using dichloromethane/ethyl acetate (80:20, v/v) to afford 2 as a yellow oil (210 mg, 70.4%). 1H NMR (600 MHz, Chloroform-d) δ 9.26 (s, 1H), 7.49-7.42 (m, 2H), 7.26 (d, J=2.8 Hz, 1H), 7.14 (t, J=7.7 Hz, 1H), 6.84-6.82 (m, 1H), 6.42 (t, J=5.8 Hz, 1H), 3.53 (td, J=7.1, 5.8 Hz, 2H), 2.24 (td, J=7.0, 2.6 Hz, 2H), 1.96 (t, J=2.7 Hz, 1H), 1.76 (tt, J=7.5, 6.3 Hz, 2H), 1.65-1.58 (m, 2H).

Compound 3. To a stirring solution of 2 (98 mg, 1 equiv.) dissolved in AcOH (2 mL), $NaBH_3CN$ (105 mg, 4 equiv.) was added portion-wise in a water bath. After completion of reaction, NaOH was added to quenched and neutralize the reaction. Subsequently, the aqueous layer was extracted with ethyl acetate. Organic solvent was dried over $MgSO_4$ and evaporated to dryness, and the crude product was purified by column chromatography on silica gel using dichloromethane/ethyl acetate (50:50, v/v) as eluent, yielding 3 a transparent oil (20.2 mg, 20.5%). 1H NMR (400 MHz, Chloroform-d) δ 7.07 (t, J=7.7 Hz, 1H), 6.88 (d, J=7.7 Hz, 1H), 6.73 (d, J=7.7 Hz, 1H), 6.01 (s, 1H), 3.61 (t, J=8.4 Hz, 2H), 3.48 (q, J=6.7 Hz, 2H), 3.33 (t, J=8.4 Hz, 2H), 2.29 (td, J=6.9, 2.7 Hz, 2H), 2.20 (s, 1H), 1.99 (t, J=2.7 Hz, 1H), 1.79-1.73 (m, 2H), 1.67-1.62 (m, 2H).

Compound 4. Compound 3 (20.2 mg, 1.0 equiv.) was dissolved in dry THF (4 mL) on ice, $K_2CO_3$ (23.2 mg, 2.0 equiv.) was added to the stirring solution. At 0° C., acryloyl chloride (7.6 μL, 1.2 equiv.) in dry THF (1 mL) was added dropwise to the solution mixture with vigorous stirring at 0° C. After reaction completed, the reaction mixture was filtered and evaporated to dryness. The crude was purified by column chromatography on silica gel using dichloromethane/ethyl acetate (60:40, v/v) as eluent yielding 4 as a white crystal (16.7 mg, 67%). 1H NMR (400 MHz, Chloroform-d) δ 8.46 (d, J=8.0 Hz, 1H), 7.19 (d, J=7.7 Hz, 1H), 6.68-6.47 (m, 2H), 6.15 (s, 1H), 5.84 (dd, J=9.5, 2.6 Hz, 1H), 4.21 (t, J=8.5 Hz, 2H), 3.51 (dq, J=19.9, 7.6, 6.7 Hz, 4H), 2.29 (td, J=6.9, 2.7 Hz, 2H), 2.00 (t, J=2.7 Hz, 1H), 1.81-1.72 (m, 2H), 1.68-1.60 (m, 3H).

NAIA-C4 amide. DDQ (15.0 mg, 1.3 equiv.) was added to a stirring solution of 4 in dry toluene (15.0 mg, 1.0 equiv.). The reaction mixture was heated under reflux overnight. After that, toluene solvent was removed by evaporation under reduced pressure. The remaining was dissolved in ethyl acetate and washed with $NaHCO_3$ thrice. Organic solvent was dried over $MgSO_4$ and evaporated to dryness. The crude was purified by column chromatography on silica gel using dichloromethane/ethyl acetate (80:20, v/v) as eluent yielding NAIA-C4 amide as a brown crystal (5.3 mg, 35.6%). 1H NMR (400 MHz, Chloroform-d) δ 8.69 (d, J=8.3 Hz, 1H), 7.64 (d, J=3.8 Hz, 1H), 7.55 (dd, J=7.6, 0.9 Hz, 1H), 7.45-7.40 (m, 1H), 7.01 (dd, J=16.8, 10.4 Hz, 1H), 6.73 (dd, J=16.8, 1.4 Hz, 1H), 6.20 (s, 1H), 6.11 (dd, J=10.4, 1.4 Hz, 1H), 3.57 (q, J=6.7 Hz, 2H), 2.31 (td, J=6.9, 2.6 Hz, 2H), 2.00 (t, J=2.6 Hz, 1H), 1.86-1.78 (m, 2H), 1.72-1.65 (m, 2H), 1.28 (t, J=7.1 Hz, 1H).

Synthesis of NAIA-C5-Amide

Compound 5. Indole-5-carboxylic acid (100 mg) was reacted with hex-5-yn-1-amine following the general procedure for amide coupling. The crude was eluted by column chromatography using dichloromethane/ethyl acetate (80:20, v/v) to afford 5 as a white crystal (122 mg, 81.8%). 1H NMR (600 MHz, Chloroform-d) δ 9.66 (s, 1H), 8.12-8.07 (m, 1H), 7.59 (dd, J=8.5, 1.8 Hz, 1H), 7.33 (d, J=8.5 Hz, 1H), 7.23-7.18 (m, 1H), 6.61 (t, J=5.7 Hz, 1H), 6.54-6.46 (m, 1H), 3.47 (td, J=7.1, 5.7 Hz, 2H), 2.19 (td, J=7.0, 2.7 Hz, 2H), 1.96 (t, J=2.7 Hz, 1H), 1.77-1.66 (m, 2H), 1.58 (dq, J=10.2, 7.1 Hz, 2H).

Compound 6. To a stirring solution of 5 (100 mg, 1 equiv.) dissolved in AcOH (2 mL), $NaBH_3CN$ (105 mg, 4 equiv.) was added portion-wise in a water bath. After completion of reaction, NaOH was added to quenched and neutralize the reaction. Subsequently, the aqueous layer was extracted with ethyl acetate. Organic solvent was dried over $MgSO_4$ and evaporated to dryness, and the crude product was purified by column chromatography on silica gel using dichloromethane/ethyl acetate (50:50, v/v) as eluent, yielding 6 a transparent oil (34.2 mg, 20.5%). 1H NMR (600 MHz, Chloroform-d) δ 7.54 (q, J=1.4 Hz, 1H), 7.45 (dd, J=8.2, 1.9 Hz, 1H), 6.57 (d, J=8.1 Hz, 1H), 5.98 (s, 1H), 4.01 (s, 1H), 3.63 (t, J=8.5 Hz, 2H), 3.46 (td, J=7.1, 5.8 Hz, 2H), 3.06 (t, J=8.5 Hz, 2H), 2.26 (td, J=7.0, 2.7 Hz, 2H), 1.97 (t, J=2.6 Hz, 1H), 1.75-1.69 (m, 2H), 1.66-1.59 (m, 2H).

Compound 7. Compound 6 (34.2 mg, 1.0 equiv.) was dissolved in dry THF (4 mL) on ice, $K_2CO_3$ (39 mg, 2.0 equiv.) was added to the stirring solution. At 0° C., acryloyl chloride (13.7 μL, 1.2 equiv.) in dry THF (1 mL) was added dropwise to the solution mixture with vigorous stirring at 0° C. After reaction completed, the reaction mixture was filtered and evaporated to dryness. The crude was purified by column chromatography on silica gel using dichloromethane/ethyl acetate (40:60, v/v) as eluent yielding 7 as a white crystal (16.7 mg, 67%). 1H NMR (600 MHz, Chloroform-d) δ 8.36-8.16 (m, 1H), 7.72-7.62 (m, 1H), 7.56 (d, J=8.4 Hz, 1H), 6.55 (q, J=16.3, 13.2 Hz, 2H), 6.26 (t, J=5.9 Hz, 1H), 5.86-5.81 (m, 1H), 4.22 (t, J=8.5 Hz, 2H), 3.48 (q, J=6.7 Hz, 2H), 3.24 (t, J=8.6 Hz, 2H), 2.26 (td, J=7.0, 2.7 Hz, 2H), 1.97 (t, J=2.7 Hz, 1H), 1.75 (dd, J=9.0, 6.1 Hz, 2H), 1.63 (dd, J=9.0, 6.2 Hz, 2H).

NAIA-C5 amide. DDQ (37.9 mg, 1.3 equiv.) was added to a stirring solution of 6 in dry toluene (38 mg, 1.0 equiv.). The reaction mixture was heated under reflux overnight. After that, toluene solvent was removed by evaporation under reduced pressure. The remaining was dissolved in ethyl acetate and washed with $NaHCO_3$ thrice. Organic solvent was dried over $MgSO_4$ and evaporated to dryness. The crude was purified by column chromatography on silica gel using hexane/ethyl acetate (80:20, v/v) as eluent yielding NAIA-C5 amide as a brown crystal (16.2 mg, 43.0%). 1H NMR (600 MHz, Chloroform-d) δ 8.52 (d, J=8.6 Hz, 1H), 8.06 (d, J=1.8 Hz, 1H), 7.73 (dd, J=8.7, 1.9 Hz, 1H), 7.58 (d, J=3.8 Hz, 1H), 6.97 (dd, J=16.7, 10.5 Hz, 1H), 6.74-6.67 (m, 2H), 6.31 (t, J=5.7 Hz, 1H), 6.09 (dd, J=10.4, 1.4 Hz, 1H), 3.52 (td, J=7.1, 5.7 Hz, 2H), 2.27 (td, J=6.9, 2.6 Hz, 2H), 1.98 (t, J=2.6 Hz, 1H), 1.78 (tt, J=7.8, 6.4 Hz, 2H), 1.67-1.62 (m, 2H). 13C NMR (151 MHz, Chloroform-d) δ 167.69, 163.88, 137.41, 132.84, 130.62, 130.49, 127.55, 125.83, 123.45, 120.37, 116.62, 109.62, 84.08, 68.81, 39.61, 28.76, 25.79, 18.15. 13C NMR (151 MHz, Chloroform-d) δ 167.69, 163.88, 137.41, 132.84, 130.62, 130.49, 127.55, 125.83, 123.45, 120.37, 116.62, 109.62, 84.08, 68.81, 39.61, 28.76, 25.79, 18.15.

Figure 17A:
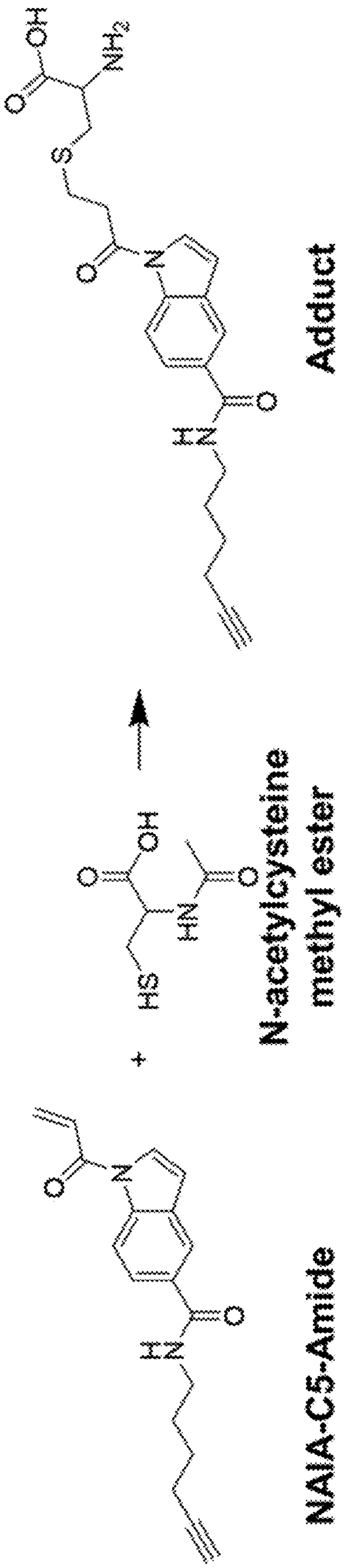
Figure 17B:
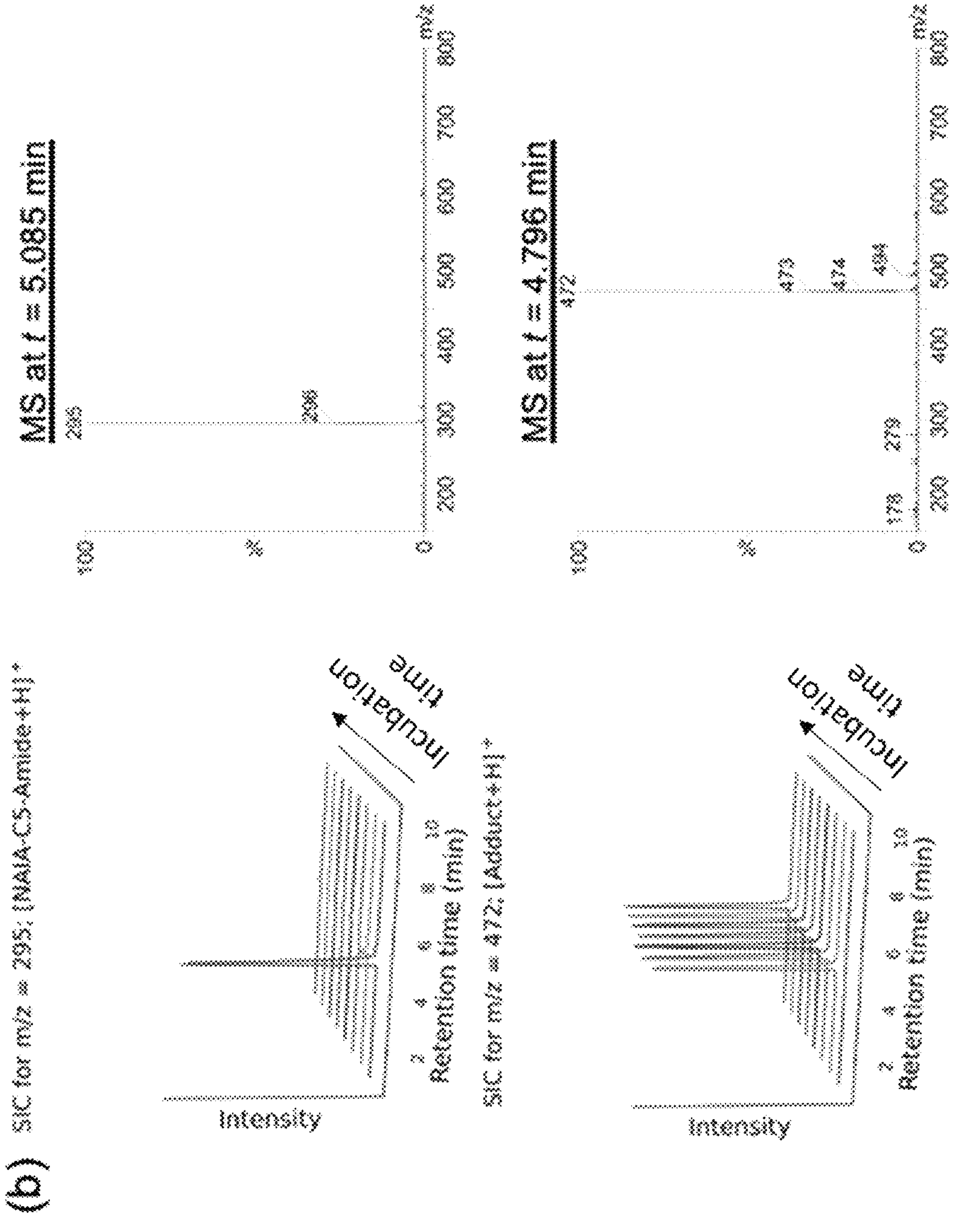
Figures 17C, 17D:
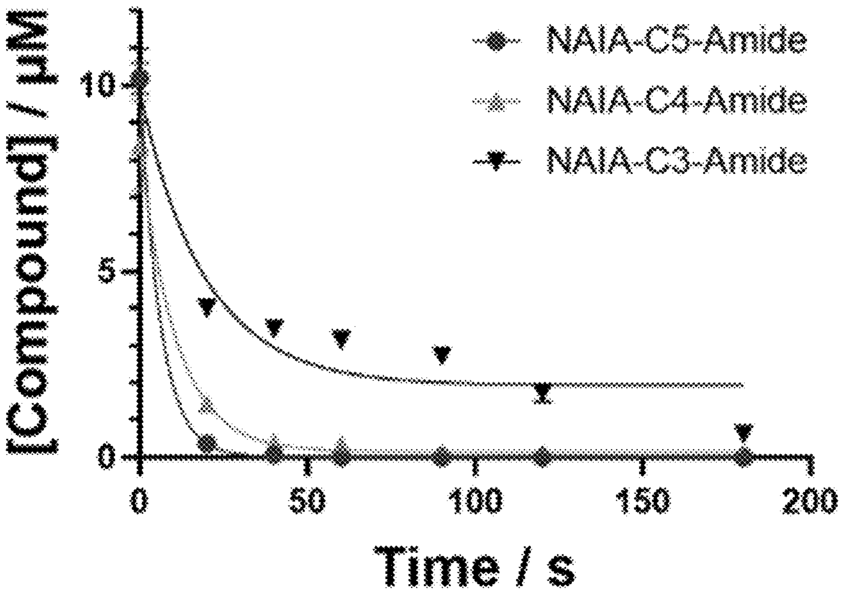

Example 7—LC-MS Experiment to Investigate Reactivity of NAIA-Amide Probes with Cysteine Next, we monitored the reaction between NAIA-amide (10 μM) and N-acetylcysteine methyl ester (250 μM) by LC-MS analysis (FIG. 17A). Complete conversion of NAIA-C5 amide was observed within 40 s as indicated by the disappearance of NAIA-C5 amide peak (t=5.09 min) and emergence of the adduct peat (t=4.80 min) in the LC trace (FIG. 17B). Likewise, the reaction of NAIA-C4 amide proceeded with fast kinetics and was completely consumed in 1 min (FIG. 17C). The calculated rate constant of NAIA-C5 amide and NAIA-C4 amide were 2-fold and 1.2-fold faster than NAIA (FIG. 17D). Interestingly, we found NAIA-C3 amide reacted relatively slower despite it still showed superior reaction kinetics over IAA (FIGS. 17C-17D). Owning to the excellent reaction rate of NAIA-C5 amide, it was taken forward for further comparative analysis in subsequent experiments.

Figure 17E:
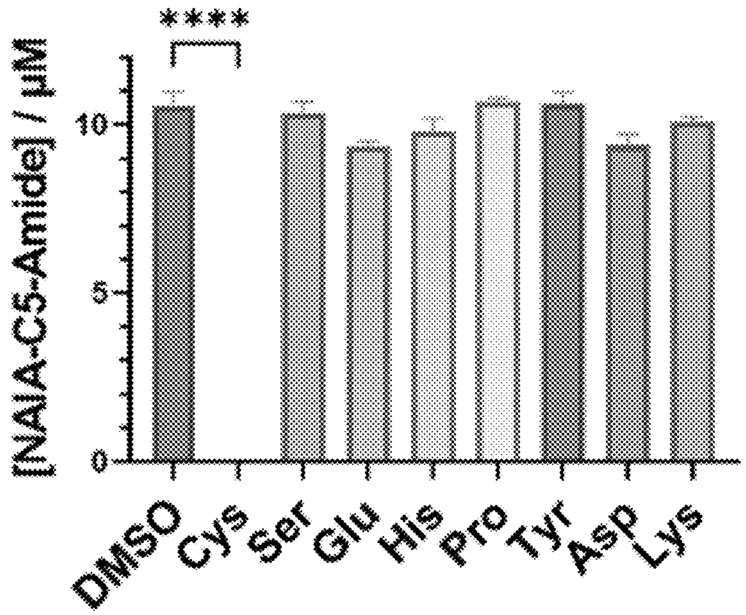
Figure 17F:
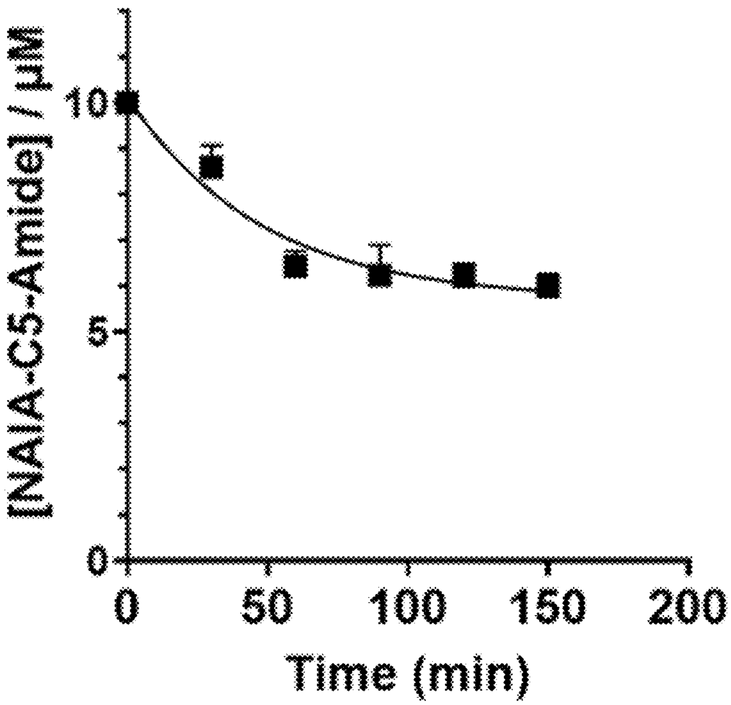

Example 8—LC-MS Experiment to Investigate Cys Selectivity and Stability of NAIA-Amide Probes To demonstrate the selectivity of NAIA-C5 amide towards other substrates, the consumption of probe was monitored in the presence of different nucleophilic residues. Upon addition of 3 equiv. amino acids, only incubation with cysteine consumed NAIA-C5 amide to an undetectable level (FIG. 17E). As fast-reacting probes are often susceptible to hydrolysis, we sought to investigate the aqueous stability of NAIA-C5 amide. A gradual degradation was observed in 3 hours (FIG. 17F). Taking the excellent reaction kinetics and a mere 14% degradation in 30 min into account, NAIA-C5 amide was considered to be a useful tool in cysteine profiling (FIG. 17C and FIG. 17F).

Example 9—Cysteine Labeling by NAIA-C5 Amide in Gel-Based Studies

Confirming the reaction between NAIA-C5 amide and cysteine in vitro, we moved on to evaluate its application for cysteine profiling in complex biological sample. To assess this, we performed gel-based ABPP in cell lysates and in live cells. HCT116 cell lysates were incubated with IAA, NAIA and NAIA-Amide, followed by installation of fluorophore by click chemistry. Then, the labelled proteins were resolved by SDS-PAGE and visualized by their in-gel fluorescence. In coherence to our previous observation, significantly stronger fluorescence was detected in samples incubated with NAIA or NAIA-C5 amide in a dose-dependent manner but not by other probes (FIG. 18A). The overall fluorescence intensity of NAIA-C5 amide was 3-fold higher than using IAA as the probe and was comparable to that by NAIA (FIG. 18A). In time-dependent experiments, a 15-minute incubation of NAIA-C5 amide with HCT116 cell lysates was sufficient to have decent labeling, highlighting its quick labeling (FIG. 18B).

Example 10—Chemical Synthesis and Characterization of NAI-DTB

NAI-DTB was synthesized according to our synthetic route outlined in FIG. 19. Two key intermediates, compounds 5 and D3, were synthesized using our established synthetic scheme[83] and reported method in literature[84]. Then through HATU-catalyzed amide coupling reaction, NAI-DTB was successfully synthesized and characterized by $^{1}H$ and $^{13}C\{^{1}H\}$ NMR (FIG. 20), as well as LC-MS. Details of the synthesis and characterization data can be found below.

NAI-DTB. HATU (44 mg, 0.15 mmol) was added to 5 (26 mg, 0.10 mmol) in anhydrous DMF solution at 0° C. After stirring for 15 min, the solution mixture was added with compound D3 (34.1 mg, 0.12 mmol), followed by triethylamine (43.5 μL, 0.31 mmol). The solution was stirred at room temperature overnight. The reaction was then quenched by the addition of saturated $NaHCO_3$(aq), and the aqueous layer was extracted by ethyl acetate. The organic layer was washed with saturated NaCl (aq) twice, dried by anhydrous $MgSO_4$ (s) and filtered. Volatile organic solvent was evaporated under reduced pressure, and the crude product was purified by column chromatography on silica gel using dichloromethane/methanol (92:8, v/v) as eluent, yielding NAI-DTB as a colourless film (32 mg, 63%). $^{1}H$ NMR ($CD_3OD$, 600 MHz): 8.37 (1H, d, J=9.0 Hz), 7.81 (1H, d, J=3.7 Hz), 7.20 (1H, dd, J=10.4 and 16.2 Hz), 7.15 (1H, d, J=2.4 Hz), 7.04 (1H, dd, J=2.4 and 9.0 Hz), 6.67 (1H, d, J=3.76 Hz), 6.61 (1H, dd, J=1.5 and 16.7 Hz), 6.06 (1H, dd, J=1.6 and 10.5 Hz), 4.54 (2H, s), 3.81 (1H, m), 3.68 (1H, m), 3.15 (2H, t, J=6.84 Hz), 2.16 (2H, t, J=7.5 Hz), 1.56-1.63 (2H, m), 1.52-1.56 (2H, m), 1.45-1.52 (4H, m), 1.25-1.44 (8H, m), 1.08 (3H, t, J=6.5 Hz). $^{13}C\{^{1}H\}$ NMR (d6-DMSO, 150 MHz) δ=171.9, 167.5, 163.3, 162.8, 154.6, 132.1, 131.5, 130.1, 128.1, 126.9, 117.0, 113.6, 108.8, 104.9, 67.5, 55.0, 50.2, 38.1, 38.0, 35.3, 29.5, 28.7, 26.59, 26.58, 25.55, 25.2, 15.4. MS ($ESI^+$): m/z 512 ($[M+H]^+$).

Example 11—Applications of NAI-DTB to Identify New Ligandable Hotspots in Metastatic Liver Cancers NAI-DTB has been utilized for profiling functional cysteines in liver cancer cells, with the goals to determine hyper-ligandable cysteines in metastatic liver cancer which should be potential hotspots for targeted therapy of this difficult-to-treat cancer.

Figure 21A:
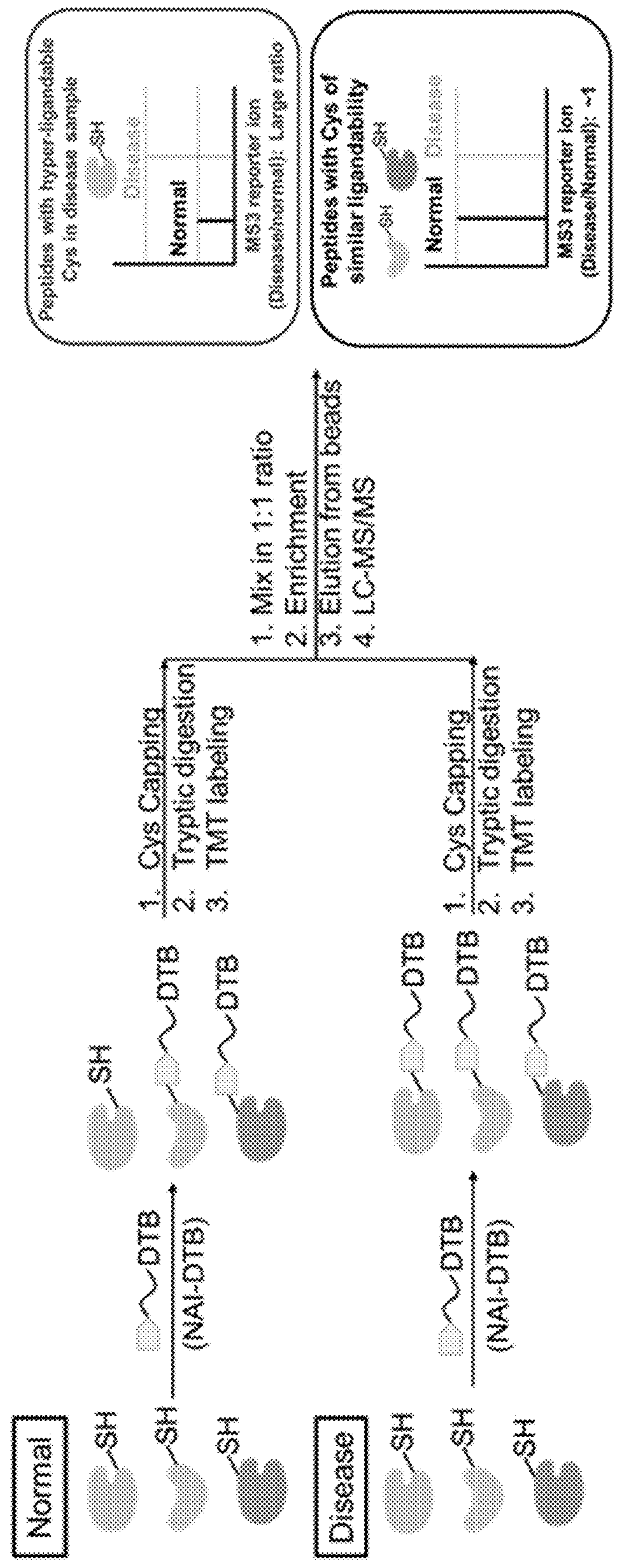
Figure 21B:
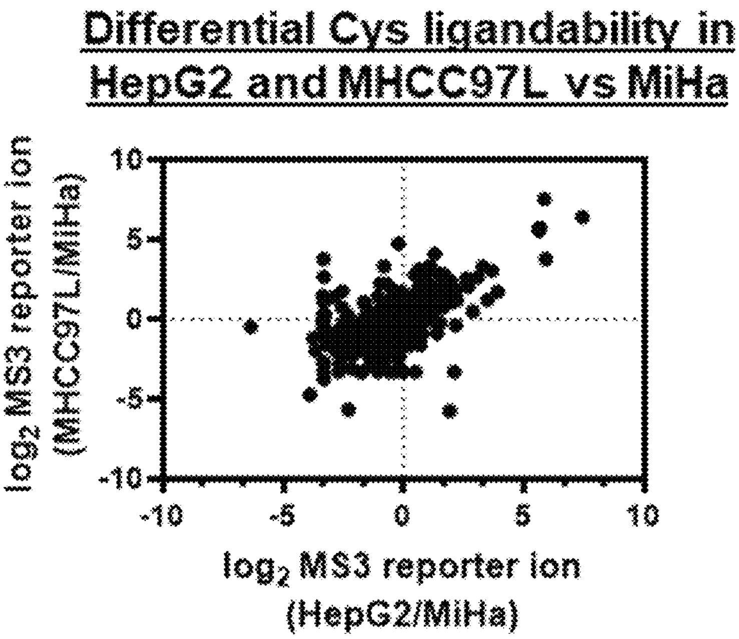
Figure 21C:
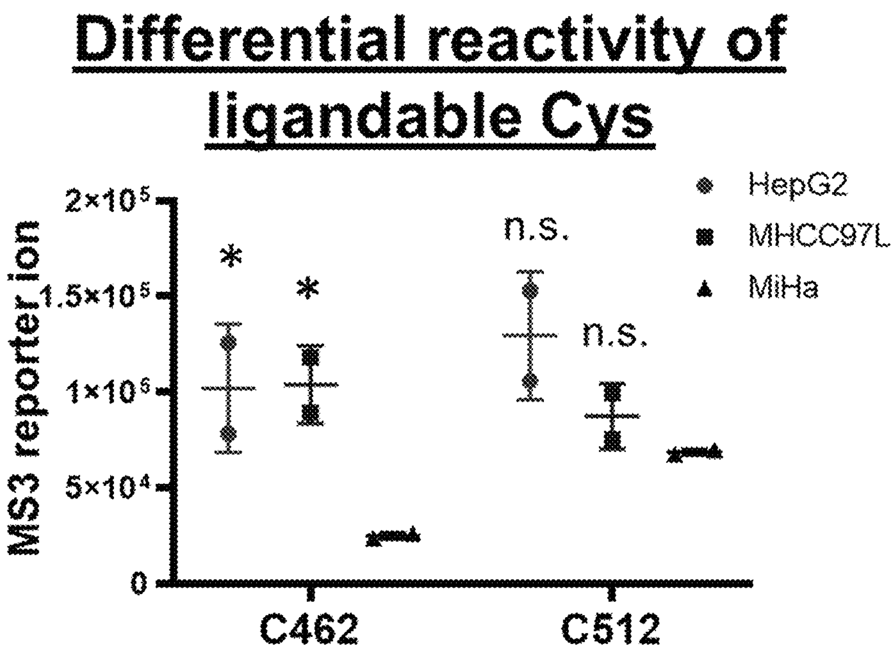
Figure 21D:
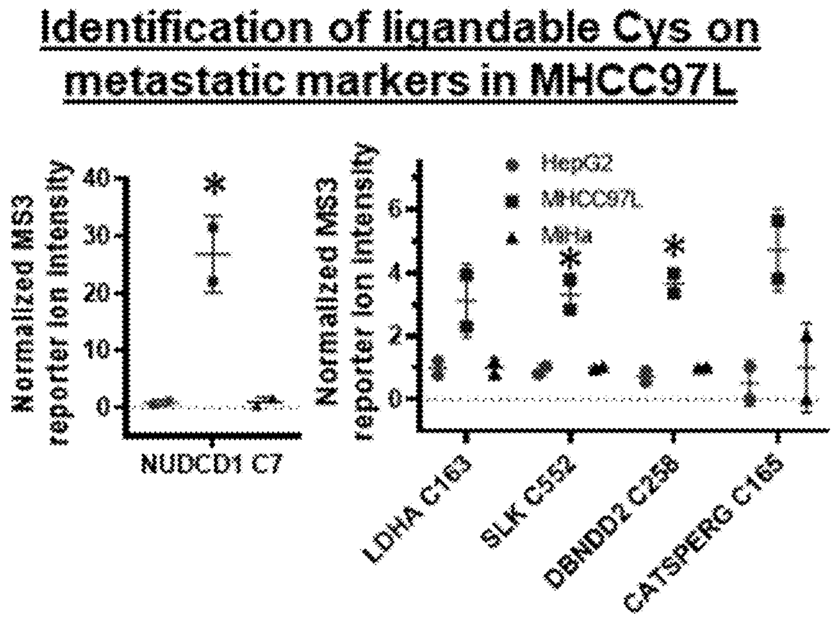
Figure 21E:
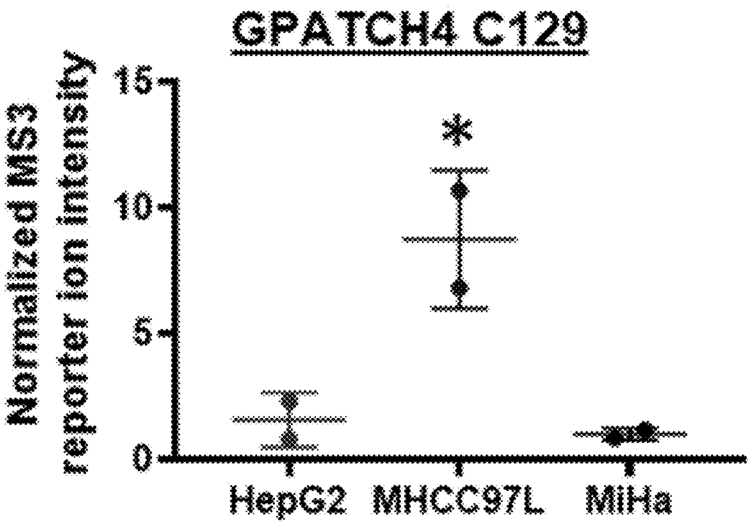
Figure 21F:
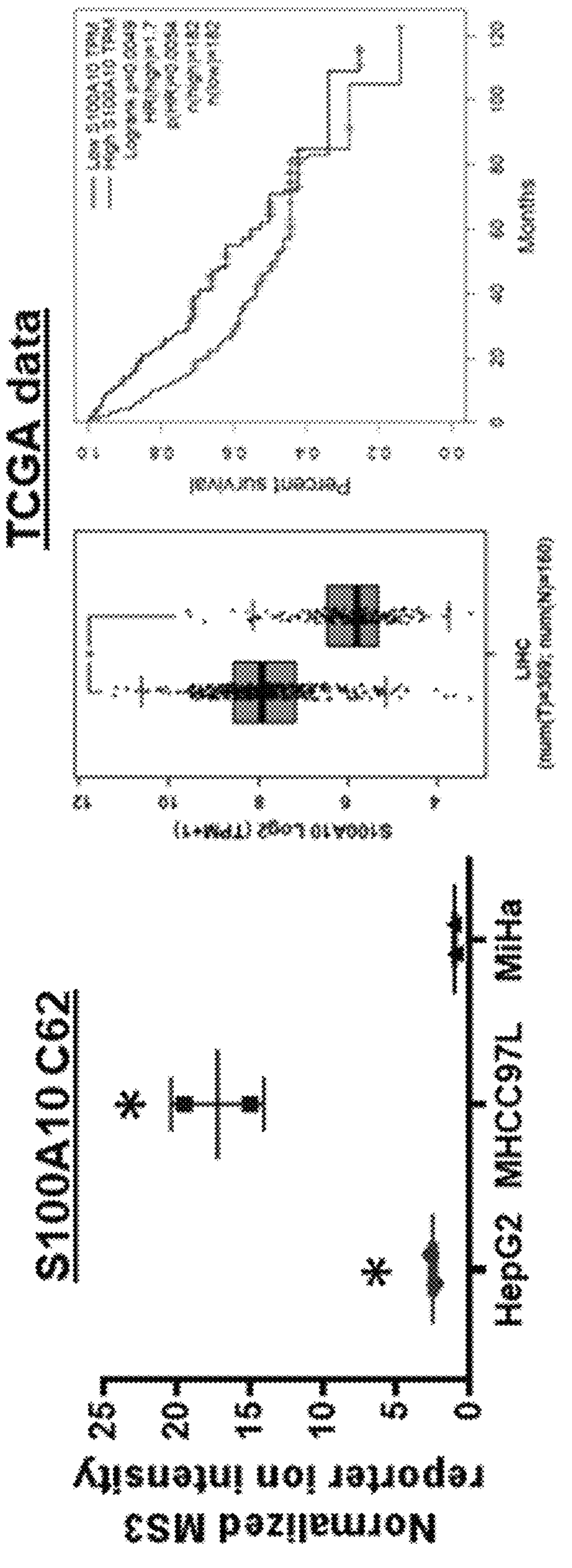

In this experiment, MiHa (immortalized normal liver cells), HepG2 (liver cancer cells) and MHCC97L (invasive liver cancer cells) cell lysates in PBS (2 mg/mL, 100 μL), respectively, were incubated with NAI-DTB (100 μM) at room temperature for 1 h, followed by Cys capping and tryptic digestion. The digested peptides labeled by NAI-DTB were pulled down by streptavidin beads, and the bound peptides were then eluted and labeled with TMT reagents for quantification of ligandability of cysteines in the three different cell lines by LC-MS/MS experiment (FIG. 21A). A number of Cys were found to show higher ligandability in HepG2 and MHCC97L cells (FIG. 21A), and many of them are on known metastatic protein markers (FIG. 21D), liver cancer driver (FIG. 21E) and poor prognostic markers (FIG. 21F)[85]. These Cys can be good binding site for covalent ligands to target for treating liver cancers. More importantly, all these Cys have not been identified by the current state-of-the-art cysteine profiling experiment by DBIA[14], indicating the importance of developing NAI-DTB as a new cysteine-reactive probe to further expand the pool of ligandable cysteines and proteins. In addition, using HTATSF1 as a representative example, we found 2 ligandable Cys on the protein, while only Cys462 showed significantly higher ligandability in cancerous HepG2 and MHCC97 cells but not for Cys512 (FIG. 21C). This demonstrates that some ligandable Cys shows differential reactivity, and not only expression levels, in liver cancer cells as compared to liver normal cells. Such changes in reactivity of these cysteines further support their possible roles on carcinogenesis, and hence can be good hotspots for targeted therapy.

Example 12—Applications of NAI-DTB to Identify New Ligandable Hotspots in Drug-Resistant Liver Cancers Lenvatinib is a first-line multiple kinase inhibitor for treating HCC, the most common type of liver cancer. Yet, drug resistance has been found in patients administered with Lenvatinib with unclear molecular mechanism[86,87]. These patients often show poor prognosis and survival rates with current treatment options, highlighting the urgent need for exploration of new drug targets in order to develop more effective therapy.

Figure 22A:
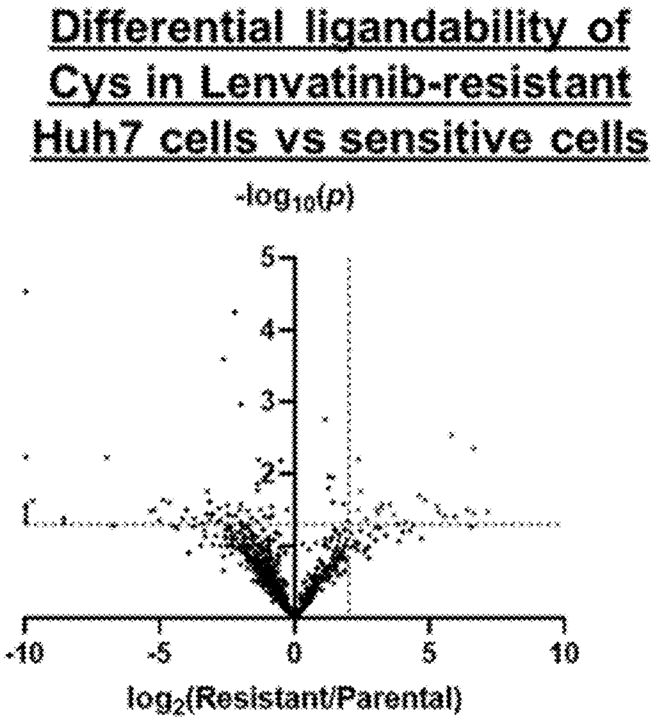
Figure 22B:
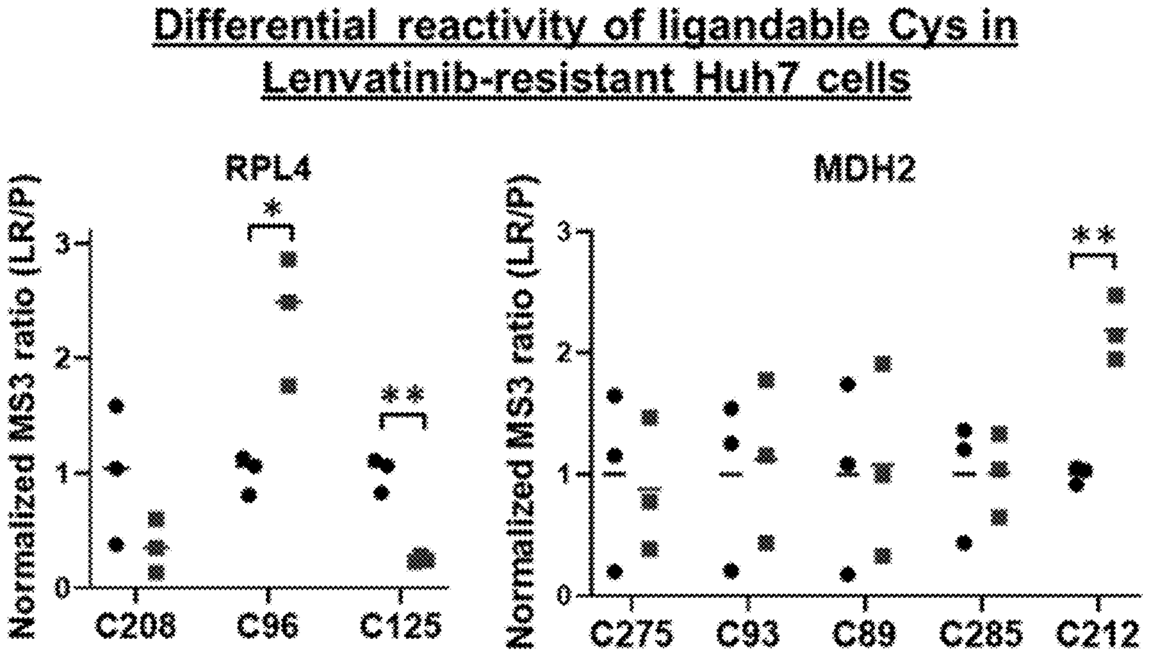
Figure 22C:
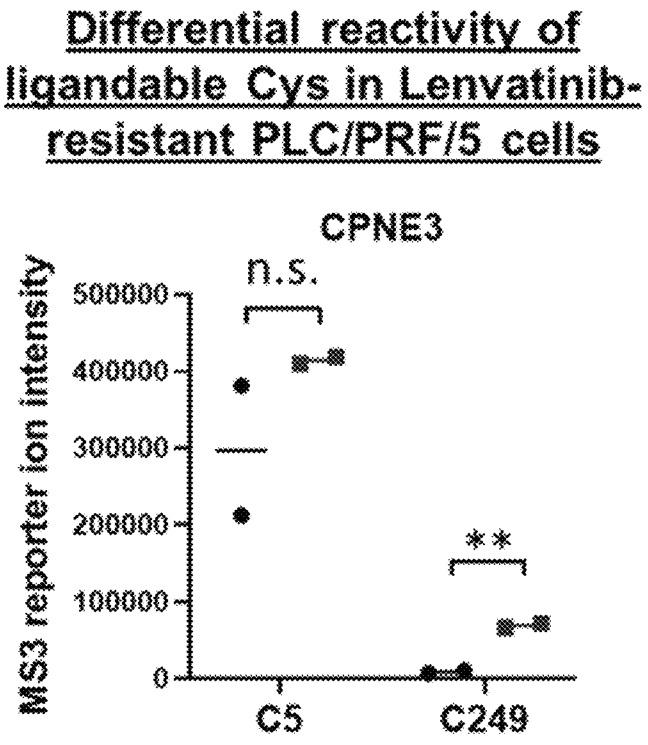
Figure 22D:
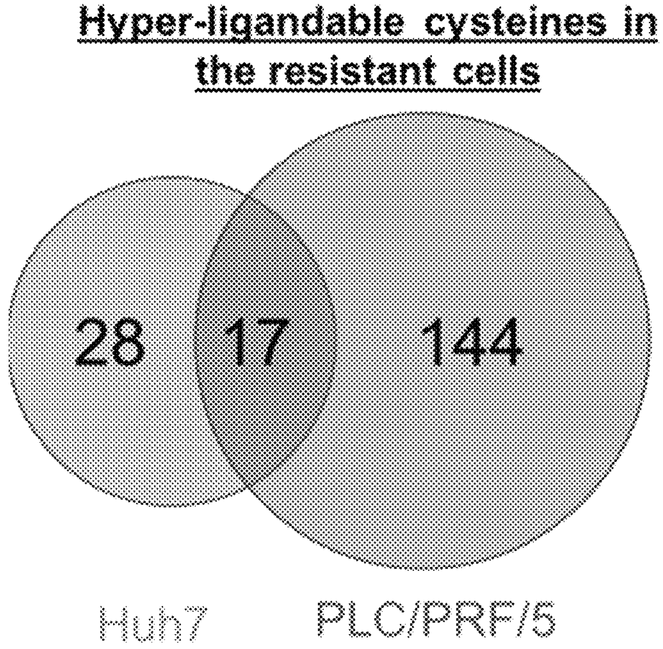
Figure 22E:
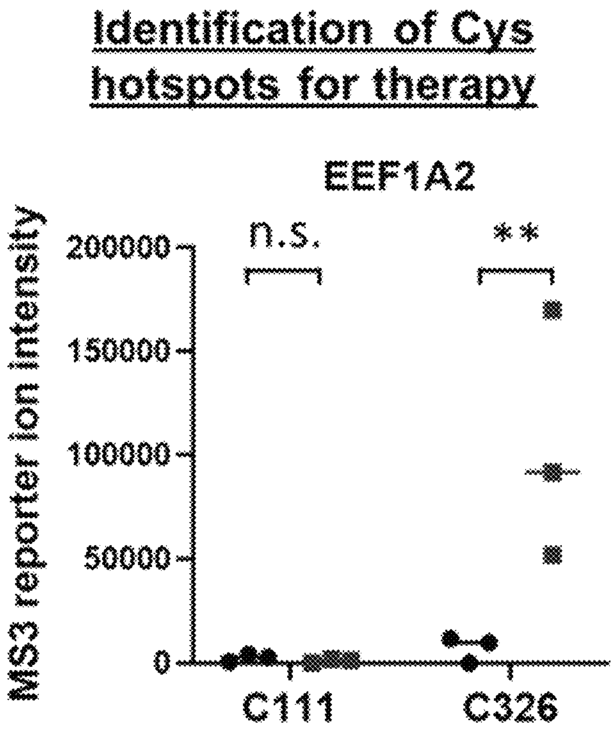

In view of the excellent performance of NAI-DTB to identify hyper-ligandable hotspots in metastatic HCC (FIGS. 21A-21F), this has prompted us to further apply NAI-DTB in studying Lenvatinib-resistant liver cancers. By running MS-based ABPP experiments using NAI-DTB on Lenvatinib-resistant Huh7 and the sensitive cells, a number of hyper-ligandable Cys were identified in the resistant cells (FIG. 22A). Interestingly, different Cys ligandability was found from different Cys residues on the same protein, e.g. RPL4 and MDH2 (FIG. 22B), illustrating changes in intrinsic reactivity of these Cys in the resistant cells instead of just changes in expression level. Similarly, experiment on another pair of resistant and sensitive PLC/PRF/5 cells also revealed differential Cys ligandability and reactivity (FIG. 22C). By comparing the results from Huh7 and PLC/PRF/5 pairs, 17 Cys were identified as the common targets (FIG. 22D and FIG. 22E), and these are the potential hotspots for covalent ligand to target in order to overcome the problem of Lenvatinib-resistance in cancer therapy.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Winterbourn, C. C.; Metodiewa, D., Reactivity of biologically important thiol compounds with superoxide and hydrogen peroxide. *Free Radic Biol Med* 1999, 27(3), 322-328.

2. Bulaj, G.; Kortemme, T.; Goldenberg, D. P., Ionization-Reactivity Relationships for Cysteine Thiols in Polypeptides. *Biochemistry* 1998, 37 (25), 8965-8972.

3. Maurais, A. J.; Weerapana, E., Reactive-cysteine profiling for drug discovery. *Curr Opin Chem Biol* 2019, 50, 29-36.

4. Hancock, J. T., The Role of Redox Mechanisms in Cell Signalling. *Mol Biotechnol* 2009, 43 (2), 162-166.

5. Hoch, D. G.; Abegg, D.; Adibekian, A., Cysteine-reactive probes and their use in chemical proteomics. *Chem Commun* (*Camb*) 2018, 54 (36), 451-4512.

6. Weerapana, E.; Wang, C.; Simon, G. M.; Richter, F.; Khare, S.; Dillon, M. B. D.; Bachovchin, D. A.; Mowen, K.; Baker, D.; Cravatt, B. F., Quantitative reactivity profiling predicts functional cysteines in proteomes. *Nature* 2010, 468 (7325), 790-795.

7. Alcock, L. J.; Perkins, M. V.; Chalker, J. M., Chemical methods for mapping cysteine oxidation. *Chemical Society Reviews* 2018, 47 (1), 231-268.

8. Deng, X.; Weerapana, E.; Ulanovskaya, O.; Sun, F.; Liang, H.; Ji, Q.; Ye, Y.; Fu, Y.; Zhou, L.; Li, J.; Zhang, H.; Wang, C.; Alvarez, S.; Hicks, L. M.; Lan, L.; Wu, M.; Cravatt, B. F.; He, C., Proteome-wide quantification and characterization of oxidation-sensitive cysteines in pathogenic bacteria. *Cell Host Microbe* 2013, 13 (3), 358-70.

9. Lindahl, M.; Mata-Cabana, A.; Kieselbach, T., The disulfide proteome and other reactive cysteine proteomes: analysis and functional significance. Antioxid Redox *Signal* 2011, 14 (12), 2581-642.

10. Pace, N. J.; Weerapana, E., Diverse Functional Roles of Reactive Cysteines. *ACS Chemical Biology* 2013, 8 (2), 283-296.

11. Paulsen, C. E.; Carroll, K. S., Cysteine-mediated redox signaling: chemistry, biology, and tools for discovery. *Chem Rev* 2013, 113 (7), 4633-79.

12. Backus, K. M.; Correia, B. E.; Lum, K. M.; Forli, S.; Homing, B. D.; González-Páez, G. E.; Chatterjee, S.; Lanning, B. R.; Teijaro, J. R.; Olson, A. J.; Wolan, D. W.; Cravatt, B. F., Proteome-wide covalent ligand discovery in native biological systems. *Nature* 2016, 534 (7608), 570-4.

13. Buttle, D. J.; Mort, J. S., Cysteine Proteases. In *Encyclopedia of Biological Chemistry* (*Second Edition*), Lennarz, W. J.; Lane, M. D., Eds. Academic Press: Waltham, 2013; pp 589-592.

14. Tinguely, J. N.; Wermuth, B., Identification of the reactive cysteine residue (Cys227) in human carbonyl reductase. *Eur J Biochem* 1999, 260 (1), 9-14.

15. Mondal, M. S.; Ruiz, A.; Bok, D.; Rando, R. R., Lecithin retinol acyltransferase contains cysteine residues essential for catalysis. *Biochemistry* 2000, 39 (17), 5215-20.

16. Reddie, K. G.; Carroll, K. S., Expanding the functional diversity of proteins through cysteine oxidation. *Curr Opin Chem Biol* 2008, 12 (6), 746-754.

17. Berg, J. M., Zinc Finger Domains: Hypotheses and Current Knowledge. *Annual Review of Biophysics and Biophysical Chemistry* 1990, 19 (1), 405-421.

18. Han, J.; Adman, E. T.; Beppu, T.; Codd, R.; Freeman, H. C.; Huq, L. L.; Loehr, T. M.; Sanders-Loehr, J., Resonance Raman spectra of plastocyanin and pseudoazurin: evidence for conserved cysteine ligand conformations in cupredoxins (blue copper proteins). *Biochemistry* 1991, 30 (45), 10904-13.

19. Werck-Reichhart, D.; Feyereisen, R., Cytochromes P450: a success story. *Genome Biology* 2000, 1 (6), reviews3003.1.

20. Speers, A. E.; Cravatt, B. F., Chemical strategies for activity-based proteomics.

*Chembiochem* 2004, 5 (1), 41-7.

21. Liu, Y.; Patricelli, M. P.; Cravatt, B. F., Activity-based protein profiling: The serine hydrolases. *Proceedings of the National Academy of Sciences* 1999, 96 (26), 14694.

22. Ward, C. C.; Kleinman, J. I.; Nomura, D. K., NHS-Esters As Versatile Reactivity-Based Probes for Mapping Proteome-Wide Ligandable Hotspots. *ACS Chem Biol* 2017, 12 (6), 1478-1483.

23. Counihan, J. L.; Wiggenhorn, A. L.; Anderson, K. E.; Nomura, D. K., Chemoproteomics-Enabled Covalent Ligand Screening Reveals ALDH3A1 as a Lung Cancer Therapy Target. *ACS Chemical Biology* 2018, 13 (8), 1970-1977.

24. Bateman, L. A.; Nguyen, T. B.; Roberts, A. M.; Miyamoto, D. K.; Ku, W. M.; Huffman, T. R.; Petri, Y.; Heslin, M. J.; Contreras, C. M.; Skibola, C. F.; Olzmann, J. A.; Nomura, D. K., Chemoproteomics-enabled covalent ligand screen reveals a cysteine hotspot in reticulon 4 that impairs ER morphology and cancer pathogenicity. *Chem Commun* (*Camb*) 2017, 53 (53), 7234-7237.

25. Weerapana, E.; Speers, A. E.; Cravatt, B. F., Tandem orthogonal proteolysis-activity-based protein profiling (TOP-ABPP)—a general method for mapping sites of probe modification in proteomes. *Nature Protocols* 2007, 2 (6), 1414-1425.

26. Niphakis, M. J.; Cravatt, B. F., Enzyme Inhibitor Discovery by Activity-Based Protein *Profiling. Annu Rev Biochem* 2014, 83 (1), 341-377.

27. Roberts, A. M.; Ward, C. C.; Nomura, D. K., Activity-based protein profiling for mapping and pharmacologically interrogating proteome-wide ligandable hotspots. *Curr Opin Biotechnol* 2017, 43, 25-33.

28. Grossman, E. A.; Ward, C. C.; Spradlin, J. N.; Bateman, L. A.; Huffman, T. R.; Miyamoto, D. K.; Kleinman, J. I.; Nomura, D. K., Covalent Ligand Discovery against Druggable Hotspots Targeted by Anti-cancer Natural Products. *Cell Chem Biol* 2017, 24 (11), 1368-1376.e4.

29. Cravatt, B. F.; Wright, A. T.; Kozarich, J. W., Activity-based protein profiling: from enzyme chemistry to proteomic chemistry. *Annu Rev Biochem* 2008, 77, 383-414.

30. Serafimova, I. M.; Pufall, M. A.; Krishnan, S.; Duda, K.; Cohen, M. S.; Maglathlin, R. L.; McFarland, J. M.; Miller, R. M.; Frödin, M.; Taunton, J., Reversible targeting of noncatalytic cysteines with chemically tuned electrophiles. *Nat Chem Biol* 2012, 8 (5), 471-476.

31. Boike, L.; Cioffi, A. G.; Majewski, F. C.; Co, J.; Henning, N. J.; Jones, M. D.; Liu, G.; McKenna, J. M.; Tallarico, J. A.; Schirle, M.; Nomura, D. K., Discovery of a Functional Covalent Ligand Targeting an Intrinsically Disordered Cysteine within MYC. *Cell chemical biology* 2021, 28 (1), 4-13.e17.

32. Lanning, B. R.; Whitby, L. R.; Dix, M. M.; Douhan, J.; Gilbert, A. M.; Hett, E. C.; Johnson, T. O.; Joslyn, C.; Kath, J. C.; Niessen, S.; Roberts, L. R.; Schnute, M. E.; Wang, C.; Hulce, J. J.; Wei, B.; Whiteley, L. O.; Hayward, M. M.; Cravatt, B. F., A road map to evaluate the proteome-wide selectivity of covalent kinase inhibitors. *Nature Chemical Biology* 2014, 10 (9), 760-767.

33. Resnick, E.; Bradley, A.; Gan, J.; Douangamath, A.; Krojer, T.; Sethi, R.; Geurink, P. P.; Aimon, A.; Amitai, G.; Bellini, D.; Bennett, J.; Fairhead, M.; Fedorov, O.; Gabizon, R.; Gan, J.; Guo, J.; Plotnikov, A.; Reznik, N.; Ruda, G. F.; Diaz-Sáez, L.; Straub, V. M.; Szommer, T.; Velupillai, S.; Zaidman, D.; Zhang, Y.; Coker, A. R.; Dowson, C. G.; Barr, H. M.; Wang, C.; Huber, K. V. M.; Brennan, P. E.; Ovaa, H.; von Delft, F.; London, N., Rapid Covalent-Probe Discovery by Electrophile-Fragment Screening. *Journal of the American Chemical Society* 2019, 141 (22), 8951-8968.

34. Chung, C. Y.-S.; Shin, H. R.; Berdan, C. A.; Ford, B.; Ward, C. C.; Olzmann, J. A.; Zoncu, R.; Nomura, D. K., Covalent targeting of the vacuolar H+-ATPase activates autophagy via mTORC1 inhibition. *Nat Chem Biol* 2019, 15 (8), 776-785.

35. Zhang, X.; Crowley, V. M.; Wucherpfennig, T. G.; Dix, M. M.; Cravatt, B. F., Electrophilic PROTACs that degrade nuclear proteins by engaging DCAF16. *Nat Chem Biol* 2019, 15 (7), 737-746.

36. Janes, M. R.; Zhang, J.; Li, L.-S.; Hansen, R.; Peters, U.; Guo, X.; Chen, Y.; Babbar, A.; Firdaus, S. J.; Darjania, L.; Feng, J.; Chen, J. H.; Li, S.; Li, S.; Long, Y. O.; Thach, C.; Liu, Y.; Zarieh, A.; Ely, T.; Kucharski, J. M.; Kessler, L. V.; Wu, T.; Yu, K.; Wang, Y.; Yao, Y.; Deng, X.; Zarrinkar, P. P.; Brehmer, D.; Dhanak, D.; Lorenzi, M. V.; Hu-Lowe, D.; Patricelli, M. P.; Ren, P.; Liu, Y., Targeting KRAS Mutant Cancers with a Covalent G12C-Specific Inhibitor. *Cell* 2018, 172 (3), 578-589.e17.

37. Henning, N. J.; Manford, A. G.; Spradlin, J. N.; Brittain, S. M.; Zhang, E.; McKenna, J. M.; Tallarico, J. A.; Schirle, M.; Rape, M.; Nomura, D. K., Discovery of a Covalent FEM1B Recruiter for Targeted Protein Degradation Applications. *J. Am. Chem. Soc* 2022, 144 (2), 701-708.

38. Ostrem, J. M.; Peters, U.; Sos, M. L.; Wells, J. A.; Shokat, K. M., K-Ras(G12C) inhibitors allosterically control GTP affinity and effector interactions. *Nature* 2013, 503 (7477), 548-551.

39. Canon, J.; Rex, K.; Saiki, A. Y.; Mohr, C.; Cooke, K.; Bagal, D.; Gaida, K.; Holt, T.; Knutson, C. G.; Koppada, N.; Lanman, B. A.; Werner, J.; Rapaport, A. S.; San Miguel, T.; Ortiz, R.; Osgood, T.; Sun, J.-R.; Zhu, X.; McCarter, J. D.; Volak, L. P.; Houk, B. E.; Fakih, M. G.; O'Neil, B. H.; Price, T. J.; Falchook, G. S.; Desai, J.; Kuo, J.; Govindan, R.; Hong, D. S.; Ouyang, W.; Henary, H.; Arvedson, T.; Cee, V. J.; Lipford, J. R., The clinical KRAS(G12C) inhibitor AMG 510 drives anti-tumour immunity. *Nature* 2019, 575 (7781), 217-223.

40. Wong, H. L.; Liebler, D. C., Mitochondrial protein targets of thiol-reactive electrophiles. *Chem Res Toxicol* 2008, 21 (4), 796-804.

41. Smyth, D. G.; Nagamatsu, A.; Fruton, J. S., Some Reactions of N-Ethylmaleimide1. *Journal of the American Chemical Society* 1960, 82 (17), 4600-4604.

42. Wright, A. T.; Song, J. D.; Cravatt, B. F., A Suite of Activity-Based Probes for Human Cytochrome P450 Enzymes. *Journal of the American Chemical Society* 2009, 131 (30), 10692-10700.

43. Wang, C.; Weerapana, E.; Blewett, M. M.; Cravatt, B. F., A chemoproteomic platform to quantitatively map targets of lipid-derived electrophiles. *Nat Methods* 2014, 11 (1), 79-85.

44. Doom, J. A.; Petersen, D. R., Covalent modification of amino acid nucleophiles by the lipid peroxidation products 4-hydroxy-2-nonenal and 4-oxo-2-nonenal. *Chem Res Toxicol* 2002, 15 (11), 1445-50.

45. Friedman, M.; Cavins, J. F.; Wall, J. S., Relative Nucleophilic Reactivities of Amino Groups and Mercaptide Ions in Addition Reactions with a O-Unsaturated Compounds 1,2. *Journal of the American Chemical Society* 1965, 87 (16), 3672-3682.

46. Kato, D.; Boatright, K. M.; Berger, A. B.; Nazif, T.; Blum, G.; Ryan, C.; Chehade, K. A.; Salvesen, G. S.; Bogyo, M., Activity-based probes that target diverse cysteine protease families. *Nat Chem Biol* 2005, 1 (1), 33-8.

47. Blum, G.; Mullins, S. R.; Keren, K.; Fonovic, M.; Jedeszko, C.; Rice, M. J.; Sloane, B. F.; Bogyo, M., Dynamic imaging of protease activity with fluorescently quenched activity-based probes. *Nat Chem Biol* 2005, 1 (4), 203-9.

48. Qin, W.; Zhang, Y.; Tang, H.; Liu, D.; Chen, Y.; Liu, Y.; Wang, C., Chemoproteomic Profiling of Itaconation by Bioorthogonal Probes in Inflammatory Macrophages. *J. Am. Chem. Soc* 2020, 142 (25), 10894-10898.

49. Cole, R. D.; Stein, W. H.; Moore, S., On the cysteine content of human hemoglobin. *J Biol Chem* 1958, 233 (6), 1359-63.

50. Dickens, F., Interaction of halogenacetates and SH compounds: The reaction of halogenacetic acids with glutathione and cysteine. The mechanism of iodoacetate poisoning of glyoxalase. *Biochem J* 1933, 27 (4), 1141-51.

51. Zambaldo, C.; Vinogradova, E. V.; Qi, X.; Iaconelli, J.; Suciu, R. M.; Koh, M.; Senkane, K.; Chadwick, S. R.; Sanchez, B. B.; Chen, J. S.; Chatterjee, A. K.; Liu, P.; Schultz, P. G.; Cravatt, B. F.; Bollong, M. J., 2-Sulfonylpyridines as Tunable, Cysteine-Reactive Electrophiles. *J Am Chem Soc* 2020, 142 (19), 8972-8979.

52. Bak, D. W.; Pizzagalli, M. D.; Weerapana, E., Identifying Functional Cysteine Residues in the Mitochondria. *ACS Chem Biol* 2017, 12 (4), 947-957.

53. Martell, J.; Seo, Y.; Bak, Daniel W.; Kingsley, Samuel F.; Tissenbaum, Heidi A.; Weerapana, E., Global Cysteine-Reactivity Profiling during Impaired Insulin/IGF-1 Signaling in *C. elegans* Identifies Uncharacterized Mediators of Longevity. *Cell Chemical Biology* 2016, 23 (8), 955-966.

54. Isor, A.; Chartier, B. V.; Abo, M.; Currens, E. R.; Weerapana, E.; McCulla, R. D., Identifying cysteine residues susceptible to oxidation by photoactivatable atomic oxygen precursors using a proteome-wide analysis. *RSC Chemical Biology* 2021, 2 (2), 577-591.

55. Nielsen, M. L.; Vermeulen, M.; Bonaldi, T.; Cox, J.; Moroder, L.; Mann, M., Iodoacetamide-induced artifact mimics ubiquitination in mass spectrometry. *Nat Methods* 2008, 5 (6), 459-60.

56. Abegg, D.; Frei, R.; Cerato, L.; Prasad Hari, D.; Wang, C.; Waser, J.; Adibekian, A., Proteome-Wide Profiling of Targets of Cysteine reactive Small Molecules by Using Ethynyl Benziodoxolone Reagents. *Angew Chem Int Ed Engl* 2015, 54 (37), 10852-7.

57. Abo, M.; Bak, D. W.; Weerapana, E., Optimization of Caged Electrophiles for Improved Monitoring of Cysteine Reactivity in Living Cells. *Chembiochem* 2017, 18 (1), 81-84.

58. Abo, M.; Weerapana, E., A Caged Electrophilic Probe for Global Analysis of Cysteine Reactivity in Living Cells. *J. Am. Chem. Soc* 1900, 137(22), 7087-7090.
59. Shannon, D. A.; Banerjee, R.; Webster, E. R.; Bak, D. W.; Wang, C.; Weerapana, E., Investigating the Proteome Reactivity and Selectivity of Aryl Halides. *Journal of the American Chemical Society* 2014, 136 (9), 3330-3333.
60. Motiwala, H. F.; Kuo, Y.-H.; Stinger, B. L.; Palfey, B. A.; Martin, B. R., Tunable Heteroaromatic Sulfones Enhance in-Cell Cysteine Profiling. *J. Am. Chem. Soc* 2020, 142 (4), 1801-1810.
61. Tokunaga, K.; Sato, M.; Kuwata, K.; Miura, C.; Fuchida, H.; Matsunaga, N.; Koyanagi, S.; Ohdo, S.; Shindo, N.; Ojida, A., Bicyclobutane Carboxylic Amide as a Cysteine-Directed Strained Electrophile for Selective Targeting of Proteins. *J. Am. Chem. Soc* 2020,142 (43), 18522-18531.
62. Wang, C.; Abegg, D.; Hoch, D. G.; Adibekian, A., Chemoproteomics-Enabled Discovery of a Potent and Selective Inhibitor of the DNA Repair Protein MGMT. *Angew. Chem. Int. Ed* 2016, 55 (8), 2911-2915.
63. Eaton, J. K.; Furst, L.; Ruberto, R. A.; Moosmayer, D.; Hilpmann, A.; Ryan, M. J.; Zimmermann, K.; Cai, L. L.; Niehues, M.; Badock, V.; Kramm, A.; Chen, S.; Hillig, R. C.; Clemons, P. A.; Gradl, S.; Montagnon, C.; Lazarski, K. E.; Christian, S.; Bajrami, B.; Neuhaus, R.; Eheim, A. L.; Viswanathan, V. S.; Schreiber, S. L., Selective covalent targeting of GPX4 using masked nitrile-oxide electrophiles. *Nat Chem Biol* 2020, 16 (5), 497-506.
64. Sundberg, R. J., *Indoles*. Academic Press: London, 1996.
65. Linda, P.; Stener, A.; Cipiciani, A.; Savelli, G., Hydrolysis of amides. Kinetics and mechanism of the basic hydrolysis of N-acylpyrroles, N-acylindoles and N-acylcarbazoles. *Journal of Heterocyclic Chemistry* 1983, 20 (1), 247-248.
66. Wishart, D. S.; Knox, C.; Guo, A. C.; Cheng, D.; Shrivastava, S.; Tzur, D.; Gautam, B.; Hassanali, M., DrugBank: a knowledgebase for drugs, drug actions and drug targets. *Nucleic Acids Res* 2008, 36 (suppl-1), D901-D906.
67. Wishart, D. S.; Feunang, Y. D.; Guo, A. C.; Lo, E. J.; Marcu, A.; Grant, J. R.; Sajed, T.; Johnson, D.; Li, C.; Sayeeda, Z.; Assempour, N.; Iynkkaran, I.; Liu, Y.; Maciejewski, A.; Gale, N.; Wilson, A.; Chin, L.; Cummings, R.; Le, D.; Pon, A.; Knox, C.; Wilson, M., DrugBank 5.0: a major update to the DrugBank database for 2018. *Nucleic Acids Res* 2018, 46 (D1), D1074-D1082.
68. Boyle, E. I.; Weng, S.; Gollub, J.; Jin, H.; Botstein, D.; Cherry, J. M.; Sherlock, G., GO::TermFinder—open source software for accessing Gene Ontology information and finding significantly enriched Gene Ontology terms associated with a list of genes. Bioinformatics 2004, 20 (18), 3710-3715.
69. Adibekian, A.; Martin, B. R.; Wang, C.; Hsu, K.-L.; Bachovchin, D. A.; Niessen, S.; Hoover, H.; Cravatt, B. F., Click-generated triazole ureas as ultrapotent in vivo-active serine hydrolase inhibitors. *Nature Chemical Biology* 2011, 7 (7), 469-478.
70. Bushweller, J. H., Targeting transcription factors in cancer—from undruggable to reality. *Nat Rev Cancer* 2019, 19 (11), 611-624.
71. Bak, D. W.; Weerapana, E., Cysteine-mediated redox signalling in the mitochondria. *Mol. Biosyst.* 2015, 11 (3), 678-697.
72. Leichert, L. I.; Gehrke, F.; Gudiseva, H. V.; Blackwell, T.; Ilbert, M.; Walker, A. K.; Strahler, J. R.; Andrews, P. C.; Jakob, U., Quantifying Changes in the Thiol Redox Proteome upon Oxidative Stress in vivo. *Proc. Natl. Acad. Sci. U.S.A.* 2008, 105 (24), 8197-8202.
73. Gygi, S. P.; Rist, B.; Gerber, S. A.; Turecek, F.; Gelb, M. H.; Aebersold, R., Quantitative analysis of complex protein mixtures using isotope-coded affinity tags. *Nat. Biotechnol.* 1999, 17 (10), 994-9.
74. Abo, M.; Li, C.; Weerapana, E., Isotopically-Labeled Iodoacetamide-Alkyne Probes for Quantitative Cysteine-Reactivity Profiling. *Mol. Pharm.* 2018, 15 (3), 743-749.
75. Bechtel, T. J.; Li, C.; Kisty, E. A.; Maurais, A. J.; Weerapana, E., Profiling Cysteine Reactivity and Oxidation in the Endoplasmic Reticulum. *ACS Chem. Biol.* 2020, 15 (2), 543-553.
76. Jessani, N.; Humphrey, M.; McDonald, W. H.; Niessen, S.; Masuda, K.; Gangadharan, B.; Yates, r. J. R.; Mueller, B. M.; Cravatt, B. F., Carcinoma and Stromal Enzyme Activity Profiles Associated with Breast Tumor Growth in vivo. *Proc Nad Acad Sci USA* 2004, 101 (38), 13756-13761.
77. Xu, T.; Park, S. K.; Venable, J. D.; Wohlschlegel, J. A.; Diedrich, J. K.; Cociorva, D.; Lu, B.; Liao, L.; Hewel, J.; Han, X.; Wong, C. C. L.; Fonslow, B.; Delahunty, C.; Gao, Y.; Shah, H.; Yates, J. R., 3rd, ProLuCID: An improved SEQUEST-like algorithm with enhanced sensitivity and specificity. *J Proteomics* 2015, 129, 16-24.
78. Lai, H., Koo, T., Nomura, D., & Chung, C. Y.-S. (2022). N-Acryloylindole-alkyne (NAIA) enables profiling new ligandable hotspots in chemoproteomics experiments and imaging thiol oxidation. ChemRxiv. doi:10.26434/chemrxiv-2022-khww5.
79. Kuljanin, M., Mitchell, D. C., Schweppe, D. K., Gikandi, A. S., Nusinow, D. P., Bulloch, N. J., Vinogradova, E. V., Wilson, D. L., Kool, E. T., Mancias, J. D., Cravatt, B. F., & Gygi, S. P. (2021). Reimagining high-throughput profiling of reactive cysteines for cell-based screening of large electrophile libraries. *Nature Biotechnology,* 39(5), 630-641.
80. Bailey, M. H., Tokheim, C., Porta-Pardo, E., Sengupta, S., Bertrand, D., Weerasinghe, A., Colaprico, A., Wendl, M. C., Kim, J., Reardon, B., Ng, P. K., Jeong, K. J., Cao, S., Wang, Z., Gao, J., Gao, Q., Wang, F., Liu, E. M., Mularoni, L., Rubio-Perez, C., . . . Ding, L. (2018). Comprehensive Characterization of Cancer Driver Genes and Mutations. Cell, 173(2), 371-385.e18.
81. Kudo, M., Finn, R. S., Qin, S., Han, K. H., Ikeda, K., Piscaglia, F., Baron, A., Park, J. W., Han, G., Jassem, J., Blanc, J. F., Vogel, A., Komov, D., Evans, T., Lopez, C., Dutcus, C., Guo, M., Saito, K., Kraljevic, S., Tamai, T., . . . Cheng, A. L. (2018). Lenvatinib versus sorafenib in first-line treatment of patients with unresectable hepatocellular carcinoma: a randomised phase 3 non-inferiority trial. Lancet (London, England), 391(10126), 1163-1173.
82. Hu, B., Zou, T., Qin, W., Shen, X., Su, Y., Li, J., Chen, Y., Zhang, Z., Sun, H., Zheng, Y., Wang, C. Q., Wang, Z., Li, T. E., Wang, S., Zhu, L., Wang, X., Fu, Y., Ren, X., Dong, Q., & Qin, L. X. (2022). Inhibition of EGFR overcomes acquired lenvatinib resistance driven by STAT3-ABCB1 signaling in hepatocellular carcinoma. Cancer research, CAN-21-4140. Advance online publication.

83. Lai, H., Koo, T., Nomura, D., & Chung, C. Y.-S. (2022). N-Acryloylindole-alkyne (NAIA) enables profiling new ligandable hotspots in chemoproteomics experiments and imaging thiol oxidation. *ChemRxiv*. doi:10.26434/chemrxiv-2022-khww5.

84. Kuljanin, M., Mitchell, D. C., Schweppe, D. K., Gikandi, A. S., Nusinow, D. P., Bulloch, N. J., Vinogradova, E. V., Wilson, D. L., Kool, E. T., Mancias, J. D., Cravatt, B. F., & Gygi, S. P. (2021). Reimagining high-throughput profiling of reactive cysteines for cell-based screening of large electrophile libraries. *Nature Biotechnology,* 39(5), 630-641.

85. Bailey, M. H., Tokheim, C., Porta-Pardo, E., Sengupta, S., Bertrand, D., Weerasinghe, A., Colaprico, A., Wendl, M. C., Kim, J., Reardon, B., Ng, P. K., Jeong, K. J., Cao, S., Wang, Z., Gao, J., Gao, Q., Wang, F., Liu, E. M., Mularoni, L., Rubio-Perez, C., . . . Ding, L. (2018). Comprehensive Characterization of Cancer Driver Genes and Mutations. *Cell,* 173(2), 371-385.e18.

86. Kudo, M., Finn, R. S., Qin, S., Han, K. H., Ikeda, K., Piscaglia, F., Baron, A., Park, J. W., Han, G., Jassem, J., Blanc, J. F., Vogel, A., Komov, D., Evans, T., Lopez, C., Dutcus, C., Guo, M., Saito, K., Kraljevic, S., Tamai, T., . . . Cheng, A. L. (2018). Lenvatinib versus sorafenib in first-line treatment of patients with unresectable hepatocellular carcinoma: a randomised phase 3 non-inferiority trial. *Lancet* (London, England), 391 (10126), 1163-1173.

87. Hu, B., Zou, T., Qin, W., Shen, X., Su, Y., Li, J., Chen, Y., Zhang, Z., Sun, H., Zheng, Y., Wang, C. Q., Wang, Z., Li, T. E., Wang, S., Zhu, L., Wang, X., Fu, Y., Ren, X., Dong, Q., & Qin, L. X. (2022). Inhibition of EGFR overcomes acquired lenvatinib resistance driven by STAT3-ABCB1 signaling in hepatocellular carcinoma. *Cancer research*, CAN-21-4140. Advance online publication.

We claim:

1. A compound having the formula of:

Formula (II)

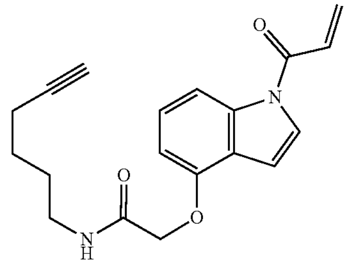

Formula (III)

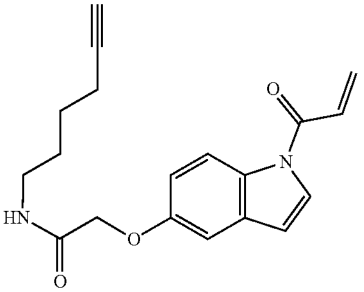

-continued

Formula (IV)

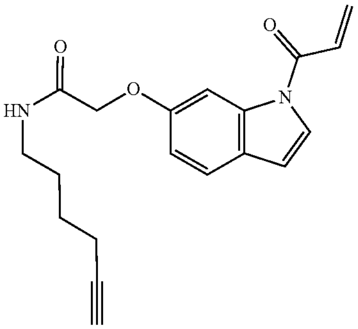

Formula (V)

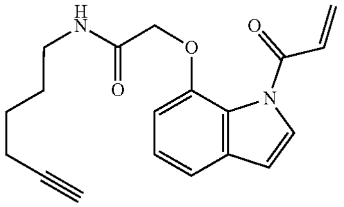

Formula (VI)

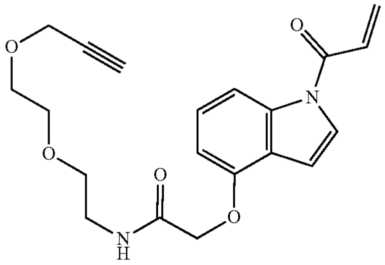

Formula (VII)

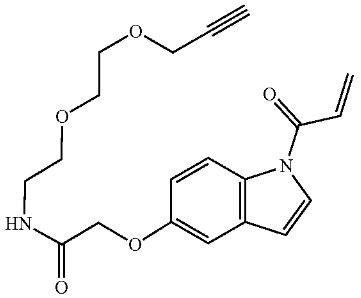

Formula (VIII)

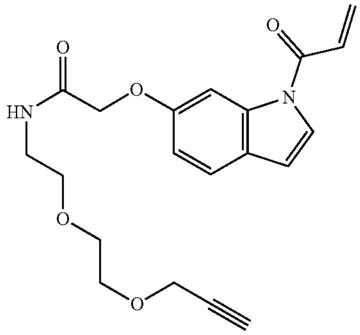

-continued
Formula (IX)
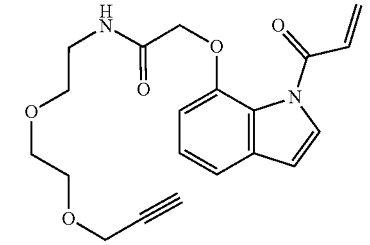
Formula (XII)
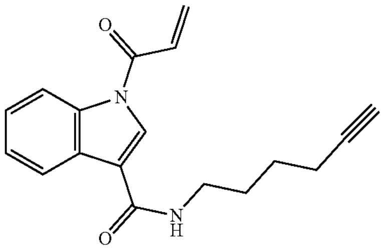
Formula (XIII)
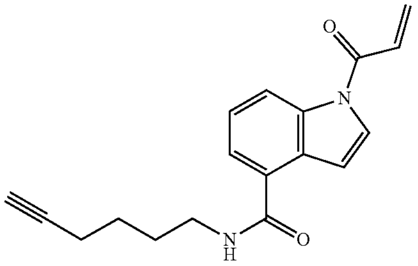
-continued
Formula (XIV)
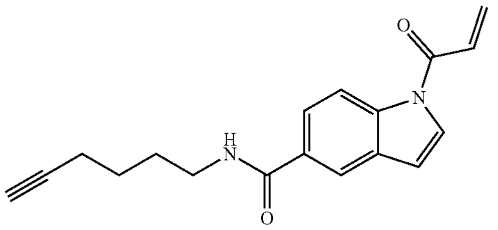
or
Formula (XV)
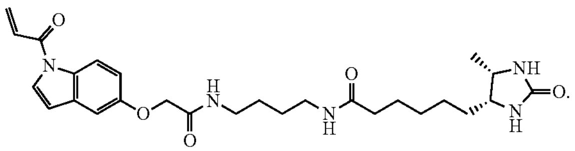
.
2. A composition comprising the compound of claim 1 and at least one carrier or excipient.
3. The composition of claim 2, wherein the compound is at a concentration of about 0.1 nM to about 100 mM, or about 10 μM.
* * * * *